US008716530B2

(12) United States Patent  (10) Patent No.: US 8,716,530 B2
DeGrado et al.  (45) Date of Patent: May 6, 2014

(54) FACIALLY AMPHIPHILIC POLYARYL AND POLYARYLALKYNYL POLYMERS AND OLIGOMERS AND USES THEREOF

(75) Inventors: William F. DeGrado, Moylan, PA (US); Dahui Liu, Wynnewood, PA (US); Gregory N. Tew, Amherst, MA (US); Michael L. Klein, Ocean City, NJ (US)

(73) Assignee: The Trustess of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/365,840

(22) Filed: Feb. 3, 2012

(65) Prior Publication Data

US 2012/0202887 A1    Aug. 9, 2012

Related U.S. Application Data

(62) Division of application No. 11/038,787, filed on Jan. 21, 2005, now Pat. No. 8,222,456.

(60) Provisional application No. 60/538,270, filed on Jan. 23, 2004.

(51) Int. Cl.
    C07C 211/27    (2006.01)
    C07C 279/06    (2006.01)
    C07C 233/77    (2006.01)
    A61K 31/135    (2006.01)
    A61K 31/155    (2006.01)
    A61K 31/16     (2006.01)
    A61K 31/132    (2006.01)

(52) U.S. Cl.
    USPC ........... 564/374; 564/157; 564/236; 564/389; 514/616; 514/634; 514/654; 514/655

(58) Field of Classification Search
    None
    See application file for complete search history.

(56) References Cited

U.S. PATENT DOCUMENTS

| | | |
|---|---|---|
| 3,409,662 A | 11/1968 | Larsen |
| 3,444,156 A | 5/1969 | de Montmollin et al. |
| 3,484,407 A | 12/1969 | Preston |
| 3,829,563 A | 8/1974 | Barry et al. |
| 4,038,416 A | 7/1977 | Mori et al. |
| 4,118,232 A | 10/1978 | Piller et al. |
| 4,252,951 A | 2/1981 | Jackson et al. |
| 4,343,788 A | 8/1982 | Mustacich et al. |
| 4,392,848 A | 7/1983 | Lucas et al. |
| 4,508,639 A | 4/1985 | Camps et al. |
| 4,515,910 A | 5/1985 | Rawls et al. |
| 4,762,899 A | 8/1988 | Shikinami |
| 4,826,829 A | 5/1989 | Eurkart et al. |
| 4,847,353 A | 7/1989 | Watanabe |
| 4,943,624 A | 7/1990 | Regen |
| 5,021,311 A | 6/1991 | Kato et al. |
| 5,071,648 A | 12/1991 | Rosenblatt |
| 5,073,564 A | 12/1991 | Roush et al. |
| 5,077,281 A | 12/1991 | Reinmüller |
| 5,219,965 A | 6/1993 | Valint, Jr. et al. |
| 5,520,910 A | 5/1996 | Hashimoto et al. |
| 5,543,448 A | 8/1996 | Laughner |
| 5,648,070 A | 7/1997 | Brian, III et al. |
| 5,847,047 A | 12/1998 | Haynie |
| 5,856,245 A | 1/1999 | Caldwell et al. |
| 5,874,164 A | 2/1999 | Caldwell |
| 5,912,116 A | 6/1999 | Caldwell |
| 5,967,714 A | 10/1999 | Ottersbach et al. |
| 5,989,295 A | 11/1999 | de la Mettrie et al. |
| 5,994,340 A | 11/1999 | Maiti et al. |
| 6,034,129 A | 3/2000 | Mandeville, III et al. |
| 6,040,251 A | 3/2000 | Caldwell |
| 6,083,602 A | 7/2000 | Caldwell et al. |
| 6,107,397 A | 8/2000 | Blankenburg et al. |
| 6,121,255 A | 9/2000 | Hwu et al. |
| 6,166,172 A | 12/2000 | McCullough et al. |
| 6,290,973 B1 | 9/2001 | Hawkins et al. |
| 6,309,633 B1 | 10/2001 | Ekwuribe et al. |
| 6,399,629 B1 | 6/2002 | Chamberland et al. |
| 6,537,961 B1 | 3/2003 | Koch |
| 6,552,142 B1 | 4/2003 | Meffert et al. |
| 6,686,345 B2 | 2/2004 | Kerwin et al. |
| 6,878,387 B1 | 4/2005 | Petereit et al. |
| 7,173,102 B2 | 2/2007 | DeGrado et al. |
| 7,332,623 B2 | 2/2008 | Wu et al. |
| 7,378,479 B2 | 5/2008 | Tamareselvy et al. |

(Continued)

FOREIGN PATENT DOCUMENTS

| | | |
|---|---|---|
| CH | 520 657 A | 3/1972 |
| CH | 525 898 A | 7/1972 |

(Continued)

OTHER PUBLICATIONS

Database CAPLUS on STN, Acc. No. 1999:626011, Ellis, WO9948461 A2 (Sep. 30, 1999) (abstract).*
Non-Final Office Action for U.S. Appl. No. 10/471,028, filed May 11, 2004, mailed on Oct. 11, 2005.
Final Office Action for U.S. Appl. No. 10/471,028, filed May 11, 2004, mailed on May 8, 2006.

(Continued)

Primary Examiner — Brian J Davis
(74) Attorney, Agent, or Firm — Sterne, Kessler, Goldstein & Fox P.L.L.C.

(57) ABSTRACT

The present invention discloses methods of use of facially amphiphilic polyaryl and polyarylalkynyl polymers and oligomers, including, but not limited to, pharmaceutical uses of the polymers and oligomers as antimicrobial agents and as antidotes for hemorrhagic complications associated with heparin therapy. The present invention also discloses novel facially amphiphilic polyaryl and polyarylalkynyl polymers and oligomers, compositions of the novel polymers and oligomers, including pharmaceutical compositions, and methods of designing and synthesizing the facially amphiphilic polyaryl and polyarylalkynyl polymers and oligomers.

26 Claims, 4 Drawing Sheets

(56) References Cited

U.S. PATENT DOCUMENTS

| | | |
|---|---|---|
| 7,465,820 B2 | 12/2008 | Cunsolo et al. |
| 7,553,876 B2 | 6/2009 | Shaker |
| 7,590,517 B2 | 9/2009 | Doerksen et al. |
| 7,745,662 B2 | 6/2010 | Shaker |
| 7,781,498 B2 | 8/2010 | Krishnan |
| 8,129,566 B2 | 3/2012 | Mousa et al. |
| 8,222,456 B2 | 7/2012 | DeGrado et al. |
| 8,232,428 B2 | 7/2012 | Mousa et al. |
| 8,236,800 B2 | 8/2012 | DeGrado et al. |
| 8,455,490 B2 | 6/2013 | DeGrado et al. |
| 8,507,723 B2 | 8/2013 | Mousa et al. |
| 2001/0044459 A1 | 11/2001 | Jackson et al. |
| 2002/0132797 A1 | 9/2002 | Kerwin et al. |
| 2003/0130454 A1 | 7/2003 | Seya et al. |
| 2004/0052746 A1 | 3/2004 | Tamareselvy et al. |
| 2004/0102941 A1 | 5/2004 | Lopez et al. |
| 2004/0107056 A1 | 6/2004 | Doerksen et al. |
| 2004/0185257 A1 | 9/2004 | DeGrado et al. |
| 2004/0202639 A1 | 10/2004 | DeGrado et al. |
| 2005/0004211 A1 | 1/2005 | Wu et al. |
| 2005/0004212 A1 | 1/2005 | Wu et al. |
| 2005/0287108 A1 | 12/2005 | DeGrado et al. |
| 2006/0024264 A1 | 2/2006 | Kuroda et al. |
| 2006/0041023 A1 | 2/2006 | DeGrado et al. |
| 2006/0041024 A1 | 2/2006 | Shaker |
| 2006/0241052 A1 | 10/2006 | DeGrado et al. |
| 2007/0173752 A1 | 7/2007 | Schonfeldt |
| 2008/0176807 A1 | 7/2008 | DeGrado et al. |

FOREIGN PATENT DOCUMENTS

| | | |
|---|---|---|
| CN | 1181926 A | 5/1998 |
| CN | 1270625 A | 10/2000 |
| CN | 1335303 A | 2/2002 |
| EP | 0 230 539 A2 | 8/1987 |
| GB | 1 324 087 A | 7/1973 |
| GB | 1 566 512 | 4/1980 |
| GB | 2 188 585 A | 10/1987 |
| JP | 52-034935 A | 3/1977 |
| JP | 52-085133 A | 7/1977 |
| JP | 56-123903 A | 9/1981 |
| JP | 59-177558 U | 11/1984 |
| JP | 63-22067 A | 1/1988 |
| JP | 63-108019 A | 5/1988 |
| JP | 2-29436 A | 1/1990 |
| JP | 7-2808 A | 1/1995 |
| JP | 10-505592 T | 6/1998 |
| JP | 11-152329 A | 6/1999 |
| JP | 2001-133975 A | 5/2001 |
| JP | 2002-363261 A | 12/2002 |
| JP | 2003-165805 A | 6/2003 |
| JP | 2004-168802 A | 6/2004 |
| JP | 2004-323688 A | 11/2004 |
| JP | 2007-516741 | 6/2007 |
| WO | WO 87/01591 A2 | 3/1987 |
| WO | WO 90/04401 A1 | 5/1990 |
| WO | WO 93/14146 A1 | 7/1993 |
| WO | WO 95/00547 A1 | 1/1995 |
| WO | WO 95/19974 A2 | 7/1995 |
| WO | WO 96/09285 | 3/1996 |
| WO | WO 97/29160 A1 | 8/1997 |
| WO | WO 97/49413 A1 | 12/1997 |
| WO | WO 98/17625 A1 | 4/1998 |
| WO | WO 99/48461 | 9/1999 |
| WO | WO 00/31183 A1 | 6/2000 |
| WO | WO 00/37541 A1 | 6/2000 |
| WO | WO00/44348 A2 | 8/2000 |
| WO | WO 00/69937 A1 | 11/2000 |
| WO | WO 01/51456 A2 | 7/2001 |
| WO | WO 01/55085 A1 | 8/2001 |
| WO | WO 01/72715 A2 | 10/2001 |
| WO | WO 02/072007 A2 | 9/2002 |
| WO | WO 02/095044 A2 | 11/2002 |
| WO | WO 02/100295 A2 | 12/2002 |
| WO | WO 2003/009807 A2 | 2/2003 |
| WO | WO 2004/014903 A1 | 2/2004 |
| WO | WO 2004/026958 A1 | 4/2004 |
| WO | WO 2004/082634 A2 | 9/2004 |
| WO | WO 2005/028422 A1 | 3/2005 |
| WO | WO 2005/072246 A2 | 8/2005 |
| WO | WO 2005/123660 A2 | 12/2005 |
| WO | WO 2006/042104 A2 | 4/2006 |
| WO | WO 2006/093813 A2 | 9/2006 |
| WO | WO 2006/132647 A2 | 12/2006 |

OTHER PUBLICATIONS

Notice of Allowability or U.S. Appl. No. 10/471,028, filed May 11, 2004, mailed on Sep. 12, 2006.

Non-Final Office Action for U.S. Appl. No. 10/801,951, filed Mar. 17, 2004, mailed on Mar. 29, 2007.

Final Office Action for U.S. Appl. No. 10/801,951, filed Mar. 17, 2004, mailed on Oct. 30, 2007.

Non-Final Office Action for U.S. Appl. No. 10/801,951, filed Mar. 17, 2004, mailed on Jul. 28, 2008.

Shortell, D.B., et al., "Solid-phase approaches toward cyclic oligomers", *Tetrahedron* 57:9055-9065, Elsevier Science Ltd. (2001).

Supplementary Partial European Search Report for European Application No. EP 05 71 1747, mailed on Sep. 24, 2007, The Hague, The Netherlands.

Andersen, J.H., et al., "Lactoferrin and cyclic lactoferrin inhibit the entry of human cytomegalovirus into human fibroblasts," *Antiviral Res.* 51:141-149, Elsevier Science B.V, (2001).

Appella, D.H, et al., "Formation of Short, Stable Helices in Aqueous Solution by βAmino Acid Hexamers," *J. Am. Chem. Soc.* 121:2309-2310, American Chemical Society (1999).

Arnt, L. and Tew, G.N., "New Poly(phenyleneethynylene)s with Cationic, Facially Amphiphilic Structures," *J. Am. Chem. Soc.* 124:7664-7665, American Chemical Society (2002).

Arnt, L. and Tew, G.N., "Phenylene Ethynylene Polymers with Amphiphilic Structures," *Polymer Preprints* 43:445, Division of Polymer Chemistry, Inc., American Chemical Society (2002).

Arnt, L., et al., "Amphiphilic Secondary Structure in Phenylene Ethynyienes", *Polymer Preprints* 44:1266-1267, Division of Polymer Chemistry, Inc., American Chemical Society (Mar. 2003).

Barany, G., et al, "Solid-phase peptide synthesis: a silver anniversary report," *Int. Protein Res.* 30:705-739, Munksgaard International Publishers (1987).

Barron, A.E. and Zuckerman, R.N., "Bioinspired polymeric materials: in-between proteins and plastics," *Curr. Opin. Chem. Biol.* 3:681-687, Current Biology Ltd. (1999).

Bastian A. and Schafer, H., "Human α-defensin 1 (HNP-1) inhibits adenoviral infection in vitro," *Regul. Pept.* 101:157-161, Elsevier Science B.V. (2001).

Belaid, A., et al., "In Vitro Antiviral Activity of Dermaseptins Against Herpes Simplex Virus Type 1," *J. Med. Virol.* 66:229-234, Wiley-Liss, Inc. (2002).

Berresheim, A.J., et al., "Polyphenylene Nanostructures," *Chem. Rev.* 99:1747-1785, American Chemical Society (1999).

Bjørnholm, T., et al., "Self-Assembly of Regioregular, Amphiphilic Polythiophenes into Highly Ordered Π-Stacked Conjugated Polymer Thin Films and Nanocircuits," *J. Am. Chem. Soc.* 120:7643-7644, American Chemical Society (1998).

Boman, H.G., "Innate immunity and the normal microflora," *Immunol. Rev.* 173:5- 16, Munksgaard International Publishers (2000).

Boman, H.G., et al., "Cell-free immunity in Cecropia. A model system for antibacterial proteins," *Eur. J. Biochem.* 201:23-31, Springer International (1991).

Breitenkamp, R.B. and Tew, G.N., "Aggregation Studies of Novel, Facially Amphiphilic Phenylene Ethynylenes," *Polymer Preprints* 44:673-674, Division of Polymer Chemistry, Inc., American Chemical Society (Mar. 2003).

Broekaert, W.F., et al., "An automated quantitative assay for fungal growth inhibition," *FEMS Microbiol. Lett.* 69:55-60, Elsevier (1990).

(56) References Cited

OTHER PUBLICATIONS

Calzia, K.J. and Tew, G.N., "Copolymers Containing Metal Binding Ligands for use in Supramolecular Materials: Toward Metal Induced Reversible Networks," *Polymer Prepr.* 43:408-409, American Chemical Society (2002).

Chen, J., of al., "Development of Protegrins for the Treatment and Prevention of Oral Mucositis: Structure-Activity Relationships of Synthetic Protegrin Analogues," *Biopolymers* 55:88-98, John Wiley & Sons, Inc. (2000).

Cole, A.M., et al., "Retrocyclin: A primate peptide that protects cells from infection by T-and M-tropic strains of HIV-1," *Proc. Natl. Acad. Sci USA* 99:1813-1818, National Academy of Sciences (2002).

Debono, M. and Gordee, R.S., "Antibiotics that Inhibit Fungal Cell Wall Development," *Annu. Rev. Microbiol.* 48:471-497, Annual Reviews (1994).

DeGrado, W.F., "Design of Peptides and Proteins," *Adv. Prot. Chem.* 39:51-124, Academic Press, Inc. (1988).

DeGrado, W.F., et al., Kinetics and Mechanism of Hemolysis Induced by Melittin and by a Synthetic Melittin Analogue, *Biophys. J.* 37:329-338, The Rockefeller University Press (1982).

DeGrado, W.F., et al., "Design, Synthesis and Characterization of a Cytotoxic Peptide with Melittin-Like Activity," *J. Am -Chem. Soc.* 103:679-681, American Chemical Society (1981).

DeLucca, A.J. and Walsh, T.J., "Antifungal Peptides: Novel Therapeutic Compunds against Emerging Pathogens", *Antimicob. Agents Chemother.* 43:1-11, American Sosiety for Microbiology (1999).

Dempsey, C.E., "The actions of melittin on membranes," *Biochim. Biophys. Acta* 1031:143-161, Elsevier Science Publishers B.V. (1990).

Diness, V. and Østergaard, P.B., "Neutralization of a Low Molecular Weight Heparin (LHN-1) and Conventional Heparin by Protamine Sulfate in Rats," *Thromb. Haemost.* 56:318-322, F.K. Schattauer Verlag GmbH (1986).

Edwards, J.R., et al., "In Vitro Antibacterial Activity of SM-7338, a Carbapenem Antibiotic with Stability to Dehydropeptidase I," *Antimicrob. Agents Chemother.* 33:215-222, American Society for Microbiology (1989).

Egal, M., et al., "Antiviral effects of synthetic membrane-active peptides on Herpes Simplex Virus, Type 1," *Int. J. Antimicrob. Agents* 13:57-60, Elsevier Science B.V. (1999).

Ganz, T., et al., "Defensins," *Eur. J. Haematol.* 44:1-8, Munksgaard International Publishers Ltd. (1990).

Ganz, T., et al., "Defensins. Natural Peptide Antibiotics of Human Neutrophils," *J. Clin. Invest* 76:1427-1435, The American Society for Clinical Investigation, Inc. (1985).

Gazit, E., et al., "Interaction of the Mammalian Antibacterial Peptide Cecropin P1 with Phospholipid Vesicles," *Biohemistry* 34:11479-11488, American Chemical Society (1995).

Gellman, S.H., "Foldamers: A Manifesto," *Acc. Chem. Res.* 31:173-180, American Chemical Society (1998).

Gennaro, R. and Zanetti, M., "Structural Features and Biological Activities of the Gethelicidin-Derived Antimicrobial Peptides," *Biopoiymers* 55:31-49, John Wiley & sins. inc. (2000).

Hamuro, Y., et al., "De Novo Design of Antibacterial β-Peptides," *J. Am. Chem. Soc.* 121:12200-12201, American Chemical Society (1999).

Hancock, R.E.W. and Lehrer, R., "Cationic peptides: a new source of antibiotics," *Trends Biotechnol* 16:82-88, Elsevier Science Publishers B.V. (1998).

Haynie, S.L., et al., "Antimicrobial Activities of Amphiphilic Peptides Covalently Bonded to a Water-Insoluble Resin," *Antimicrob. Agents Chemother.* 39:301-307, American Society for Microbiology (1995).

Hirsh, J. and Levine, M.N., "Low Molecular Weight Heparin," *Blood* 79:1-17, The American Society of Hematology (1992).

Houseman, B.T. and Mrksich, M., "The microenvironment of immobilized Arg-Gly-Asp peptides is an important determinant of cell adhesion," *Biomaterials* 22:943-955, Elsevier Science (2001).

Hsu, S-H., and Chen, W-C., "Improved cell adhesion by plasma-induced grafting of L-lactide onto polyurethane surface," *Biomaterials* 21:359-367, Elsevier Science (2000).

Javadpour, M.M., et al., "De Novo Antimicrobial Peptides with Low Mammalian Cell Toxicity," *J. Med. Chem.* 39:3107-3113, American Chemical Society (1996).

Kandrotas, R.J., "Heparin Pharmacokinetics and Pharmacodynamics," *Clin. Pharmacokinet.* 22:359-374, Adis International Ltd. (1992).

Kim, J. and Swager, T.M., "Control of conformational and interpolymer effects in conjugated polymers," *Nature* 411:1030-1034, Nature Publishing Group (2001).

Kim, J., et al., "Structural Control in Thin Layers of Poly(p-phenyleneethynylene)s: Photophysical Studies of Langmuir and Langmuir-Blodgett Films," *J. Am. Chem. Soc.* 124:7710-7718, American Chemical Society (2002).

Klok, H-A., et al., "Self-Assembling Biomaterials," *Polymer Prepr.* 39:166-167, American Chemical Society (1998).

Kochendoerfer, G.G., et al., "Total Chemical Synthesis of the Integral Membrane Protein Influenza A Virus M2: Role of its C-Terminal Domain in Tetramer Assembly", *Biochemistry* 38:11905-11913, American Chemical Sosiety (1999).

Landon; C. at al., "Solution structure of drosomycin, the first inducible antifungal protein from insects," *Protein Sci.* 6:1878-1884, Cambridge University Press (1997).

Liu, D. and DeGrado, W.F., "De Novo Design, Synthesis, and Characterization of Antimicrobial β-Peptides," *J. Am. Chem. Soc.*, 123:7553-7559, American Chemical Society (2001).

Maloy, W.L. and Kari, U.P., "Structure-Activity Studies on Magainins and Other Host Defense Peptides," *Biopolymers* 37:105-122, John Wiley & Sons, Inc. (1995).

Margel, S., et al., "Peptide, protein, and cellular interactions with self-assembled monolayer model surfaces," *J. Biomed. Mater. Res.* 27:1463-1476, John Wiley & Sons, Inc. (1993).

Massia, S.P., and Hubbell, J.A., "An RGD Spacing of 440 nm Is Sufficient for Integrin $\alpha_v\beta_3$-mediated Fibroblast Spreading and 140 nm for Focal Contact and Stress Fiber Formation," *J. Cell Biol.* 114:1089-1100, Rockefeller University Press (1991).

Massia, S.P. and Hubbell, J.A., "Covalent Surface Immobilization of Arg-Gly-Asp-and Tyr-Ile-Gly-Ser-Arg-Containing Peptides to Obtain Well-Defined Cell-Adhesive Substrates," *Anal. Biochem.* 187:292-301, Academic Press (1990).

Massia, S.P. and Stark, J., "Immobilized RGD peptides on surface-grafted dextran promote biospecific cell attachment," *J. Biomed. Mater. Res.* 56:390-399, Wiley Interscience (2001).

Merrifield, E.L., et al., D-Enantiomers of 15-residue cecropin A-melittin hybrids, *Int. J. Pept. Protein Res.* 46:214-220, John Wiley & Sons, Inc. (1995).

Merrifield, R.B., et al., "Design and synthesis of antimicrobial peptides," *Ciba Found. Symp.* 186:5-26 (1994).

Merrifield, R.B., et al., "Retro and retroenantio analogs of cecropin-melittin hybrids," *Proc. Natl. Acad. Sci. USA* 92:3449-3453, National Academy of Sciences (1995).

Mrksich, M., "Tailored substrates for studies of attached cell culture," *Cell. Mol. Life Sci.* 54:653-662, Birkhauser Verlag (1998).

Mrksich, M. and Whitesides, G.M., "Using Self-Assembled Monolayers to Understand the Interactions of Man-Made Surfaces with Proteins and Cells," *Annu. Rev. Biophys. Biomol. Struct* 25:55-78, Annual Reviews (1996).

Muir, T.W., et al., "Protein Synthesis by Chemical Ligation of Unprotected Peptides in Aqueous Solution," *Methods Enzymol.* 289:266-298, Academic Press (1997.)

Nelson, J.C., et al., "Solvophobically Driven Folding of Nonbiological Oligomers," *Science* 277:1793-1796, American Association for the Advancement of Science (1997).

Oren, Z., and Shai, Y., "Mode of Action of Linear Amphipathic α-Helical Antimicrobial Peptides," *Biopolymers* 47:451-463, John Wiley & Sons, Inc. (1998).

Peggion, E., et al., "Conformation and Interactions of Bioactive Peptides from Insect Venoms: The Bombolitins," *Biopolymers* 43:419-431, John Wiley & Sons, Inc. (1997).

Peskin, E., "Plasma processing of biomaterials," *J. Biomater. Sci. Polymer Edu.* 4:45-60, VSP (1992).

(56) References Cited

OTHER PUBLICATIONS

Porter, E.A., at al., "Non-haemolytic β-amino-acid oligomers," *Nature* 404:565, Macmillan Magazines Ltd. (2000).
Pouny, Y., et al., "Interaction of Antimicrobial Dermaseptin and Its Fluorescently Labeled Analogues with Phospholipid Membranes," *Biochemistry* 31:12416-12423, American Chemical Society (1992).
Pralle, M.U., et al., "Self Assembled Phenylene Vinylene Materials," *Microsc. Microanal.* 8(*Suppl. 2*):318, Fig. 1, Cambridge University Press (2002).
Prince, R.B., et al., "Cooperative Conformational Transitions in Phenylene Ethynylene Oligomers: Chain-Length Dependence," *J. Am. Chem. Soc.* 121:3114-3121, American Chemical Society (1999).
Prince, R.B., et al., "Twist Sense Bias Induced by Chiral Side Chains in Helically Folded Oligomers," *Angew. Chem. let. Ed.* 39:228-230, Academic Press (2000).
Scherf, U., "Oligo—and Polyarylenes, Oligo—and Polyarylenevinylenes," *Top. Curr. Chem.* 201:163-222, Springer-Verlag (1999).
Seebach, D. and Matthews, J.L., "β-Peptides: a surprise at every turn," *Chem. Commun.* 21:2015-2022, Chemical Society (1997).
Sinha, S., et al., "NP-1, a Rabbit α-Defensin, Prevents the Entry and Intercellular Spread of Herpes Simplex Virus Type 2," *Antimicrob. Agents Chemother.* 47:494-500, American Society of Microbiology (Feb. 2003).
Steiner, H., et al., "Sequence and specificity of two antibacterial proteins involved in insect immunity," *Nature,* 292:246-248, Macmillan Journals Ltd. (1981).
Stigers, K.D., et al., "Designed molecules that fold to mimic protein secondary structures," *Curr Opin. Chem. Bio.* 3:714-723, Current Biology Ltd. (1999).
Stupp, S.I., et al., "Functionalized Supramolecular Materials," *Polymer* 39:4505-4508, Elsevier Science (1998).
Tang, Y.-Q., et al., "A Cyclic Antimicrobial Peptide Produced in Primate Leukocytes by the Ligation of Two Truncated α-Defensins," *Science* 286:498-502, American Association for the Advancement of Science (1999).
Tew, G.N. and Stupp S.I., "Multifunctional Supramolecular Materials", *ACS Symp. Ser.* 704:218-226, American Chemical Society (1998).
Tew. G.N., et al., "*De novo*design of biomimetic antimicrobial polymers", *Proc. Natl. Acad. Sci. USA* 99:5110-5114, National Academy of Sciences (2002).
Tew, G.N., et al, "Amphiphilic Phenylene Ethynylenes." *Polymer Preprints* 44:45 Division of Polymer Chemistry, Inc., American Chemical Society (Aug. 2003).
Tew, G.N., et al, "Simple Facially Amphiphilic as Peptide Mimics", 224th *ACS National Meeting*, Boston, MA, Aug. 18-22, 2002, Abstract 4, Americal Chemical Sosiety (2002).
Tew, G.N., et al, "Supramolecular Materials with Electroactive Chemical Functions", *Angew, Chem. Int. Ed.* 39:517-521, Wiley-VCH (2000).
Tiller, J.C., et al., "Designing surfaces that kill bacteria on contact", *Proc. Natl. Acad. Sci. USA* 98:5981-5985, National Academy of Sciences (2001).
Tossi, A., et at., "Amphipathic, α-Helical Antimicrobial Peptides," *Biopolymers* 55:4-30, John Wiley & Sons, Inc. (2000).
Turpie, A.G.G., "Pharmacology of the low-molecular-weight heparins," *Am. Heart J.* 135:S329-S335, Mosby, Inc. (1998).
Van Ryn-McKenna, J., et al., "Neutralization of Enoxaparine-Induced,Bleeding by Protamine Sulfate," *Thromb. Haetnost.* 63:271-274, Schattauer (1990).
Wachinger, M., et al., "Antimicrobial peptides melittin and cecropiri inhibit replication of human immunodeficiency virus 1 by suppressing viral gene expression "*J. Gen. Virol.* 79:731-740, The Society for General Microbiology (1998).
Wakefield T.W., et al., A [+18RGD]Protamine Variant for Nontoxic and Effective Reversal of Conventional Heparin and Low-Molecular-Weight Heparin Anticoagulation *J. Surg. Res* 63:280-280, Academic Press Inc. (1996).

Wong, P.C., at al., "Nonpeptide Factor Xa Inhibitors: I. Studies with SF303 and SK549, a New Class of Potent Antithrombotics", *J. Pharmacol. Exp. Therap* 292:351-357, American Society for Pharmacology and Experimental Therapeutics (200).
Woo, G.L.Y. et al "Synthesis and characterization of a novel biodegradable antimicrobial polymer," *Biomaterials* 21:1235-1246, Elsevier Science Ltd (2000).
Zasloff, M., "Antibiotic peptides as mediators of innate immunity," *Curr. Opin. Immunol.* 4:3-7, Current Biology Ltd. (1992).
Zasloff, M., "Antimicrobial peptides of multicellular organisms,'" *Nature* 415:389-395, Macmillan Magazines Ltd. (2002).
Zasloff, M., "Reconstructing one of nature's designs" *Trends Pharmacol. Sci.* 21:236-238, Elsevier Science Ltd. (2000).
Zhang, L. et at., "Contribution of Human α-Defensin 1, 2, and 3 to the Anti-HIV-1 Activity of CD8 Antiviral Factor," *Science* 298:995-1000, American Association for the Advancement of Science (2002).
Zhao, C., et al., "Identificaion of a new member of the protegnn amily by cDNA cloning," *FEBS Lett.* 346:285-288, Elsevier B.V. (1994).
U.S. Appl. No. 10/801,951, DeGrado, W., et al., filed Mar. 17, 2004 (Now published as U.S. Patent Application Publication No. 2006/0041023 A1)
International Search Report for International Patent Application No. PCT/US05/01885, maied Apr. 6, 2006.
United States Patent Application No. 11/361,050, DeGrado et al., filed Feb. 24, 2006 (Now Published as U.S. Patent Application Publication No. US 2006/0241052 A1).
Rusanov, A., et al., "The use of palladium-catalysed cross-coupling for the synthesis of polymers incorporating vinylene and ethynylene groups", *Russian Chemical Reviews* 66:1053-1068, Russian Academy of Science and Turpion Ltd., Russia (1997).
Ryn-McKenna, J., et al., "Neutralization of enoxaparine-induced bleeding by protamine sulfate," *Thromb. Haemost.* 63:271-274, Schattauer, Germany (1990).
Scherf, U., "Oligo- and polyarylenes, oligo- and polyarylenevinylenes," in *Carbon Rich Compounds II: Macrocyclic Oligoacetylenes and Other Linearly Conjugated Systems, Topics in Current Chemistry*, de Meijere, A., ed. vol. 201, 163-222 Springer-Verlag, Germany (1999).
Stevens, M., Polymer Chemistry: An Introduction, 3rd ed., pp. 409-424, Oxford University Press, New York (1999).
Tecilla, P., et al., "Hydrogen-bonding self-assembly of multichromophore structures," *J. Am. Chem. Soc.* 112:9408-9410, American Chemical Society, United States (1990).
Turner, P., et al., "Polybenzamide mustards: structure activity relationships for DNA sequence-specific alkylation," *Anti-Cancer Drug Design* 14:61-70, Oxford University Press, United Kingdom (1999).
Turner, P., et al., "Role of DNA minor groove alkylation and DNA cross-linking in the cytotoxicity of polybenzamide mustards," *Anti-Cancer Drug Design* 15:245-253, Oxford University Press, United Kingdom (2000).
Advisory Action mailed on Apr. 7, 2010, in U.S. Appl. No. 10/471,029 inventors DeGrado, et al., filed Jun. 7, 2004.
Advisory Action mailed on Apr. 18, 2011, in U.S. Appl. No. 10/471,029 inventors DeGrado, et al., filed Jun. 7, 2004.
Advisory Action mailed on Jun. 9, 2009, in U.S. Appl. No. 10/801,951, DeGrado, et al., filed Mar. 17, 2004.
Office Action mailed on Feb. 24, 2010, in U.S. Appl. No. 11/361,050, inventors DeGrado, et al., filed Feb. 24, 2006.
Advisory Action mailed on Feb. 14, 2011, in U.S. Appl. No. 11/361,050, inventors DeGrado, et al., filed Feb. 24, 2006.
English language abstract of Borshe, W., "Reactivity of the Side Chains in the Ring-nitrated Homologs of Benzene," in *Justus Liebigs. Ann.*, vol. 386, pp. 351-373 (1912), Database CAPLUS on STN, Accession No. 1912:7297, 2 pages.
Patent Abstract of Japan, English Language abstract for JP 52-085133 A, Patent & Utility Model Gazette DB, Japanese Patent Office, 2 pages (1977).
Patent Abstract of Japan, English Language abstract for JP 56-123903 A, Patent & Utility Model Gazette DB, Japanese Patent Office, 2 pages (1981).
Patent Abstract of Japan, English Language abstract for JP 59-177558 A, Patent & Utility Model Gazette DB, Japanese Patent Office, 2 pages (1984).

(56) References Cited

OTHER PUBLICATIONS

Esp@cenet Database, English language abstract of JP 7-2808 A, espacenet, European Patent Office, 2 pages (1995).
Esp@cenet Database, English language abstract of JP 10-505592 A, espacenet, European Patent Office, 1 page (1998).
Esp@cenet Database, English language abstract of WO 00/69937 A1, espacenet, European Patent Office, 1 page (2000).
Esp@cenet Database, English language abstract of CN 1335303 A, espacenet, European Patent Office, 1 page (2002).
Patent Abstract of Japan, English Language abstract for JP 2001-133975 A, Patent & Utility Model Gazette DB, Japanese Patent Office, 2 pages (2001).
U.S. Appl. No. 10/471,028, DeGrado, et al., filed May 11, 2004 (now U.S. Patent No. 7,173,102).
U.S. Appl. No. 10/471,029, DeGrado, et al., filed Jun. 7, 2004 (now U.S. Published Patent Appl. No. 2004-0202639 A1).
U.S. Appl. No. 11/980,785, DeGrado, et al., filed Oct. 31, 2007 (now U.S. Patent No. 8,236,800 B2).
Bradley, J, S., and Scheid W.M., "The Challenge of Penicillin Resistant *Streptococcus pneumoniae* Meningitis: Current Antibiotic Therapy in the 1990s," *Clin. Infect. Dis. 24*(Suppl. 2):S213-221, University of Chicago Press (1997).
Butler, J.C., et al., "The Continued Emergence of Drug-Resistant *Streptococcus Pneumoniae* in the United States: An Update, from the Centers for Disease Control and Prevention's Pneumococcal Sentinel Surveillance System," *J. Infect. Dis. 174*:986-993, University of Chicago Press (1996).
Dermer, G. B., "Another Anniversary for the War on Cancer," *Bio/Technology 12:320*, Nature Publishing Group, United Kingdom (1994).
Freshney, R.I., "Culture of Animal Cells: A Manual of Basic Technique." pp. 4, Alan R. Liss, Inc., New York, NY (1983).
Gura, T., "Systems for Identifying New Drugs Are Often Faulty," *Science 278*:1041-42, American Association for the Advancement of Science, United States (1997).
Hiramatsu, K., et at., "Methicillin-resistant *Staphylococcus aureus* clinical strain with reduced vancomycin susceptibility," *J. Antimicrob. Chemother. 40*:135-146, Oxford University Press.
Höger, S., et al., "Synthesis and Properties of Shape-Persistent Macrocyclic Anmhiphiles with Switchable Amphiphilic Portions," *Chem. Bur. J. 4*:2423-2434, Wiley~VCH Verlag GmbH, Germany (1998).
Hwu, J. R., et al., "Cephalosporin 3'-Phloroglucicle Esters and 7-(Phloroglucidamido) cephalosporins as Novel Antibacterial Agents," *J. Med. Chem. 40*:3434-3441, American Chemical Sosiety, United States (1997).
Lyytikäinen, 0., et at, "Outbreak caused by two multi-resistant *Acihetobacter baumannii*clones in a burns unit: emergence of resistance to imipenem," *J. Hosp. Infect. 31*:41-54, W.B. Saunders for the Hospital Infection Society, United Kingdom (1995).
"Infection", Dorland's Medical Dictionary, Elsevier (online 20007).
Montecalvo, M. M., et al., "Outbreak of Vancomyoln-, Ampicillin-, and Aminoglycdside- Resistant *Enterococcus faeciurn* Bacteremia in an Adult Oncology Unit," *Antimicro, Agents Chemother 38*:1363-1367, American Society for Microbiology (1994).
PolyMedix, "Low Molecular Weight Heparin Antagonist", website http://www.polymedix.com/03_03_low-molecular.htm, accessed on Apr. 27 2007, pp. 1-2.
Threlfall, E.J, et al., "Increasing spectrum of resistance in multiresistant *Salmonella typhimurium*," *Lancet 347*:1053-1054, Lancet Publishing Group (1996).
Zhang, L., et al., "Contribution of Human α-Defensin 1, 2, and 3 to the Anti-HIV-1 Activity of CD8 Antiviral Factor," *Science 298*:995-1000, American Association for the Activity Advancement of Science (2002).
Office Action mailed on Apr. 13, 2010, in U.S. Appl. No. 10/801,951, inventors DeGrado et al., filed Mar. 17, 2004.
Office Action mailed Mar. 25, 2010, in U.S. Appl. No. 10/801,951, inventors DeGrado et at., filed Mar. 17, 2004.
Office Action mailed on Nov. 17, 2009, in U.S. Appl. No. 10/471,029, inventors DeGrado et al., filed Jun. 7, 2004.
Office Action mailed on Jul. 27, 2010, in U.S. Appl. No. 10/471,029, inventors DeGrado et al., filed Jun. 7 2004.
International Search Report for International Application No. PCT/US02/06899, mailed on Jul. 8, 2002, ISA/US, Virginia, USA.
International Search Report for International Application No. PCT/US02/22043, mailed on Jan. 13, 2003, ISA/US, Virginia, USA.
English language abstract for JP 11-152329, dated Jun. 8, 1999, espacenet, European Patent Office.
CAS Registry No. 495410-77-0; Entry date: Feb. 27, 2003.
CAS Registry No. 87774-34-3; Entry date: Nov. 16, 1984.
CAS Registry No. 92-06-8; Entry date: Nov. 16, 1984.
International Search Report for International Patent Application No. PCT/US04/08155, mailed Sep. 1, 2005, ISA/US, Virginia, USA.
Supplementary European Search Report for European Application No. 05 85 7895, The Hague, The Netherlands, search completed on Sep. 4, 2008.
International Search Report for International Application No. PCT/US06/06487, mailed on Sep. 27, 2007, ISA/US, Virginia, USA.
Office Action mailed on Jun. 2, 2009 in U.S. Appl. No. 10/801,951, inventors DeGrado et al., filed Mar. 17, 2004.
Supplementary Partial European Search for European Application No. EP 04 74 9404, completed on Mar. 27, 2009, The Hague, The Netherlands.
Office Action mailed on Sep. 9, 2010 in U.S. Appl. No. 11/361,050, inventors DeGrado et al., filed Feb. 24, 2006.
Office Action mailed on Jan. 3, 2011, in U.S. Appl. No. 10/471,029, inventors DeGrado el al., filed Jun. 7, 2004.
Bunz, U.H.F., "Poly(aryleneethynylenes)s: Syntheses, Properties, Structues and Applications," *Chem. Rev. 100*:1605-1644, American Chemical Society (2000).
Weder, C.W., et al., "Effect of the Solid State Structure on Third-Order Nonlinear Optical Response of Poly(2,5-dialkoxy-*p*-phenyleneethynylene)s," *J. Phys. Chem. 100*:18931-18936, American Chemical Society (1996).
Arnt, I,. et al., "Nonhemolytic Abiogenic Polymers as Antimicrobial Peptide Mimics", *J. Polym. Sci. Part A 42*:3860-3864 (Published online Jun. 2004).
Baker, M.A, et al,, "Anticancer Efficacy of Magainin2 and Analogue Peptides," *Cancer Res. 53*:3052-3057 (1993).
Brooks, B.R., et al., "CHARMM: A Program for Macromolecular Energy, Minimization, and Dynamics Calculations," *J. Comp. Chem. 4*:187-217, John Wiley & Sons (1983).
Car, R., and Parrinello, M., "Unified Approach for Molecular Dynamics and Density-Functional Theory," *Phys. Rev. Lett. 55*:2471-2474, American Physical Society (1985).
Cruciani, R.A., et al "Antibiotic magainins exert cycloytic activity against transformed cell lines through channel formation," *Proc. Natl. Acad. Sci. USA 88*:3792-3796 (1991).
Ge, P.-I., at al.,"Structural Characterization of a Cyclohexamieric *meta-* Phenyleneethynylene Made by Alkyne Metathesis with In Situ Catalysts," *Angew. Chem. Int. Ed. 39*:3607-3610, Wiley-VCH Verlag GmbH (2000).
Hamuro, Y., et al., "Novel Folding Patterns in a Family of Oligoanthranilamides: Non-Peptide Oligomers That Form Extended Helical Secondary Structures" *J. Am. Chem. Soc. 119*:10587-10593, American Chemical Society (1997).
Kelly, T.J., et al., "Emission Rates of Formaldehyde from Materials and Consumer Products Found in California Homes," *Environ, Sci. Technol, 33*:81-88, American Chemical Society (1999).
Kim, J., et al., "Nanoscale Fibrils and Grids: Aggregated Structures from Rigid-Rod Conjugated Polymers," *Macromolecules 32*:1500-1507, American Chemical Society (1999).
Liu, D. et al., "Nontoxic Membrane-Active Antimicrobial Arylamide Oligomers" *Angew. Chem. Int. Ed. Engl. 43*:1158-1162, Verlag Chemie (Feb. 2004).
Maloy, W.L. and Kari, U.P., "Structure-Activity Studies on Magainins and Other Host Defense Peptides", *Biopolymers 37*:105-122, John Wiley & Sons, Inc. (1995).
Martin, M.G., and Siepmann, J.I., "Novel Configurational-Bias Monte Carlo Method for Branched Molecules. Transferable Poten-

(56) References Cited

OTHER PUBLICATIONS tials for Phase Equilibria. 2. United-Atom Description of Branched Alkanes," *J. Phys. Chem. B 103*:4508-4517, American Chemical Society (1999).
Nelson, J.C., et al., "Solvophobically Driven Folding of Nonbiological Oligomers," *Science 277*:1793-1796, American Association for Advancement of Science (1997).
Okumura, K., et al., "C-terminal domain of human CAP18 antimicrobial peptide induces apotosis in oral squamous cell carcinoma SAS-H1 cells," *Cancer Lett. 212*:185-194 (Aug. 2004).
Papo, N. and Shai, Y., "New Lytic Peptides Based on the D,L-Amphipathic Helix Motif Preferentially Kill Tumor Cells Compared to Normal Cells," *Biochemistry 42*:9346-9354 (Aug. 2003).
Papo, N. et al. "Suppression of Human Prostate Tumor Growth in Mice by a Cytolytic D-, L-Amino Acid Peptide: Membrane Lysis, Increased Necrosis, and Inhibition of Prostate-Specific Antigen Secretion," *Cancer Res. 64*:5779-5786 (Aug. 2004).
Patch, J.A., and Barron, A.E., "Helical Peptoid Mimics of Magainin-2 Amide," *J. Am. Chem. Soc. 125*:12092-12093 (Published online Sep. 2003).
Porter, E.A., et al. "Mimicry of Host-Defense Peptides by Unnatural Oligomers: Antimicrobial β-Peptides," *J. Am. Chem. Soc. 124*:7324-7330 (2002).
Röthlisberger, U., et al., "The torsional potential of perfluoro *n*-alkanes: A density functional study," *J. Chem. Phys. 104*:3692-3700, American Institute of Physics (1996).
Samson, N., et al., "Relationship Between Synthesis and Mechanical Properties of New Polyurea Materials," *J. Appl. Polym. Sci. 65*:2265-2280, John Wiley & Sons Inc., (1997).
Atwell, G., at al., "Synthesis, DNA interactions and biological activity of DNA minor groove targeted polybenzamide-linked nitrogen mustards", *Bioorg. Med. Chem. 3*:679-691, Pergamon Press, United Kingdom (1995).
Borshe, W., "Über die Reaktionsfähigkeit der Seitenketten in den kernitrierten Homologen des Benzols," in *Justus Liebig's Annalen Der Chemie*, vol. 386, pp. 351-373, C.F. Winter'sche Verlagshandlung, Germany (1912).
Chapman, R., et al., "Small molecule modulators of HIV Rev/Rev responce element interaction indentified by random screening," *Antiviral Res. 54*:149-162, Elsevier, Netherlands (2002).
Decosterd, L. et al., "High-performance liquid chromatography blood flow marker p-aminohippuric acid (PAH) and its improves Pah clearance measurements." *J. Chromatogr. B. 703*:25-36, Elsevier, Netherlands (1997).
Guillemot, D., et al., "Low Dosage and Long Treatment Duration of β-Lactam," *JAMA 279*:365-370, American Medical Association, United States (1998).
Haugwitz, R., et al., "Antiparisitic agents. 6. Synthesis and anthelmintic activities of novel isothicyanatophenyl-1,2,4-oxadiazoles," *J. Med. Chem. 28*:1234-1241, American Chemical Society, United States (1985).
Lathers, C., "Clinical Pharmacology of Antimicrobial Use In Humans and Animals," *J. Clin. Pharmacol. 42*:587-600, Sage Science Press, United States (2002).
Markovac, A. and LaMontagne, M., "Antimalarials. 12. Preparation of carbon isosteres of selected 4-pyridine methanols as suppressive antimalarials," *J. Med. Chem. 23*:1198-1201, American Chemical Society, United States (1980).
Monroe, S. and Polk, R., "Antimicrobial use and bacterial resistance," *Curr. Opin. Microbiol. 3*:496-501, Elsevier Science Ltd., Netherlands (2000).
Nicolaus, B., "Symbiotic Approach to Drug Design," in *Decision Making in Drug Research*, pp. 173-186, Gross F., ed., Raven Press, New York (1983).
Ridgway, G., "Treatment of chlamydial genital infection,"*J. Antimicrob. Chemother. 40*:311-314, The British Society for Antimicrobial Chemotherapy, United Kingdom (1997).
Atwell, G. and Cain, B., "Potential Antitumor Agents. 13. Bisquaternary Salts," *J. Med. Chem. 16*:673-678, American Chemical Society United States (1973).

Denny, W., et al., "Potential Antitumor Agents. 36. Quantitative Relationships Between Experimental Antitumor Activity, Toxicity, and Structure for the General Class of 9-Anilinoacridine Antitumor Agents," *J. Med. Chem, 25*:276-315, American Chemical Society, United States (1982).
Hudson, J. and Towers, G., "Antiviral properties of acetylenes and thiophenes," *Bioactive Molecules 7*:315-338, Elsevier, Amsterdam (1988).
Hudson, J., et al., "Photoactive antiviral and cytotoxic activities of synthetic thiophenes and their acetylenic derivatives," *Chemosphere 19*:1329-1343, Pergamon Press, United Kingdom (1989).
Lin, C.F, et al.,"Cytotoxicities, cell cycle, and caspase evaluations of 1,6-diaryl-3(Z)-hexen-1,5-diynes, 2-(6-aryl-3(Z)-hexen-1,5-diynyl)anilines and their derivatives," *Bioorg. Med. Chem. 13*:3565-3575, Elsevier, England (2005).
STN Database CAPLUS, "1,2-bis[2-(2,6-difluorophenyl) ethynyl]-benzene" Registry Number 27286-86-8, entered Nov. 16, 1984.
STN Database CAPLUS, "2,6-bis(2-phenylethynyl)-phenol" Registry No. 478551-27-8, entered Jan. 9, 2003.
STN Database CAPLUS, "3,5-bis(2-phenylethynyl)-benzoic acid methyl ester," Registry No. 272128-90-2, entered Jun. 22, 2000.
STN Database CAPLUS, "1,4-dibromo-2,5-bis[2-(2-bromophenyl) ethynyl]-benzene," Registry No. 625389-87-9, entered Dec. 10, 2003.
STN Database CAPLUS, "4,4'-(1,2-phenylenedi-2,1-ethynediyl)bis [2,3,5,6-tetrafluoropyridine], "Registry No. 459457-30-8, entered Oct. 7, 2002.
STN Database CAPLUS, "1,2,4,5-tetrafluoro-3,6-bis[2-(4-fluorophenyl)ethynyl]-benzene" Registry No. 332148-91-1, entered Apr. 24, 2001.
STN Database CAPLUS, "1,4-bis[2-(2,3,4,5,6-pentafluorophenyl) ethynyl]-benzene" Registry No. 258506-15-9, entered Mar. 8, 2000.
Vippagunta, S., et al., "Crystalline solids," *Adv. Drug Deliv. Rev. 48*:3-26, Elsevier Science Publishers, B.V, Netherlands (2001).
Unverified machine generated English translation of Swiss Patent No. CH 520 657 A, published Mar. 31, 1972.
Unverified machine generated English translation of Swiss Patent No. CH 525 989 A, published Jul. 31, 1972.
Non-Final Office Action mailed Nov. 10, 2011 in U.S. Appl. No. 11/980,785, inventors Degrado, W., et al., filed Oct. 31, 2007.
Notice of Allowance mailed Mar. 6, 2012 in U.S. Appl. No. 11/980,785, inventors DeGrado, W., et al., filed Oct. 31, 2007.
Sekaran, G., et al., "Physicochemical and Thermal Properties of Phenol-Formaldehyde-Modified Polyphenol Impregnate," *J. Applied Polymer Sci. 84*:1567-1571, John Wiley & Sons, Inc. (2001).
Seurynck, S.L., et al., "Design, Synthesis, and Testing of Peptoid-Based Lung Surfactant Protein Mimics," *Biophysical Journal 84*:298A, 1450-Pos Board #B705, Biophysical Society (Feb. 2003).
Shin, S.Y. et al., "Effects of the hinge region of cecropin A(1-8)-magainin 2(1-12), a synthetic antimicrobial peptide, on liposomes, bacterial and tumor cells," *Biochim. et. Biophys. Acta 1463:209-218*, Elsevier Science B.V. (2000).
Siepmann, J.I., and Frenkel, D., "Configurational bias Monte Carlo: a new sampling scheme for flexible chains," Mol. Phys. 75:59-70, Taylor & Francis Ltd. (1992).
Sondossi, M., et al., "Factors Involved in Bactericidal Activities of Formaldehyde and Formaldehyde Condensate/Isothiazolone Mixtures," *Int. Biodeterioration & Biodegradation32*:243-261, Elsevier Science (1993).
Vlugt, T.J.H., et al., "Improving the efficiency of the configurational-bias Monte Carlo algorithm," *Mol. Phys. 94*:727-733, Taylor & Francis Ltd. (1998).
Wick, C.D. et al., "Transferable Potentions for Phase Equilibria. 4. United-Atom Description of Linear and Branched Alkenes and Alkyilenzenes," *J. Phys. Chem. B 104*:8008-8016, American Chemical Society (2000).
Yamaguchi, I., et al., "Synthesis of Polyurea rotaxanes using a cyclodextrin complexes of α, ω-diamine," *Polym. Bull. 44*:247-253, Springer-Verlag (2000).
Zushun, X. and Linxian, F., "Development of the Study on Solution Properties of Amphipathic Polymers and their Emulsion Polymerization," *Polymer Materials Science and Engineering 14*:1-4 (1998).

(56) References Cited

OTHER PUBLICATIONS

Office Action mailed on Jun. 23, 2009 in U.S. Appl. No. 10/801,951, inventors DeGrado et al., filed Mar. 17, 2004.
Office Action mailed on Feb. 2, 2009 in U.S. Appl. No. 10/801,951, inventors DeGrado et al., filed Mar. 17, 2004.
Office Action mailed on Mar. 9, 2009 in U.S. Appl. No. 10/471,029, inventors DeGrado et al., 371(c) date Jun. 7, 2004.
Final Office Action mailed on Aug. 6, 2009 in U.S. Appl. No. 11/361,050, inventors DeGrado et al., filed Feb. 24, 2006.
Office Action mailed on Feb. 5, 2009 in U.S. Appl. No. 11/361,050, inventors DeGrado et al., filed Feb. 24, 2006.
Tew, G.N. et al. "Antimicrobial activity of an abiotic host defense peptide mimic", *Biochimica et Biophysica Acta 1758*:1387-1392, Elsevier B.V. (2006).
Braga, D. and Grepioni, F., "Making crystals from crystals: a green route to crystal engineering and polymorphism," *Chem. Commun. 29*:3635-3643, Royal Society of Chemistry, England (Jun. 2005).
Chattaway, F.D. and Evans, R.C.T., "The diphenylbenzenes. I. Metadiphenylbenzene," *J. Chem. Soc. 69*:980-985, United States (1896).
Cook, W.A. and Cook, K.H., "The Halogenation of Meta-Diphenylbenzene. I. The Monochloro and Monobromo Derivatives," *J. Am. Chem. Soc. 55*:1212-1217, United States (1933).
Ishitsuka, Y., et al., "Amphiphilic Poly(phenyleneethynylene)s Can Mimic Antimicrobial peptide Membrane Disordering Effect by Membrane Insertion," *J. Am. Chem. Soc. 128(40)*:13123-13129, American Chemical Society, United States (2006).
Orita, A., et al., "Double elimination protocol for access to unsymmetrical Di(phenylethynl) benzenes," *Chemistry Letters 32(1)*:104-105, Chemical Society of Japan, Japan (2003).
Table of Contents of *Chemistry Letters 32(1)*, pp. 1-9, Chemical Society of Japan, Japan (2003).
Non-Final Office Action issued in U.S. Appl. No. 11/038,787, mailed May 21, 2009, inventors DeGrado et al.
Final Office Action issued in U.S. Appl. No. 11/038,787, mailed Oct. 20, 2009, inventors DeGrado et al.
Final Office Action issued in U.S. Appl. No. 11/038,787, mailed Jul. 1, 2010, inventors DeGrado et al.
Final Office Action issued in U.S. Appl. No. 11/038,787, mailed Oct. 25, 2010, inventors DeGrado et al.
Non-Final Office Action issued in U.S. Appl. No. 11/038,787, mailed Jan. 12, 2010, inventors DeGrado et al.
Supplemental Non-Final Office Aciton issued in U.S. Appl. No. 11/038,787, mailed Mar. 22, 2010, inventors DeGrado et al.
Final Office Action issued in U.S. Appl. No. 11/038,787, mailed Feb. 22, 2011, inventors DeGrado et al.
Non-Final Office Action issued in U.S. Appl. No. 11/038,787, mailed Nov. 9, 2011, inventors DeGrado et al.
Non-Final Office Action issued in U.S. Appl. No. 11/038,787, mailed Jan. 23, 2012, inventors DeGrado et al.
Notice of Allowance issued in U.S. Appl. No. 11/038,787, mailed Feb. 21, 2012, inventors DeGrado et al.
Advisory Action issued in U.S. Appl. No. 11/038,787, mailed May 17, 2011, inventors DeGrado et al.
Saiki, Y., et al., "[3 +3]Cycloalkyne Dimers Linked by an Azo Group: A Stable *cis*-Azo Compound Forms Polymeric Aggregates by Nonplanar π- π Interactions," *J. Am. Chem. Soc. 125(31)*:9268-9, American Chemical Society, United States (2003).
Nakamura, K., et al., "Low Temperature Sonogashira Coupling Reaction," *Synlett 5*:549-550, Thieme Stuttgart, New York (1999).
Pugsley, M.L., et al., "Protamine is a low molecular weight polycationic amine that produces actions on cardiac muscle," *Life Sci. 72(3)*:293-305, Elsevier, Netherlands (2002).
Tang, H., et al., "Synthesis of urea oligomers and their antibacterial activity," *Chem. Commun. 28(12)*:1537-9, Royal Society of Chemistry, England (Jan. 2005).
Ulrich, J. and Stelzer, T., Chapter 4 in Crystallization, Kirk-Othmer Encyclopedia of Chemical Technology, John Wiley & Sons, pp. 1-63, United States (2007).
West, A.R., "Solid State Chemistry and Its Applications," pp. 358 and 365, Wiley, India (1989).
Zhao, C., et al., "Identification of a New Member of the Protegrin Family by cDNA Cloning," *FEBS Lett. 346*:285-288, Federation of European Biochemical Societies, Netherlands (1994).
Xu, Z., et al., "Development of the Study on Solution Properties of amphipathic Polymers and Their Emulsion Polymerization," *Polymer Materials Science and Engineering 14*:1-4 (1998).
Notice of Allowance issued in U.S. Appl. No. 13/559,065, mailed Jan. 25, 2013, inventors DeGrado et al.
Non-Final Office Action issued in U.S. Appl. No. 11/361,050, mailed Jun. 17, 2013, inventors DeGrado et al.
Pearce, H.L., et al., "Chapter 18: Failure modes in anticancer drug discovery and development," in *Cancer Drug Design and Discovery*, Neidle, S., ed., pp. 424-435, Elsevier Inc., United States (2008).
Roberts, T.G., et al., "Trends in the Risks and Benefits to Patients With Cancer Participating in Phase 1 Clinical Trials," *Journal of the American Medical Association 292(17)*:2130-2140, American Medical Association, United States (2004).
Non-Final Office Action issued in U.S. Appl. No. 10/801,951, mailed Sep. 25, 2013, inventors DeGrado et al.

\* cited by examiner

FIG. 3
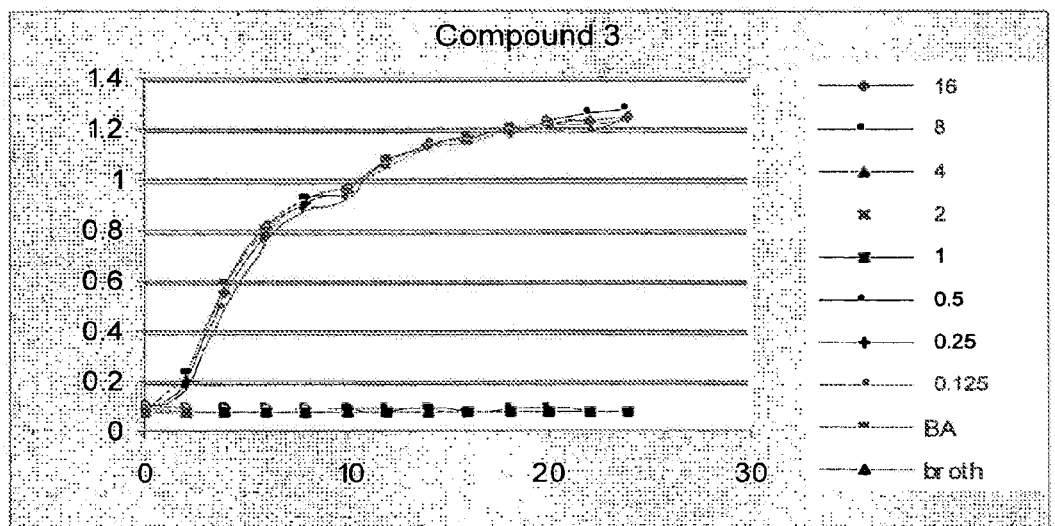
FIG. 3A
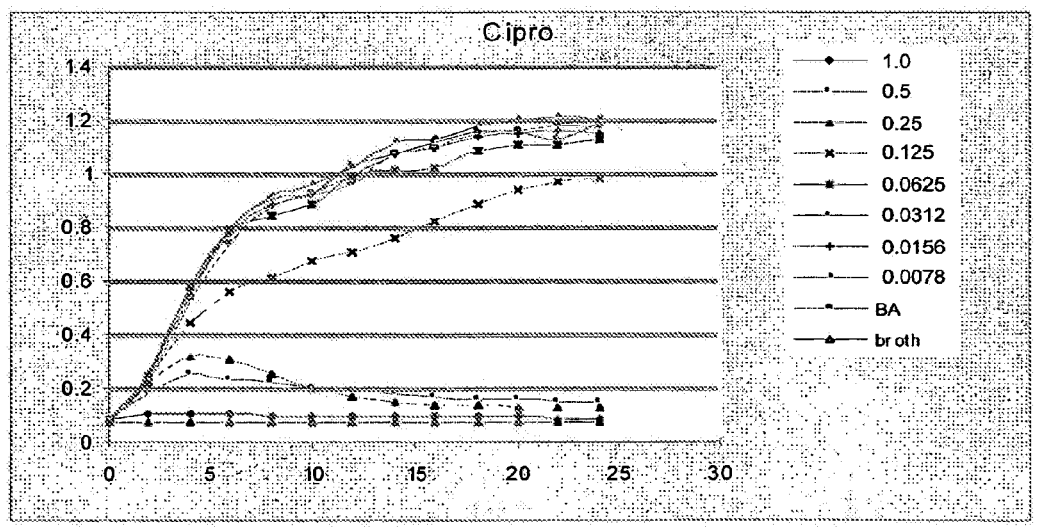
FIG. 3B

Glass Slide

Polyurethane (-) Oligomer

Polyurethane (+) Oligomer

FACIALLY AMPHIPHILIC POLYARYL AND POLYARYLALKYNYL POLYMERS AND OLIGOMERS AND USES THEREOF

CROSS REFERENCE TO RELATED APPLICATIONS

This application is a division of U.S. patent application Ser. No. 11/038,787 filed Jan. 21, 2005, now U.S. Pat. No. 8,222, 456, which claims the benefit, under 35 U.S.C. §119(e), of the earlier filing date of U.S. Provisional Application No. 60/538, 270, filed on Jan. 23, 2004, which is incorporated by reference herein in its entirety.

STATEMENT REGARDING FEDERALLY-SPONSORED RESEARCH

This invention was made with government support under Grant No. GM-65803 awarded by the National Institutes of Health. The U.S. Government has certain rights in this invention.

BACKGROUND OF THE INVENTION

1. Field of the Invention

The present invention relates to methods of use of facially amphiphilic polyaryl and polyarylalkynyl polymers and oligomers, including pharmaceutical uses of the polymers and oligomers as antimicrobial agents and as antidotes for hemorrhagic complications associated with heparin therapy. The present invention also relates to novel facially amphiphilic polyaryl and polyarylalkynyl polymers and oligomers and their compositions, including pharmaceutical compositions.

2. Background Art

Bacterial drug resistance is a significant current health problem throughout the world. Multiple drug resistance is being commonly seen in a number of human pathogens (Hiramatsu, K., et al., *J. Antimicrob. Chemother.* 40:311-313 (1998); Montecalvo, M. A., et al., *Antimicro. Agents Chemother.* 38:1363-1367 (1994); Butler, J. C., et al., *J. Infect. Dis.* 174:986-993 (1996); Lyytikainen, O., et al., *J. Hosp. Infect.* 31:41-54 (1995)), and the incidence of drug-resistant hospital infections is growing at a rapid rate. In some U.S. hospitals, nosocomial pathogens, such as *E. faecium* and *Acinetobacter* species, have acquired multiple resistance determinants and are virtually untreatable with current antimicrobial agents (Threlfall, E. J., et al., *Lancet* 347:1053-1054 (1996); Bradley, J. S., and Scheld, W. M., *Clin. Infect. Dis.* 24 (*Suppl.* 2):S213-221 (1997)). Bacterial resistance has now reached epidemic proportions and has been attributed to a variety of abuses of antibiotic treatments, including overuse (Monroe, S., and Polk, R., *Curr. Opin. Microbiol.* 3:496-501 (2000)), inappropriate dosing at sub-therapeutic levels (Guillemot, D., et al., *JAMA* 279:365-370 (1998)), and misuse as antimicrobial growth promoters in animal food (Lathers, C. M., *J. Clin. Pharmacol.* 42:587-600 (2002)). The threat of bio-terrorism has provided a further impetus to develop novel classes of antibiotics, particularly ones against which it will be difficult to develop resistant bacterial strains. The pharmaceutical scientific community is responding to this challenge by focusing on the development of new antibiotic drugs. Much of this work, however, is directed to synthesizing analogs of known drugs, such as cephalosporins and quinolones, that, while potentially useful for a short time, will inevitably also encounter bacterial drug resistance and become ineffective. Antibacterial drugs currently represent approximately 65% of the market in infectious disease drags (Global Information, *The world market for anti-infective series: Volume II: The world market for antibacterial medications*, Kalorama Information (2003)). Thus, therapeutically effective antimicrobial drugs that act by novel mechanisms would provide an economc as well as a human health benefit.

Following the initial discovery of cecropins and magainins, antimicrobial peptides have become a large and growing class of biologically interesting compounds (Zasloff, M., *Curr. Opin. Immunol.* 4:3-7 (1992); Zasloff, M., *Trends Pharmacol. Sci.* 21:236-238 (2000)). These compounds represent the first line of defense against microbes for many species, including plants, insects, worms, and mammals (Boman, H. G., *Immunol. Rev.* 173:5-16 (2000); Hancock, R. E., and Lehrer, R., *Trends Biotechnol.* 16:82-88 (1998)). In mammals, the peptides are produced and secreted by skin, mucosal surfaces and neutrophils. There are many different classes of natural host defense peptides (Zasloff, M., *Curr. Opin. Immunol.* 4:3-7 (1992); Zasloff, M., *Trends Pharmacol. Sci.* 21:236-238 (2000); Steiner, H., et al., *Nature,* 292:246-248 (1981); Ganz, T., et al., *Eur. J. Haematol.* 44:1-8 (1990); Tang, Y. Q., et al., *Science* 286:498-502 (1999); Ganz, T., et al., *J. Clin. Invest.* 76:1427-1435 (1985); Landon, C., et al., *Protein Sci.* 6:1878-1884 (1997); Zhao, C., et al., *FEBS Lett.* 346:285-288 (1994); Peggion, E., et al., *Biopolymers (Peptide Science)* 43:419-431 (1998); Dempsey, C. E., *Biochim. Biophys. Acta* 1031:143-161 (1990)), but, in general, most contain between 20-40 amino acid residues and adopt an amphiphilic secondary structure as shown in FIG. 1.

Although host defense peptides are found in a wide variety of species and are composed of many different sequences, their physiochemical properties are remarkably similar. They adopt an amphiphilic architecture with positively charged groups segregated to one side of the secondary structure and hydrophobic groups on the opposite surface. For example, magainin and some of the other naturally occurring antibacterial peptides contain positively charged amino acids and a large hydrophobic moment. Although these peptides exhibit considerable variation in their chain length, hydrophobicity and distribution of charges, they have a high propensity to adopt α-helical conformations in a hydrophobic environment, e.g., a cell surface or a natural or synthetic membrane (Oren, Z., and Shai, Y., *Biopolymers (Peptide Science)* 47:451-463 (1998)). The periodic distribution of hydrophobic and hydrophilic side chains in their amino acid sequences allows the segregation of the hydrophobic and hydrophilic side chains to opposite faces of the cylinder formed by the helix. These structures can be described as facially amphiphilic regardless of whether the secondary structure is a helix or sheet type fold. In fact, it is the overall physiochemical properties that are responsible for the biological activity of these peptides and not the precise sequence (Zasloff, M., *Curr. Opin. Immunol.* 4:3-7 (1992); Zasloff, M., *Trends Pharmacol. Sci.* 21:236-238 (2000); Hancock, R. E., and Lehrer, R., *Trends Biotechnol.* 16:82-88 (1998); DeGrado, W. F., et al., *J. Amer. Chem. Soc.* 103:679-681 (1981); DeGrado, W. F., *Adv. Prot. Chem.* 39:51-124 (1988); Tossi, A., et al., *Biopolymers* 55:4-30 (2000); Merrifield, E. L., et al., *Int. J. Pept. Protein Res.* 46:214-220 (1995); Merrifield, R. B., et al., *Proc Natl Acad Sci (USA)* 92:3449-3453 (1995)). Because the overall amphiphilicity, not the specific sequence, secondary structure or chirality, correlates best with the anti-microbial activity of these peptides, it appears that any suitably amphiphilic material (not necessarily an α-helix or β-sheet) would have anti-microbial properties.

The cytotoxic activity of these cationic and amphiphilic antimicrobial peptides is also specific for bacteria over mammalian cells. This specificity is most likely related to fundamental differences between the two membrane types. For example, bacteria have a large proportion of negatively charged phospholipid headgroups on their surface, while, in contrast, the outer leaflet of animal cells is composed mainly of neutral lipids (Zasloff, M., *Nature* 415:389-395 (2002)). The presence of cholesterol in the animal cell membrane also appears to reduce the activity of the antimicrobial peptides.

The bactericidal activity of the host defense peptides is very rapid, occurring within minutes after exposure of bacteria to lethal doses of peptide. Several mechanisms have been proposed for the process of cell killing. According to the carpet mechanism, host defense peptides aggregate parallel to the membrane surface (Gazit, E., et al., *Biohemistry* 34:11479-11488 (1995); Pouny, Y., et al., *Biochemistry* 31:12416-12423 (1992)), leading to thinning and, ultimately, rupture of the membrane. In the so-called barrel-stave mechanism, the bound peptides on the cell surface self-associate into transmembrane helical bundles that form stable aqueous pores in the membrane (Merrifield, R. B., et al., *Ciba Found. Symp.* 186:5-20 (1994)). According to a third possible mechanism (DeGrado, W. F., et al., *Biophys. J.* 37:329-338 (1982)), the peptides initially bind only to the outer leaflet of the bilayer, leading to an increase in the lateral surface pressure of the outer leaflet relative to the inner leaflet of the bilayer. This pressure imbalance results in translocation of the peptides into the interior of the bilayer with concomitant formation of transient openings in the membrane. Formation of these transient pores allows hydration of the polar sidechains of the peptide and leakage of cellular contents. Most antimicrobial peptides probably act by more than one of these mechanisms. Additionally, some classes may interact with periplasmic or intercellular targets (Zasloff, M., *Trends Pharmacol. Sci.* 21:236-238 (2000)).

In addition to the well-characterized antibacterial activity, several of the host defense peptides possess antifungal activity. Examples of mammalian, insect and amphibian peptides with demonstrated antifungal activities include defensins, protegrins, lactoferrin-B, cecropins, and dermaseptins (DeLucca, A. J., and Walsh, T. J., *Antimicob. Agents Chemother.* 43:1-11 (1999)). The mechanism of cytotoxic action appears to be similar to that for bacteria, leading to rapid lysis of the fungal membrane.

Several host defense peptides also possess antiviral activity. For example, several classes of host defense peptides also inhibit the replication of both DNA and RNA viruses. NP-1, a prototypic alpha-defensin, protects cells in culture from infection by herpes simplex virus-2. The block appears to occur very early in the infection cycle as the peptide prevents viral entry but does interfere with binding between the viral glycoproteins and the cellular heparin sulfate receptors (Sinha, S., et al., *Antimicrob. Agents Chemother.* 47:494-500 (2003)). Several other host defense peptides have been shown to have antiviral activity against herpes simplex virus-1 (Belaid, A., et al., *J. Med. Virol.* 66:229-234 (2002); Egal, M., et al., *Int. J. Antimicrob. Agents* 13:57-60 (1999)) as well as human cytomegalovirus virus (Andersen, J. H., et al., *Antiviral Rs.* 51:141-149 (2001)). NP-1 also inhibits adenoviral infection in cell culture (Bastian, A., and Schafer, H., *Regul. Pept.* 15:157-161 (2001)).

The human alpha-defensins have also been shown to inhibit the replication of HIV-1 isolates in vitro (Zhang, L., et al., *Science* 298: 995-1000 (2002)) and to be the active components of a soluble fraction that suppresses HIV-1 replication which is secreted from CD8 T lymphocytes isolated from long-term nonprogressing AIDS patients (Zhang, L., et al., *Science* 298: 995-1000 (2002)). The mechanism by which the defensins inhibit HIV replication is unknown but the block occurs early in the infection cycle at or near the time of viral entry. The antimicrobial peptides melittin and cecropin have also been reported to inhibit HIV-1 replication and it is suggested that they exert their activity by suppressing HIV gene expression (Wachinger, M., et al., *J. Gen. Virol.* 79:731-740 (1998)).

The mechanism of antiviral action of the host defense peptides appears not to be related to direct virucidal activity, where the integrity of the virion is disrupted, but rather at an early stage in the infection cycle during entry of the virus into the host cell.

The design of non-biological polymers with well-defined secondary and tertiary structures has received considerable attention in the past few years (Gellman, S. H., *Acc. Chem. Res.* 31:173-180 (1998); Barron, A. E., and Zuckermann, R. N., *Curr. Opin. Chem. Biol.* 3:681-687 (1999); Stigers, K. D., et al., *Curr. Opin. Chem. Biol.*, 3:714-723 (1999)). Using these principles, investigators have designed synthetic antimicrobial peptides by idealizing the amphiphilic α-helical arrangement of sidechains observed in the natural host defense peptides, leading to a large number of potent and selective antimicrobial compounds (Tossi, A., et al., *Biopolymers* 55:4-30 (2000); DeGrado, W. F., *Adv. Protein. Chem.* 39:51-124 (1988); Maloy, W. L., and Kari, U. P., *Biopolymers* 37:105-122 (1995); Zasloff, M., *Curr. Opin. Immunol.* 4:3-7 (1992); Boman, H. G., et al., *Eur. J. Biochem.* 201:23-31 (1991); Oren, Z., and Shai, Y., *Biopolymers* 47:451-463 (1998)).

β-peptides have also provided another avenue to test and further elucidate the features required for the construction of bactericidal agents. β-peptides adopt L+2 helices, which have an approximate 3-residue geometric repeat. Thus, if polar and apolar sidechains are arranged with precise three-residue periodicity in the sequence of a β-peptide, they should segregate to opposite sides of the helix. Using this approach, DeGrado and co-workers (Hamuro, Y., et al., *J. Amer. Chem. Soc.* 121:12200-12201 (1999); Liu, D., and DeGrado, W. F., *J. Amer. Chem. Soc.*, 123:7553-7559 (2001)) have designed synthetic β-peptide oligomers that are roughly equipotent in antimicrobial activity to many naturally occurring peptide antibiotics. The antimicrobial activities of these β-peptides and their specificities for bacterial cells over mammalian cells can be controlled by fine-tuning their hydrophobicities and chain lengths. Gellman and coworkers have also synthesized cyclically constrained β-peptides possessing potent antimicrobial activity and minimal activity against mammalian cells (Porter, E. A., et al., *Nature* 404:565 (2000)).

Non-peptidic antimicrobial polymers have also been developed. For example, suitably substituted polymers lacking polyamide linkages that are capable of adopting amphiphilic conformations have been designed and synthesized. Solid phase chemistry technology has been utilized to synthesize a class of meta substituted phenylacetylenes that fold into helical structures in appropriate solvents (Nelson, J. C., et al, *Science* 277:1793-1796 (1997); Prince, R. B., et al., *Angew. Chem. Int. Ed.* 39:228-231 (2000)). These molecules contain an all hydrocarbon backbone with ethylene oxide side chains such that when exposed to a polar solvent (acetonitrile), the backbone collapses to minimize its contact with this polar solvent. As a result of the meta substitution, the preferred folded conformation is helical. This helical folding is attributed to a "solvophobic" energy term; although, the importance of favorable π-π aromatic interactions in the folded state are also likely to be important. Furthermore, addition of a less polar solvent ($CHCl_3$) results in an unfolding of the helical structure demonstrating that this folding is reversible.

In addition, Mandeville et al., U.S. Pat. No. 6,034,129, disclose anti-infective vinyl copolymers, wherein monomers with hydrophobic and hydrophilic side chains have been randomly polymerized to produce polymers with amphiphilic properties. These materials are produced by polymerization of hydrophobic and hydrophilic acrylate monomers. Alternately, the hydrophobic side chain is derived from a styrene derivative which is copolymerized with a hydrophilic acrylate monomer wherein an ionic group is linked to the carboxylic, acid.

Tew et al. (Tew, G. N., et al., *Proc. Natl. Acad. Sci.* (*USA*) 99:5110-5114 (2002)) disclose the design and synthesis of a series of biomimetic, facially amphiphilic arylamide polymers possessing antimicrobial activity. The arylamide polymers were designed using de novo computational design techniques.

WIPO Publ. No. WO 02/100295 discloses facially amphiphilic polyamide, polyester, polyurea, polycarbonate, and polyurethane polymers with anti-infective activity, and articles made from them having biocidal surfaces. WIPO Publ. No. WO 02/100295 is fully incorporated by reference herein in its entirety.

WIPO Publ. No. WO 02/072007 discloses a number of facially amphiphilic polyphenylene and heteroarylene polymers, including polyphenylalkynyl polymers, with anti-infective activity and articles made therefrom having biocidal surfaces. WIPO publication no. WO 02/072007 is fully incorporated by reference herein in its entirety.

BRIEF SUMMARY OF THE INVENTION

The present invention provides methods of use of facially amphiphilic polyaryl and polyarylalkynyl polymers and oligomers, including, but not limited to, pharmaceutical uses of the polymers and oligomers as antimicrobial agents and as antidotes for hemorrhagic complications associated with heparin therapy. The present invention also provides novel facially amphiphilic polyaryl and polyarylalkynyl polymers and oligomers, as well as compositions, including pharmaceutical compositions, and methods of using the novel polymers and oligomers.

The facially amphiphilic polyaryl and polyarylalkynyl polymers and oligomers of the present invention are compounds of Formula I,

$$R^1—[-A_1\text{-}s\text{-}A_2\text{-}s\text{-}]_m—R^2 \qquad (I)$$

or acceptable salts or solvates thereof, wherein $R^1$, $R^2$, $A_1$, $A_2$, s and m are as defined below. Facially amphiphilic polyaryl and polyarylalkynyl oligomers of the present invention also include compounds of Formula Ia,

$$R^1\text{-}A_1\text{-}s\text{-}A_2\text{-}s\text{-}A_1\text{-}R^2 \qquad (Ia)$$

or acceptable salts or solvates thereof, wherein $R^1$, $R^2$, $A_1$, $A_2$, and s are as defined below.

The present invention is directed to a method of treating a microbial infection in an animal in need thereof, the method comprising administering to the animal an effective amount of a pharmaceutical composition comprising a polymer or an oligomer of Formula I, or an acceptable salt or solvate thereof, and a pharmaceutically acceptable carrier or diluent. In some aspects of the invention, the microbial infection is a bacterial infection, a fungal infection, or a viral infection.

The present invention is also directed to a method of killing or inhibiting the growth of a microorganism, the method comprising contacting the microorganism with an effective amount of a polymer or an oligomer of Formula I, or an acceptable salt or solvate thereof. In some aspects of the invention, the microorganism is a bacterial cell, a fungus, or a virus.

The present invention is further directed to a method of providing an antidote to low molecular weight heparin overdose in an animal, the method comprising administering to the animal an effective amount of a pharmaceutical composition comprising a polymer or an oligomer of Formula I, or an acceptable salt or solvate thereof, and a pharmaceutically acceptable carrier or diluent.

The present invention is also directed to an oligomer of Formula Ia, or an acceptable salt or solvate thereof.

The present invention is further directed to a pharmaceutical composition comprising an oligomer of Formula Ia, or an acceptable salt or solvate thereof.

The present invention is directed to a method of treating a microbial infection in an animal in need thereof, the method comprising administering to the animal an effective amount of a pharmaceutical composition comprising an oligomer of Formula Ia, or an acceptable salt or solvate thereof, and a pharmaceutically acceptable carrier or diluent. In some aspects of the invention, the microbial infection is a bacterial infection, a fungal infection, or a viral infection.

The present invention is also directed to a method of killing or inhibiting the growth of a microorganism, the method comprising contacting the microorganism with an effective amount of an oligomer of Formula Ia, or an acceptable salt or solvate thereof. In some aspects of the invention, the microorganism is a bacterial cell, a fungus, or a virus.

The present invention is directed to a method of providing an antidote to low molecular weight heparin overdose in an animal, the method comprising administering to the animal an effective amount of a pharmaceutical composition comprising an oligomer of Formula Ia, or an acceptable salt or solvate thereof, and a pharmaceutically acceptable carrier or diluent.

BRIEF DESCRIPTION OF THE DRAWINGS

FIG. 3 shows the results of the growth inhibition time course experiments described in Example 3 in which Compound 3 was tested for its ability to inhibit the growth of *Bacillus anthracis* over time. FIG. 3A presents data obtained with Compound 3. FIG. 3B presents data obtained with the positive control antibiotic, ciprofloxacin.

FIG. 4 shows the results of assays in which the phenyl alkynyl trimer Compound 3 was incorporated into polyurethane film. The figures represent untreated glass (top figure), untreated polyurethane film (middle figure), and polyurethane film containing Compound 3 (bottom figure), after incubation of each in the presence of *E. coli* for 62 hours.

DETAILED DESCRIPTION OF THE INVENTION

The present invention provides non-peptidic, facially amphiphilic polyaryl and polyarylalkynyl polymers and oligomers and methods of using of the polymers and oligomers in a number of applications, including their use in pharmaceutical applications as antimicrobial agents and as antidotes for hemorrhagic complications associated with heparin therapy. The present invention also provides novel facially amphiphilic polyaryl and polyarylalkynyl polymers and oligomers, as well as compositions comprising the novel polymers and oligomers. The present invention further provides methods of designing and synthesizing facially amphiphilic polyaryl and polyarylalkynyl polymers and oligomers.

Figure 1:
FIG. 1 shows a schematic representation of the structure for the cationic and amphiphilic α-helical host defense peptide, magainin 1. Hydrophobic residues are dark, basic residues are light.

The polyaryl and polyarylalkynyl polymers and oligomers of the present invention are compounds of Formula I,

                                           (I)

or compounds of Formula Ia,

                                           (Ia)

or acceptable salts or solvates thereof, wherein $R^1$, $R^2$, $A_1$, $A_2$, s and m are as defined below.

Facially amphiphilic polymers and oligomers of Formula I and Formula Ia are capable of adopting amphiphilic conformations that allow for the segregation of polar and nonpolar regions of the molecule into different spatial regions.

The amphiphilic conformations adopted by the polymers and oligomers of the present invention provide the basis for a number of uses. For example, polymers and oligomers of Formula I and Formula Ia adopt amphiphilic conformations that are capable of disrupting the integrity of the cell membrane of microorganisms, resulting in the inhibition of growth or the death of the microorganisms. As a consequence, the polymers and oligomers possess antimicrobial activity, including antibacterial, antifungal, and antiviral activity, and are useful as antimicrobial agents. The polymers and oligomers of Formula I and Formula Ia have a broad range of antimicrobial activity and are effective against a variety of microorganisms, including gram-positive and gram-negative bacterial, fangi, yeast, mycoplasmas, mycobacteria, protozoa, and the like.

The polymers and oligomers of the present invention are useful as antimicrobial agents in a number of applications. For example, polymers and oligomers of Formula I and Formula Ia, especially oligomers of Formula I and Formula Ia, can be used therapeutically to treat microbial infections in animals, including humans and non-human vertebrates such as wild, domestic and farm animals. The microbial infection in an animal is treated by administering to the animal an effective amount of a pharmaceutical composition of a polymer or oligomer of Formula I or Formula Ia, especially an oligomer of Formula I or of Formula Ia. The polymer or oligomer compositions can be administered systemically or topically and can be administered to any body site or tissue. Because the polymers and oligomers have a broad range of antimicrobial activity, they are useful in treating a variety of infections in an animal.

The facially amphiphilic conformations adopted by the polymers and oligomers of the present invention form the basis for another therapeutic use, the use of the polymers and oligomers as antidotes for hemorrhagic complications associated with heparin therapy. Thus, the polymers and oligomers of Formula I and Formula Ia, especially the oligomers of Formula I or Formula Ia, can be used in a method of providing an antidote to heparin overdose in an animal by administering to the animal an effective amount of a pharmaceutical composition of the polymer or oligomer.

The polymers and oligomers of the present invention can also be used as disinfectants or as preservatives. The polymers and oligomers of Formula I and Formula Ia can thus be used in a method of killing or inhibiting the growth of a microorganism by contacting the microorganism with an effective amount of the polymer or oligomer. For example, the polymers and oligomers of Formula I and Formula Ia can be used as disinfectants or preservatives in, for example, soaps, hand lotions, paints, cleansers, and polishers, and the like, or in, for example, foodstuffs, food containers, and food-handling implements. The polymers and oligomers are administered for these purposes as a solution, dispersion, or suspension. The polymers and oligomers of Formulae I and Ia can also be incorporated into plastics that can be molded or shaped into articles, or attached or immobilized on a surface, to provide a surface-mediated microbicide that kills or inhibits the growth of microorganisms in contact with the surface.

The polymers and oligomers of the present invention were originally designed to mimic the antimicrobial activities of host defense peptides, which were potentially exciting therapeutic agents because of their broad spectrum of activity, rapid bacteriocidal activity, and very low incidence of development of bacterial resistance. However, significant pharmaceutical issues, including systemic toxicity and difficulty and expense of manufacturing, severely hampered clinical progress in the use of the host defense peptides as therapeutics.

The present invention directly addresses those pharmaceutical issues. Many of the oligomers of Formula I and Formula Ia are significantly smaller and easier to prepare than their naturally occurring counterparts. They have the same mechanism of action as magainin (a naturally occurring host defense peptide) and are approximately equipotent and as broad in their spectrum of action as magainin. However, the non-peptidic polymers and oligomers of the present invention are significantly less toxic towards human erythrocytes, much less expensive to prepare, and are expected to be much more stable in vivo. Importantly, because these polymers and oligomers mimic the structure and biological activity of host defense peptides, the appearance of resistant bacterial strains is very unlikely to occur. Thus, the facially amphiphilic polymers and oligomers of the present invention offer several important and novel advantages.

The present invention discloses facially amphiphilic polymers and oligomers. Polymers are generally defined as synthetic compounds assembled from monomer subunits that are polydisperse in molecular weight, and are most commonly prepared by one-pot synthetic procedures. The term "polymer" as used herein refers to a macromolecule comprising a plurality of repeating units or monomers. The term includes homopolymers, which are formed from a single type of monomer, and copolymers, which are formed from two or more different monomers. In copolymers, the monomers may be distributed randomly (random copolymer), in alternating fashion (alternating copolymers), or in blocks (block copolymer). The polymers of the present invention are either homopolymers or alternating copolymers having about 2 monomer units to about 500 monomer units, with average molecular weights that range from about 300 Daltons to about 1,000,000 Daltons, or from about 400 Daltons to about 120,000 Daltons. Preferred polymers are those having about 5 to about 100 monomer units, with average molecular weights that range from about 1,000 Daltons to about 25,000 Daltons.

The term "oligomer" as used herein refers to as a homogenous polymer with a defined sequence and molecular weight. Modern methods of solid phase organic chemistry have allowed the synthesis of homodisperse, sequence-specific oligomers with molecular weights approaching 5,000 Daltons. An oligomer, in contrast to a polymer, has a defined sequence and molecular weight and is usually synthesized either by solid phase techniques or by step-wise solution chemistry and purified to homogeneity. Oligomers of the present invention are those having about 2 monomer units to about 25 monomer units, with molecular weights that range from about 300 Daltons to about 6,000 Daltons. Preferred oligomers are those having about 2 monomer units to about 10 monomer units, with molecular weights that range from about 300 Daltons to about 2,500 Daltons.

For pharmaceutical applications, oligomers are the preferred species because of their defined size and structure. For material applications, polymeric forms having well-defined repeat-length distributions are preferred because of their more economical synthesis.

The term "polymer backbone," "oligomer backbone," or "backbone" as used herein refers to that portion of the polymer or oligomer which is a continuous chain comprising the bonds formed between monomers upon polymerization. The composition of the polymer or oligomer backbone can be described in terms of the identity of the monomers from which it is formed without regard to the composition of branches, or side chains, of the polymer or oligomer backbone.

The term "polymer side chain," "oligomer side chain," or "side chain" refers to portions of the monomer which, following polymerization, forms an extension of the polymer or oligomer backbone. In homopolymers and homooligomers, all the side chains are derived from the same monomer.

The terms "treat," "treated," or "treating" as used herein refers to both therapeutic treatment and prophylactic or preventative measures wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; or enhancement or improvement of condition, disorder or disease. Treatment includes eliciting a clinically significant response without excessive levels of side effects. Treatment also includes prolonging survival as compared to expected survival if not receiving treatment.

The term "animal" as used herein includes, but is not limited to, humans and non-human vertebrates such as wild, domestic and farm animals.

The term "microorganism" as used herein includes bacteria, algae, fungi, yeast, mycoplasmas, mycobacteria, parasites and protozoa.

The term "antimicrobial," "microbiocidal," or "biocidal" as used herein means that the polymer, oligomer, or material described as such produce effects adverse to the normal biological functions of microorganisms, including death, destruction, or prevention of the growth or proliferation of the microorganism, when contacted with the polymer, oligomer, or material. This activity can be either bacteriostatic or bacteriocidal. The term "bacteriocidal" as used herein means the killing of microorganisms. The term "bacteriostatic" as used herein means inhibiting the growth of microorganisms and can be reversible under certain conditions.

The term "amphiphilic" as used herein describes a three-dimensional structure having discrete hydrophobic and hydrophilic regions. An amphiphilic polymer requires the presence of both hydrophobic and hydrophilic elements along the poly ner backbone. The presence of hydrophobic and hydrophilic groups is a necessary, but not sufficient, condition to produce an amphiphilic molecule, polymer or oligomer.

The term "facially amphiphilic" or "facial amphiphilicity" as used herein describes polymers or oligomers with polar (hydrophilic) and nonpolar (hydrophobic) side chains that adopt conformation(s) leading to segregation of polar and nonpolar side chains to opposite faces or separate regions of the structure or molecule.

The polyaryl and polyarylalkynyl polymers and oligomers of the present invention are those of Formula I,

$$R^1-[-A_1-s-A_2-s-]_m-R^2 \quad (I)$$

or an acceptable salt or solvate thereof,
wherein:
$A_1$ and $A_2$ are independently optionally substituted arylene or optionally substituted heteroarylene, wherein:
  (i) $A_1$ and $A_2$ are independently optionally substituted with one or more polar (PL) group(s), one or more non-polar (NPL) group(s), or a combination of one or more polar (PL) group(s) and one or more non-polar (NPL) group(s); or
  (ii) one of $A_1$ or $A_2$ is as defined above and is optionally substituted with one or more polar (PL) group(s), one or more non-polar (NPL) group(s), or a combination of one or more polar (PL) group(s) and one or more non-polar (NPL) group(s); and the other of $A_1$ or $A_2$ is the group —C≡C(CH$_2$)$_p$C≡C—, wherein p is 0 to 8, and the —(CH$_2$)$_p$— alkylene chain is optionally substituted with one or more amino or hydroxyl groups;
s is absent, or represents —CH$_2$—, —CH$_2$—CH$_2$—, —CH=CH—, or —C≡C—;
$R^1$ is
  (i) hydrogen, a polar group (PL), or a non-polar group (NPL), and $R^2$ is -$A_1$-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or
  (ii) hydrogen, a polar group (PL), or a non-polar group (NPL), and $R^2$ is -$A_1$-s-$A_2$-$R^1$, wherein each of $A_1$ and $A_2$ is as defined above and is optionally substituted with one or more polar (PL) group(s), one or more non-polar (NPL) group(s), or a combination of one or more polar (PL) group(s) and one or more non-polar (NPL) group(s); or
  (iii) A'-s- and $R^2$ is -$A_1$-s-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s); or
  (iv) A'-s- and $R^2$ is -A', wherein A' is aryl or heteroaryl, either of which is optionally substituted with one or more polar (PL) group(s), one or more non-polar (NPL) groups(s), or a combination of one or more polar (PL) group(s) and one or more non-polar (NPL) group(s); or
  (v) $R^1$ and $R^2$ together form a single bond;
NPL is a nonpolar group independently selected from —B(OR$^4$)$_2$ or —(NR$^{3'}$)$_{q1NPL}$—U$^{NPL}$—(CH$_2$)$_{pNPL}$—(NR$^{3''}$)$_{q2NPL}$—R$^4$, wherein:
  $R^3$, $R^{3'}$, and $R^{3''}$ are independently selected from the group consisting of hydrogen, alkyl, and alkoxy;
  $R^4$ is selected from the group consisting of hydrogen, alkyl, alkenyl, alkynyl, cycloalkyl, aryl, and heteroaryl, any of which is optionally substituted with one or more alkyl or halo groups;
  $U^{NPL}$ is absent or selected from the group consisting of O, S, S(=O), S(=O)$_2$, NR$^3$, —(C=O)—, —(C=O)—N=N—NR$^3$—, —(C=O)—NR$^3$—N=N—, —N=N—NR$^3$—, —C(=N—N(R$^3$)$_2$)—,
—C(=NR$^3$)—, —C(=O)O—, —C(=O)S—,
—C(=S)—, —O—P(=O)$_2$O—, —R$^3$O—, —R$^3$S—,
—S—C=N— and —(C=O)—NR$^3$—O—, wherein
groups with two chemically nonequivalent termini can
adopt both possible orientations;

the —(CH$_2$)$_{pNPL}$— alkylene chain is optionally substituted
with one or more amino or hydroxyl groups, or the
alkylene chain is unsaturated;

pNPL is 0 to 8;

q1NPL and q2NPL are independently 0 to 2;

PL is a polar group selected from the group consisting of halo,
hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5'}$)$_{q2PL}$—V,
wherein:

R$^5$, R$^{5'}$, and R$^{5''}$ are independently selected from the group
consisting of hydrogen, alkyl, and alkoxy;

U$^{PL}$ is absent or selected from the group consisting of O, S,
S(=O), S(=O)$_2$, NR$^5$, —(C=O)—, —(C=O)—
N=N—NR$^5$—, —(C=O)—NR$^5$—N=N—,
—N=N—NR$^5$—, —C(=N—N(R$^5$)$_2$)—,
—C(=NR$^5$)—, —C(=O)O—, —C(=O)S—,
—C(=S)—, —O—P(=O)$_2$O—, —R$^5$O—, —R$^5$S—,
—S—C=N— and —(C=O)—NR$^5$—O—, wherein
groups with two chemically nonequivalent termini can
adopt both possible orientations;

V is selected from the group consisting of nitro, cyano,
amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone,
aryl, heterocycle and heteroaryl, any of which is optionally substituted with one or more of amino, halo, cyano,
nitro, hydroxyl, —NH(CH$_2$)$_p$NH$_2$, —N(CH$_2$CH$_2$NH$_2$)$_2$, amidino, guanidino, guanyl, aminosulfonyl,
aminoalkoxy, aminoalkylthio, lower acylamino, or benzyloxycarbonyl;

the —(CH$_2$)$_{pPL}$— alkylene chain is optionally substituted
with one or more amino or hydroxyl groups, or the
alkylene chain is unsaturated;

pPL is 0 to 8;

q1PL and q2PL are independently 0 to 2; and m is 1 to at least about 500;

with the proviso that if A$_1$ and A$_2$ are thiophene, the polar
groups cannot be 3-(propionic acid) or methoxy(diethoxy)ethyl and the nonpolar group cannot be n-dodecyl;

and a pharmaceutically acceptable carrier or diluent.

Polymers and oligomers of Formula I that are preferred for
use in the disclosed methods are those wherein A$_1$ and A$_2$ are
independently optionally substituted o-, m-, or p-phenylene.
Those oligomers wherein A$_1$ and A$_2$ are optionally substituted
m-phenylene are especially preferred. Also preferred are
polymers and oligomers of Formula I wherein one of A$_1$ or A$_2$
is o-, m-, or p-phenylene, and the other of A$_1$ or A$_2$ is heteroarylene. Preferred heteroarylene groups include, but are
not limited to, pyridinyl, pyrimidinyl, and pyrazinyl.

Also preferred are polymers and oligomers of Formula I
wherein A$_1$ and A$_2$ are independently optionally substituted
arylene or optionally substituted heteroarylene, and (i) one of
A$_1$ or A$_2$ is substituted with one or more polar (PL) group(s)
and one or more nonpolar (NPL) group(s) and the other of A$_1$
or A$_2$ is unsubstituted; or (ii) one of A$_1$ or A$_2$ is substituted
with one or more polar (PL) group(s) and the other of A$_1$ or A$_2$
is unsubstituted; or (iii) one of A$_1$ or A$_2$ is substituted with one
or more polar (PL) group(s) and the other of A$_1$ or A$_2$ is
substituted with one or more nonpolar (NPL) group(s). Polymers and oligomers in which either (i) one of A$_1$ or A$_2$ is
substituted with one or more polar (PL) group(s) and one or
more nonpolar (NPL) group(s), and the other of A$_1$ or A$_2$ is
unsubstituted, or (ii) one of A$_1$ or A$_2$ is substituted with one or
more polar (PL) group(s) and the other of A$_1$ or A$_2$ is unsubstituted, are especially preferred.

Polymers and oligomers of Formula I are preferred in
which A$_1$ and A$_2$ are optionally substituted m-phenylene,
wherein one of A$_1$ or A$_2$ is substituted with one or more polar
(PL) group(s) and the other of A$_1$ or A$_2$ is unsubstituted. Those
polymers and oligomers wherein one of A$_1$ or A$_2$ is substituted with one or two polar groups and the other of A$_1$ or A$_2$
is unsubstituted are especially preferred.

In some aspects of the invention, preferred polymers and
oligomers of Formula I are those wherein s is absent.

In other aspects, polymers and oligomers of Formula I that
are preferred for use in the disclosed methods are those
wherein s is —CH=CH— or —C≡C—. Especially preferred are oligomers of Formula I in which s is —C≡C—.

Preferred polymers and oligomers of Formula I for are
those wherein R$^1$ is (i) hydrogen, a polar group (PL), or a
non-polar group (NPL), and R$^2$ is -A$_1$-R$^1$, wherein A$_1$ is as
defined above and is optionally substituted with one or more
polar (PL) group(s), one or more non-polar (NPL) group(s),
or a combination of one or more polar (PL) group(s) and one
or more non-polar (NPL) group(s); or (ii) A'-s- and R$^2$ is
-A$_1$-s-A', wherein A' is aryl or heteroaryl, either of which is
optionally substituted with one or more polar (PL) group(s),
one or more non-polar (NPL) group(s), or a combination of
one or more polar (PL) group(s) and one or more non-polar
(NPL) group(s). More preferred are those oligomers of Formula I wherein R$^1$ is hydrogen or a polar group (PL), and R$^2$
is -A$_1$-R$^1$, where A$_1$ is optionally substituted with one or more
polar (PL) group(s). Especially preferred are those oligomers
wherein R$^1$ is a polar (PL) group, such as halo, and R$^2$ is
-A$_1$-R$^1$, where A$_1$ is optionally substituted with one or more
polar (PL) group(s).

In some aspects of the invention, preferred polymers and
oligomers of Formula I are those wherein NPL is —B(OR$^4$)$_2$,
wherein R$^4$ is hydrogen, alkyl, alkenyl, cycloalkyl, aryl, or
heteroaryl, any of which is optionally substituted with one or
more alkyl or halo groups.

In other aspects, preferred polymers and oligomers of Formula I include those wherein NPL is —(NR$^{3'}$)$_{q1NPL}$—
U$^{NPL}$—(CH$_2$)$_{pNPL}$—(NR$^{3''}$)$_{q2NPL}$—R$^4$, and R$^3$, R$^{3'}$, R$^{3''}$, R$^4$,
U$^{NPL}$, pNPL, q1NPL and q2NPL are as defined above.

Preferred values for each of R$^3$, R$^{3'}$, and R$^{3''}$ are hydrogen,
C$_1$-C$_6$ alkyl, and C$_1$-C$_6$ alkoxy. Hydrogen is an especially
preferred value for R$^3$, R$^{3'}$, and R$^{3''}$.

Preferred values of R$^4$ are hydrogen, C$_1$-C$_{10}$ alkyl, C$_3$-C$_{18}$
branched alkyl, C$_2$-C$_{10}$ alkenyl, C$_2$-C$_{10}$ alkynyl, C$_3$-C$_8$
cycloalkyl, C$_6$-C$_{10}$ aryl, and heteroaryl, any of which is
optionally substituted with one or more C$_1$-C$_6$ alkyl or halo
groups. Values of R$^4$ that are especially preferred are C$_1$-C$_{10}$
alkyl, C$_3$-C$_{18}$ branched alkyl, C$_2$-C$_{10}$ alkenyl, C$_2$-C$_{10}$ alkynyl,
and C$_6$-C$_{10}$ aryl, especially phenyl.

Preferred values of U$^{NPL}$ are O, S, S(=O), S(=O)$_2$, NH,
—(C=O)—, —(C=O)—N=N—NH—, —(C=O)—
NH—N=N—, —N=N—NH—, —C(=N—N(R$^3$)$_2$)—,
—C(=NR$^3$)—, —C(=O)O—, —C(=O)S—, —C(=S)—,
—O—P(=O)$_2$O—, —R$^3$O—, —R$^3$S—, —S—C=N— and
—(C=O)—NR$^3$—O—, wherein groups with two chemically nonequivalent termini can adopt both possible orientations. Especially preferred values of U$^{NPL}$ are O, NH,
—(C=O)—, —(C=O)—N=N—NH—, —(C=O)—
NH—N=N—, —N=N—NH—, —C(=N—N(R$^3$)$_2$)—, —C(=NR³)—, —C(=O)O—, and —R³O—. Preferred polymers and oligomers of Formula I also include those in which $U^{NPL}$ is absent.

In some aspects of the invention, preferred polymers and oligomers of Formula I are those wherein $U^{NPL}$ is =O—P(=O)$_2$O—.

Preferred values of pNPL are 0 to 6; values of pNPL of 0 to 4 are especially preferred, with values of pNPL of 0 to 2 most preferred.

Preferred values of q1NPL and q2NPL are 0 or 1. Values of q1NPL and q2NPL of 0 or 1 are especially preferred, with a value of 0 being the most preferred for each of q1 NPL and q2NPL.

In preferred polymers and oligomers of Formula I, the alkylene chain in NPL is unsubstituted or unsaturated.

Especially preferred values of NPL for polymers and oligomers of Formula I include $C_1$-$C_{10}$ alkoxy, $C_1$-$C_{10}$ alkylthio, and $C_1$-$C_{10}$ alkylamino.

In some aspects of the invention, preferred polymer and oligomers of Formula I for use in the disclosed methods include those wherein PL is halo. Especially preferred values of PL are bromo and iodo.

In other aspects of the invention, preferred polymers and oligomers of Formula I are those wherein PL is —(NR$^{5'}$)$_{q1PL}$—U$^{PL}$—(CH$_2$)$_{pPL}$—(NR$^{5''}$)$_{q2PL}$—V, and R$^5$, R$^{5'}$, R$^{5''}$, V, U$^{PL}$, pPL, q1PL and q2PL are as defined above.

Preferred values for R$^5$, R$^{5'}$, and R$^{5''}$ are hydrogen, $C_1$-$C_6$ alkyl, and $C_1$-$C_6$ alkoxy. Hydrogen is an especially preferred value for each of R$^5$, R$^{5'}$, and R$^{5''}$.

Preferred values of $U^{PL}$ are O, S, S(=O), S(=O)$_2$, NH, —(C=O)—, —(C=O)—N=N—NH—, —(C=O)—NH—N=N—, —N=N—NH—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —(C=O)—NR$^5$—O—, wherein groups with two chemically nonequivalent termini can adopt both possible orientations. Especially preferred values of $U^{PL}$ are O, NH, —(C=O)—, —(C=O)—N=N—NH—, —(C=O)—NH—N=N—, N=N—NH—, —C(=N—N(R$^5$)$_2$)—, —C(=NR$^5$)—, —C(=O)O—, and —R$^5$O—. Preferred polymers and oligomers of Formula I are also those in which $U^{PL}$ is absent.

In some aspects of the invention, preferred polymers and oligomers of Formula I are those wherein $U^{PL}$ is =O—P(=O)$_2$O—.

Preferred values of V are nitro, cyano, amino, hydroxyl, $C_1$-$C_6$ alkoxy, $C_1$-$C_6$ alkylthio, $C_1$-$C_6$ alkylamino, $C_1$-$C_6$ dialkylamino, —NH(CH$_2$)$_p$NH$_2$, —N(CH$_2$CH$_2$NH$_2$)$_2$, diazamino, amidino, guanidino, guanyl semicarbazone, $C_6$-$C_{10}$ aryl, heterocycle, and heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanidino, guanyl, aminosulfonyl, aminoalkoxy, lower acylamino, or benzyloxycarbonyl.

Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadizaole, 1,2,5-oxadiazole, 1,3,4-oxadiazole, pyridine, and 2-aminopyridine.

Especially preferred values of V are amino, $C_1$-$C_6$ alkylamino, $C_1$-$C_6$ dialkylamino, —NH(CH$_2$)$_p$NH$_2$, —N(CH$_2$CH$_2$NH$_2$)$_2$, diazamino, amidino, guanidino, guanyl, and semicarbazone, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanidino, guanyl, aminosulfonyl, aminoalkoxy, lower acylamino, or benzyloxycarbonyl.

Even more preferred values of V are amino, $C_1$-$C_6$ alkylamino, —NH(CH$_2$)$_p$NH$_2$, —N(CH$_2$CH$_2$NH$_2$)$_2$, diazamino, amidino, and guanidino, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanyl, guanidine, or aminoalkoxy.

Preferred values of pPL are 0 to 6; values of pPL of 0 to 4 are especially preferred, with values of pPL of 0 to 2 especially preferred.

Preferred values of q1PL and q2PL are 0 or 1. Values of q1PL and q2PL of 0 or 1 are especially preferred, with a value of 0 being especially preferred for each of q1PL and q2PL.

In preferred polymers and oligomers of Formula I, the alkylene chain in PL is optionally substituted with one or more amino or hydroxy groups.

Preferred polymers of Formula I are those in which m is 1 to about 500. Especially preferred are those polymers of Formula I wherein m is 1 to about 100, or wherein m is 1 to about 50.

Oligomers of Formula I that are preferred are those wherein m is 1 to about 25; more preferred are those in which m is 1 to about 20, or in which m is 1 to about 10, or in which m is 1 to about 5. Especially preferred are those oligomers of Formula I wherein m is 1, 2 or 3.

In some aspects of the invention, preferred polymers and oligomers of Formula I are those wherein:

$A_1$ and $A_2$ are independently optionally substituted o-, m-, or p-phenylene, wherein
  (i) one of $A_1$ or $A_2$ is substituted with one or more polar (PL) group(s) and one or more nonpolar (NPL) group(s), and the other of $A_1$ or $A_2$ is unsubstituted; or
  (ii) one of $A_1$ or $A_2$ is substituted with one or more polar (PL) group(s) and the other of $A_1$ or $A_2$ is unsubstituted; or
  (iii) one of $A_1$ or $A_2$ is substituted with one or more polar (PL) group(s) and the other of $A_1$ or $A_2$ is substituted with one or more nonpolar (NPL) group(s);

s is —C≡C—;

$R^1$ is
  (i) hydrogen, a polar group (PL), or a non-polar group (NPL), and $R^2$ is -$A_1$-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or
  (ii) A'-s- and $R^2$ is -$A_1$-s-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s);

NPL is —(NR$^3$)$_{q1NPL}$—U$^{NPL}$—(CH$_2$)$_{pNPL}$—(NR$^{3''}$)$_{q2NPL}$—R$^4$, wherein R$^3$, R$^{3'}$, and R$^{3''}$ are independently selected from the group consisting of hydrogen, $C_1$-$C_6$ alkyl, and $C_1$-$C_6$ alkoxy;

R$^4$ is selected from the group consisting of hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups;

$U^{NPL}$ is absent or selected from the group consisting of O, S, S(=O), S(=O)$_2$, NH, —(C=O)—, —(C=O)—N=N—NH—, —(C=O)—NH—N=N—, —N=N—NH—, —C(=N—N(R$^3$)$_2$)—, —C(=NR$^3$)—, —C(=O)O—, —C(=O)S—, —C(=S)—, —O—P(=O)$_2$O—, —R$^3$—O—, —R$^3$—S—, —S—C=N— and —(C=O)—NR$^3$—O—, wherein groups with two chemically nonequivalent termini can adopt both possible orientations;

the alkylene chain —(CH$_2$)$_{pNPL}$— is optionally substituted with one or more amino or hydroxyl groups;

pNPL is 0 to 6;

q1NPL and q2NPL are independently 0 or 1;

PL is halo or —(NR$^{5'}$)$_{q1PL}$—U$^{PL}$—(CH$_2$)$_{pPL}$—(NR$^{5''}$)$_{q2PL}$—V, wherein;

R$^5$, R$^{5'}$, and R$^{5''}$ are independently selected from the group consisting of hydrogen, C$_1$-C$_6$ alkyl, and C$_1$-C$_6$ alkoxy;

U$^{PL}$ is absent or selected from the group consisting of O, S, S(=O), S(=O)$_2$, NH, —(C=O)—, —(C=O)—N=N—NH—, —(C=O)—NH—N=N—, —N=N—NH—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —(C=O)—NR$^5$—O—, wherein groups with two chemically nonequivalent termini can adopt both possible orientations;

V is selected from the group consisting of nitro, cyano, amino, hydroxyl, C$_1$-C$_6$ alkoxy, C$_1$-C$_6$ alkylthio, C$_1$-C$_6$ alkylamino, C$_1$-C$_6$ dialkylamino, —NH(CH$_2$)$_p$NH$_2$, —N(CH$_2$CH$_2$NH$_2$)$_2$, diazamino, amidino, guanidino, guanyl, semicarbazone, C$_6$-C$_{10}$ aryl, heterocycle, and heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanidino, guanyl, aminosulfonyl, aminoalkoxy, lower acylamino, or benzyloxycarbonyl;

the alkylene chain —(CH$_2$)$_{pPL}$— is optionally substituted with one or more amino or hydroxyl groups;

pPL is 0 to 6;

q1PL and q2PL are independently 0 or 1; and m is 1 to about 5.

Polyaryl and polyarylalkynyl oligomers of the present invention also include oligomers of Formula Ia,

$$R^1-A_1-s-A_2-s-A_1-R^2 \quad (Ia)$$

or an acceptable salt or solvate thereof, wherein:

A$_1$ and A$_2$ are independently optionally substituted arylene or optionally substituted heteroarylene, wherein:

(i) A$_1$ and A$_2$ are independently optionally substituted with one or more polar (PL) group(s), one or more non-polar (NPL) group(s), or a combination of one or more polar (PL) group(s) and one or more non-polar (NPL) group(s); or (ii) one of A$_1$ or A$_2$ is as defined above and is optionally substituted with one or more polar (PL) group(s), one or more non-polar (NPL) group(s), or a combination of one or more polar (PL) group(s) and one or more non-polar (NPL) group(s); and the other of A$_1$ or A$_2$ is the group —C≡C(CH$_2$)$_p$C≡C—, wherein p is 0 to 8, and the —(CH$_2$)$_p$— alkylene chain is optionally substituted with one or more amino or hydroxyl groups;

s is absent, or is —CH=CH— or —C≡C—;

R$^1$ is hydrogen, a polar group (PL), a non-polar group (NPL), or -s-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s);

R$^2$ is R$^1$;

NPL is a nonpolar group independently selected from —B(OR$^4$)$_2$ or —(NR$^{3'}$)$_{q1NPL}$—U$^{NPL}$—(CH$_2$)$_{pNPL}$—(NR$^{3''}$)$_{q2NPL}$—R$^4$, wherein R$^3$, R$^{3'}$, and R$^{3''}$ are independently selected from the group consisting of hydrogen, alkyl, and alkoxy;

R$^4$ is selected from the group consisting of hydrogen, alkyl, alkenyl, alkynyl, cycloalkyl, aryl, and heteroaryl, any of which is optionally substituted with one or more alkyl or halo groups;

U$^{NPL}$ is absent or selected from the group consisting of O, S, S(=O), S(=O)$_2$, NR$^3$, —(C=O)—, —(C=O)—N=N—NR$^3$—, —(C=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$—O—, —R$^3$—S—, —S—C=N— and —(C=O)—NR$^3$—O—, wherein groups with two chemically nonequivalent termini can adopt both possible orientations;

the alkylene chain —(CH$_2$)$_{pNPL}$— is optionally substituted with one or more amino or hydroxyl groups, or the alkylene chain is unsaturated;

pNPL is 0 to 8;

q1NPL and q2NPL are independently 0 to 2;

PL is a polar group selected from the group consisting of halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5''}$)$_{q2PL}$—V, wherein;

R$^5$, R$^{5'}$, and R$^{5''}$ are independently selected from the group consisting of hydrogen, alkyl, and alkoxy;

U$^{PL}$ is absent or selected from the group consisting of O, S, S(=O), S(=O)$_2$, NR$^5$, —(C=O)—, —(C=O)—N=N—NR$^5$—, —(C=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —(C=O)—NR$^5$—O—, wherein groups with two chemically nonequivalent termini can adopt both possible orientations;

V is selected from the group consisting of nitro, cyano, amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone, aryl, heterocycle and heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanidino, guanyl, aminosulfonyl, aminoalkoxy, aminoalkylthio, lower acylamino, or benzyloxycarbonyl;

the alkylene chain —(CH$_2$)$_{pPL}$— is optionally substituted with one or more amino or hydroxyl groups, or the alkylene chain is unsaturated;

pPL is 0 to 8; and q1PL and q2PL are independently 0 to 2;

with the proviso that if A$_1$ and A$_2$ are thiophene, the polar groups cannot be 3-(propionic acid) or methoxy(diethoxy) ethyl and the nonpolar group cannot be n-dodecyl.

A preferred group of oligomers falling within the scope of the present invention include oligomers of Formula Ia wherein A$_1$ and A$_2$ are independently optionally substituted o-, m- or p-phenylene. Oligomers of Formula Ia wherein A$_1$ and A$_2$ are optionally substituted m-phenylene are especially preferred. Also preferred are oligomers of Formula Ia wherein one of A$_1$ or A$_2$ is o-, m-, or p-phenylene, and the other of A$_1$ or A$_2$ is heteroarylene. Preferred heteroarylene groups include, but are not limited to, pyridinyl, pyrimidinyl, and pyrazinyl.

Especially preferred oligomers of Formula Ia are those wherein $A_1$ and $A_2$ are optionally substituted m-phenylene.

Preferred oligomers of Formula Ia include those wherein one of $A_1$ or $A_2$ is substituted with one or more polar (PL) group(s) and one or more nonpolar (NPL) group(s) and the other of $A_1$ or $A_2$ is unsubstituted. Preferred oligomers also include those wherein one of $A_1$ or $A_2$ is substituted with one or more polar (PL) group(s) and the other of A or $A_2$ is unsubstituted.

Preferred oligomers include those wherein s is —C≡C—.

A preferred group of oligomers having Formula Ia include oligomers wherein $R^1$ is hydrogen, a polar group (PL), or a non-polar group (NPL); and $R^2$ is $R^1$.

Especially preferred are oligomers of Formula Ia wherein $R^1$ is selected from the group consisting of hydrogen, halo, nitro, cyano, $C_1$-$C_6$ alkoxy, $C_1$-$C_6$ alkoxycarbonyl, and benzyloxycarbonyl. Oligomers of Formula Ia wherein $R^1$ and $R^2$ are halo are especially preferred.

Preferred oligomers that fall within the scope of Formula Ia include those wherein NPL is —(NR$^3$)$_{q1NPL}$—U—(CH$_2$)$_{pNPL}$—(NR$^{3''}$)$_{q2NPL}$—$R^4$, and $R^3$, $R^{3'}$, $R^{3''}$, $R^4$, $U^{NPL}$, pNPL, q1NPL and q2NPL are as defined above. Those oligomers wherein q1NPL and q2NPL are independently 0 or 1 are preferred.

Preferred $R^3$, $R^{3'}$, and $R^{3''}$ groups include hydrogen and $C_1$-$C_4$ alkyl. Especially preferred are those oligomers of Formula Ia wherein $R^3$, $R^{3'}$, and $R^{3''}$ are each hydrogen.

Preferred $R^4$ groups include hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups. Especially preferred are oligomers wherein $R^4$ is $C_1$-$C_{10}$ alkyl, $C_3$-$C_{18}$ branched alkyl, $C_2$-$C_{10}$ alkenyl, $C_2$-$C_{10}$ alkynyl, or $C_6$-$C_{10}$ aryl, especially phenyl. Oligomers wherein $R^4$ is hydrogen, $C_1$-$C_{10}$ alkyl, and $C_3$-$C_{18}$ branched alkyl, any of which is optionally substituted with one or more $C_1$-$C_4$ alkyl or halo groups, are especially preferred.

Preferred oligomers of Formula Ia are those wherein $U^{NPL}$ is O, S, S(=O), S(=O)$_2$, NH, —(C=O)—, —(C=O)—N=N—NH—, —(C=O)—NH—N=N—, —N=N—NH—, —C(=N—N($R^3$)$_2$)—, —C(=N$R^3$)—, —C(=O)O—, —C(=O)S—, —C(=S)—, —O—P(=O)$_2$O—, —$R^3$O—, —$R^3$S—, —S—C=N— or —(C=O)—N$R^3$—O—, wherein groups with two chemically nonequivalent termini can adopt both possible orientations. Oligomers of Formula Ia wherein $U^{NPL}$ is O, S, or —(C=O)— are especially preferred. Oligomers of Formula Ia wherein $U^{NPL}$ is absent are also preferred.

Preferred oligomers are those wherein NPL is n-pentoxy, n-butoxy, sec-butoxy, tert-butoxy, propyloxy, ethyloxy, methoxy, or phenoxy.

Preferred oligomers of Formula Ia are those wherein one or more PL are halo, especially bromo or iodo.

Preferred oligomers that fall within the scope of Formula Ia also include those wherein PL is —(NR$^{5'}$)$_{q1PL}$—$U^{PL}$—(CH$_2$)$_{pPL}$—(NR$^{5''}$)$_{q2PL}$—V, and $R^5$, $R^{5'}$, $R^{5''}$, V, $U^{PL}$, pPL, and q1PL and q2PL are as defined above.

Preferred values for $R^5$, $R^{5'}$, and $R^{5''}$ are hydrogen, $C_1$-$C_6$ alkyl, and $C_1$-$C_6$ alkoxy. Hydrogen is an especially preferred value for each of $R^5$, $R^{5'}$, and $R^{5''}$, Preferred values of $U^{PL}$ are O, S, S(=O), S(=O)$_2$, NH, —(C=O)—, —(C=O)—N=N—NH—, —(C=O)—NH—N=N—, —N=N—NH—, —C(=N—N($R^5$)$_2$)—, —C(=N$R^5$)—, —C(=O)O—, —C(=O)S—, —C(=S)—, —$R^5$O—, —$R^5$S—, —S—C=N— and —(C=O)—N$R^5$—O—, wherein groups with two chemically nonequivalent termini can adopt both possible orientations. Also preferred are oligomers of Formula Ia wherein $U^{PL}$ is absent. Oligomers of Formula Ia wherein $U^{PL}$ is O, S, —(C=O)—, —C(=O)O—, —C(=O)S—, or absent, are preferred. Those oligomers wherein $U^{PL}$ is —(C=O)— or absent are especially preferred.

In some aspects of the invention, preferred polymers and oligomers of Formula Ia are those wherein $U^{PL}$ is —O—P(=O)$_2$O—.

Preferred oligomers of Formula Ia are those wherein q1PL and q2PL are independently 0 or 1.

Preferred oligomers of Formula Ia are those wherein V is nitro, cyano, amino, hydroxyl, $C_1$-$C_6$ alkoxy, $C_1$-$C_6$ alkylthio, $C_1$-$C_6$ alkylamino, $C_1$-$C_6$ dialkylamino, —NH(CH$_2$)$_p$NH$_2$, —N(CH$_2$CH$_2$NH$_2$)$_2$, diazamino, amidino, guanidino, guanyl, semicarbazone, heterocycle, or heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanyl, guanidine, or aminoalkoxy. Especially preferred values of V include amino, $C_1$-$C_6$ alkylamino, $C_1$-$C_6$ dialkylamino, —NH(CH$_2$)$_p$NH$_2$, —N(CH$_2$CH$_2$NH$_2$)$_2$, diazamino, amidino, guanidino, or guanyl, any of which is optionally substituted with one or more of amino, halo, —NH(CH$_2$)$_p$NH$_2$, —N(CH$_2$CH$_2$NH$_2$)$_2$, amidino, guanyl, guanidine, or aminoalkoxy.

Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadizaole, 3-amino-1,2,4-oxadizaole, 1,2,5-oxadiazole, 1,3,4-oxadiazole, pyridine, or 2-aminopyridine.

Especially preferred oligomers include those wherein PL is halo, guanidinomethyl, guanidinoethyl, guanidinopropyl, aminomethyl, aminoethyl, aminopropyl, aminoethylaminocarbonyl, or aminomethylaminocarbonyl.

Preferred oligomers of Formula Ia are those wherein pPL is 0 to 4. Especially preferred are those oligomers wherein pPL is 0 to 2.

Exemplary structures of oligomers of Formula Ia within the scope of the invention include the following:

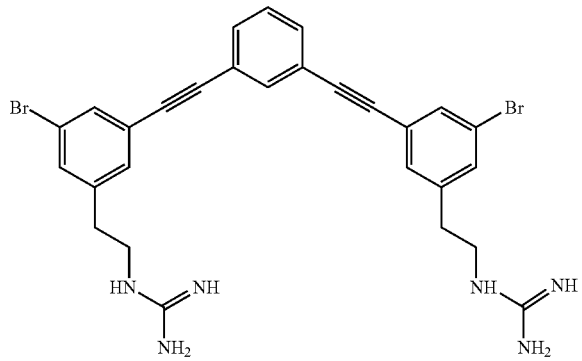

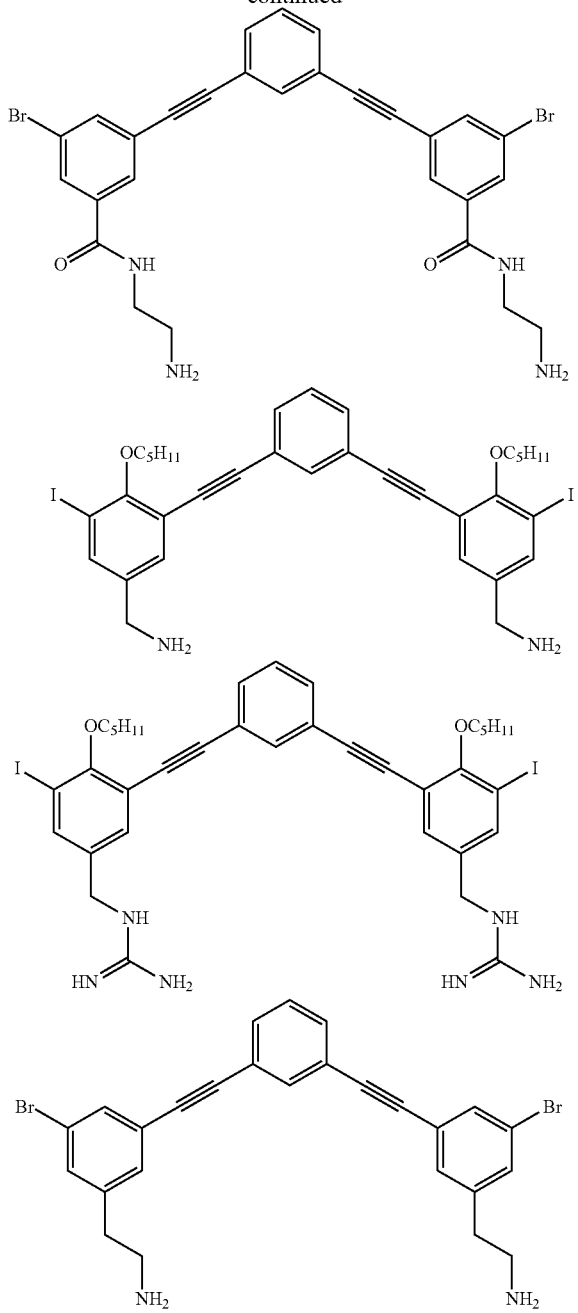

or physiologically acceptable salts thereof.

In some aspects, the present invention is directed to oligomers of Formula Ia, and to compositions comprising oligomers of Formula Ia. Compositions of oligomers of Formula Ia include, but are not limited to, pharmaceutical compositions comprising an oligomer of Formula Ia and a pharmaceutically acceptable carrier or diluent.

In some aspects of the invention, the polymers and oligomers of Formula I or Formula Ia are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process.

When any variable occurs more than one time in any constituent or in Formula I or Formula Ia, its definition on each occurrence is independent of its definition at every other occurrence. Also, combinations of substituents and/or variables are permissible only if such combinations result in stable compounds.

It is understood that the present invention encompasses the use of stereoisomers, diastereomers and optical isomers having Formula I or Formula Ia, as well as mixtures thereof, for treating microbial infections, killing or inhibiting the growth of a microorganism, and providing an antidote to low molecular weight heparin overdose in an animal. Additionally, it is understood that stereoisomers, diastereomers and optical isomers having Formula I or Formula Ia, and mixtures thereof, are within the scope of the invention. By way of non-limiting example, the mixture can be a racemate or the mixture may comprise unequal proportions of one particular stereoisomer over the other. Thus, in some aspects of the invention, the polymers and oligomers of the invention are provided as mixtures that are racemates. Additionally, the polymers and oligomers of Formulae I and Ia can be provided as a substantially pure stereoisomers, diastereomers and optical isomers. Thus, in some aspects of the invention, the polymers and oligomers are provided as substantially pure stereoisomers, diastereomers, or optical isomers.

In another aspect of the invention, the polymers and oligomers of Formulae I and Ia are provided in the form of an acceptable salt (i.e., a pharmaceutically acceptable salt) for treating microbial infections, killing or inhibiting the growth of a microorganism, and providing an antidote to low molecular weight heparin overdose in an animal. Polymer or oligomer salts can be provided for pharmaceutical use, or as an intermediate in preparing the pharmaceutically desired form of the polymer or oligomer. One polymer or oligomer salt that is considered to be acceptable is the hydrochloride acid addition salt. Hydrochloride acid addition salts are often acceptable salts when the pharmaceutically active agent has an amine group that can be protonated. Since a polymer or oligomer of the invention may be polyionic, such as a polyamine, the acceptable polymer or oligomer salt can be provided in the form of a poly(amine hydrochloride).

Unless otherwise defined, the terms below have the following meanings.

The term "alkyl" as used herein by itself or as part of another group refers to both straight and branched chain radicals from 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" as used herein refers to a straight or branched chain radical of 2-20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" as used herein refers to a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

The term "alkylene" as used herein refers to an alkyl linking group, i.e., an alkyl group that links one group to another group in a molecule.

The term "alkoxy" as used herein refers to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length, and even more preferred 1 to 6 carbon atoms in length.

The term "aryl" as used herein by itself or as part of another group refers to monocyclic or bicyclic aromatic groups containing from 6 to 12 carbons in the ring portion, preferably 6-10 carbons in the ring portion, such as the carbocyclic groups phenyl, naphthyl or tetrahydronaphthyl. The term "aryl" can represent carbocyclic aryl groups, such as phenyl, naphthyl or tetrahydronaphthyl, as well as heterocyclic aryl ("heteroaryl") groups, such as pyridyl, pyrimidinyl, pyridazinyl, furyl, and pyranyl.

The term "arylene" as used herein by itself or as part of another group refers to an aryl linking group, i.e., an aryl group that links one group to another group in a molecule.

The term "cycloalkyl" as used herein by itself or as part of another group refers to cycloalkyl groups containing 3 to 9 carbon atoms, more preferably, 3 to 8 carbon atoms. Typical examples are cyclopropyl, cyclobutyl, cyclopentyl, cyclohexyl, cycloheptyl, cyclooctyl and cyclononyl.

The term "halogen" or "halo" as used herein by itself or as part of another group refers to chlorine, bromine, fluorine or iodine.

The term "heteroaryl" as used herein refers to groups having 5 to 14 ring atoms; 6, 10 or 14 π-electrons shared in a cyclic array; and containing carbon atoms and 1, 2 or 3 oxygen, nitrogen or sulfur heteroatoms. Examples of heteroaryl groups include thienyl, imadizolyl, oxadiazolyl, isoxazolyl, triazolyl, pyridyl, pyrimidinyl, pyridazinyl, furyl, pyranyl, thianthrenyl, pyrazolyl, pyrazinyl, indolizinyl, isoindolyl, isobenzofuranyl, benzoxazolyl, xanthenyl, 2H-pyrrolyl, pyrrolyl, 3H-indolyl, indolyl, indazolyl, purinyl, 4H-quinolizinyl, isoquinolyl, quinolyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, and phenoxazinyl groups. Especially preferred heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

The term "heteroarylene" as used herein by itself or as part of another group refers to a heteroaryl linking group, i.e., a heteroaryl group that links one group to another group in a molecule.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, olidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms, The term "alkylthio" as used herein by itself or as part of another group refers to a thio group which is substituted with one alkyl group having from 1 to 6 carbon atoms.

The term "lower acylamino" as used herein by itself or as part of an other group refers to an amino group substituted with a $C_1$-$C_6$ alkylcarbonyl group.

The term "chemically nonequivalent termini" as used herein refers to a functional group such as an ester, amide, sulfonamide, or N-hydroxyoxime that, when reversing the orientation of the functional group (e.g., —(C=O)O—) produces different chemical entities (e.g., —$R^1$C(=O)O$R^2$— vs. —$R^1$OC(=O)$R^2$—).

The facially amphiphilic of the present invention possess antimicrobial activity and thus, for example, can be used in a method of treating microbial infections in an animal.

Thus, in some aspects, the present invention is directed to a method of treating a microbial infection in an animal in need thereof, the method comprising administering to the animal an effective amount of a pharmaceutical composition comprising a polymer or oligomer of Formula I as defined above, or an acceptable salt or solvate thereof, and a pharmaceutically acceptable carrier or diluent.

The invention is also directed to a method of treating a microbial infection in an animal in need thereof, the method comprising administering to the animal an effective amount of a pharmaceutical composition comprising a polymer or oligomer of Formula Ia as defined above, or an acceptable salt or solvate thereof, and a pharmaceutically acceptable carrier or diluent.

The polymers and oligomers of the invention are used to treat a microbial infection caused by any type of microorganism, including, but not limited to, bacteria, algae, fungi, yeast, mycoplasmas, mycobacterial, parasites and protozoa. The polymers and oligomers of the present invention are therefore effective in treating bacterial infections, fungal infections, viral infections, yeast infections, mycoplasmid infections, mycobacterial infections, or protozoal infections. In some aspects of the invention, the microbial infection to be treated is a bacterial infection, a fungal infection, or a viral infection.

Thus, in some aspects, the present invention is directed to a method of treating a bacterial infection, a fungal infection, or a viral infection in an animal in need thereof, the method comprising administering to the animal an effective amount of a pharmaceutical composition comprising a polymer or oligomer of Formula I, as defined above, or an acceptable salt or solvate thereof, and a pharmaceutically acceptable carrier or diluent.

In other aspects, the present invention is directed to a method of treating a bacterial infection, a fungal infection, or a viral infection in an animal in need thereof, the method comprising administering to the animal an effective amount of a pharmaceutical composition comprising a polymer or oligomer of Formula Ia, as defined above, or an acceptable salt or solvate thereof, and a pharmaceutically acceptable carrier or diluent.

The polymers and oligomers of the present invention can be used to kill or inhibit the growth of any of the following microbes or mixtures of the following microbes, or, alternatively, can be administered to treat local and/or systemic microbial infections or illnesses caused by the following microbes or mixtures of the following microbes: Gram-positive cocci, for example Staphylococci (*Staph. aureus, Staph. epidermidis*) and Streptococci (*Strept. agalactiae, Strept. faecalis, Strept. pneumoniae, Strept. pyogenes*); Gram-negative cocci (*Neisseria gonorrhoeae* and *Yersinia pestis*) and Gram-negative rods such as Enterobacteriaceae, for example *Escherichia coli, Hamophilus influenzae, Citrobacter* (*Citrob. freundii, Citrob. divernis*), *Salmonella* and *Shigella*, and *Francisella* (*Francisella tularensis*); Gram-positive rods such as *Bacillus* (*Bacillus anthracis, Bacillus thuringenesis*); furthermore *Klebsiella* (*Klebs. pneumoniae, Klebs. oxytoca*), *Enterobacter* (*Ent. aerogenes, Ent. agglomerans*), *Hafnia, Serratia* (*Serr. marcescens*), *Proteus* (*Pr. mirabilis, Pr. rettgeri, Pr. vulgaris*), *Providencia, Yersinia*, and the genus *Acinetobacter*. Furthermore, the anti-microbial spectrum of the polymers and oligomers of the invention covers the genus *Pseudomonas* (*Ps. aeruginosa, Ps. maltophilia*) and strictly anaerobic bacteria such as, for example, *Bacteroides fragilis*, representatives of the genus *Peptococcus, Peptostreptococcus* and the genus *Clostridium*; furthermore Mycoplasmas (*M. pneumoniae, M. hominis, Ureaplasma urealyticum*) as well as *Mycobacteria*, for example *Mycobacterium tuberculosis*. This list of microbes is purely illustrative and is in no way to be interpreted as restrictive.

Examples of microbial infections or illness that can be treated by administration of the polymers and oligomers of the invention include, but are not limited to, microbial infections or illnesses in humans such as, for example, otitis, pharyngitis, pneumonia, peritonitis, pyelonephritis, cystitis, endocarditis, systemic infections, bronchitis (acute and chronic), septic infections, illnesses of the upper airways, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmon, wound infections, infected burns, burns, infections in the mouth, infections after dental operations, osteomyelitis, septic arthritis, cholecystitis, peritonitis with appendicitis, cholangitis, intraabdominal abscesses, pancreatitis, sinusitis, mastoiditis, mastitis, tonsileitis, typhoid, meningitis and infections of the nervous system, salpingitis, endometritis, genital infections, pelveoperitonitis and eye infections.

Examples of viral infections that can be treated by administration of the polymers and oligomers of the invention include, but are not limited to, viral infections caused by human immunodeficiency virus (HIV-1, HIV-2), hepatitis virus (e.g., hepatitis A, hepatitis B, hepatitis C, hepatitis D, and hepatitis E viruses), herpesviruses (e.g., herpes simplex virus types 1 and 2, varicella-zoster virus, cytomegalovirus, Epstein Barr virus, and human herpes viruses types 6, 7, and 8), influenza virus, respiratory syncytial virus (RSV), vaccinia virus, and adenoviruses. This list is purely illustrative and is in no way to be interpreted as restrictive.

Examples of fungal infections or illnesses that can be treated by administration of the polymers and oligomers of the present invention include, but are not limited to, fungal infections caused by Chytridiomycetes, Hyphochrytridiomycetes, Plasmodiophoromycetes, Oomycetes, Zygomycetes, Ascomycetes, and Basidiomycetes. Fungal infections which can be inhibited or treated with compositions of the polymers and oligomers provided herein include, but are not limited to: Candidiasis, including, but not limited to, onchomycosis, chronic mucocutaneous candidiasis, oral candidiasis, epiglottistis, esophagitis, gastrointestinal infections, genitourinary infections, for example, caused by any *Candida* species, including, but not limited to, *Candida albicans, Candida tropicalis, Candida* (*Torulopsis*) *glabrata, Candida parapsilosis, Candida lusitaneae, Candida rugosa* and *Candida pseudotropicalis*; Aspergillosis, including, but not limited to, granulocytopenia caused, for example, by, *Aspergillus* spp. Including, but not limited, to *Aspergillus fumigatus, Aspergillus favus, Aspergillus niger* and *Aspergillus terreus*; Zygomycosis, including, but not limited to, pulmonary, sinus and rhinocerebral infections caused by, for example, zygomycetes such as *Mucor, Rhizopus* spp., *Absidia, Rhizomucor, Cunningamella, Saksenaea, Basidobolus* and *Conidobolus*; Cryptococcosis, including, but not limited, to infections of the central nervous system, e.g., meningitis, and infections of the respiratory tract caused by, for example, *Cryptococcus neoformans*; Trichosporonosis caused by, for example, *Trichosporon beigelii*; Pseudallescheriasis caused by, for example, *Pseudallescheria boydii*; Fusarium infection caused by, for example, *Fusarium* such as *Fusarium solani, Fusarium moniliforme* and *Fusarium proliferartum*; and other infections such as those caused by, for example, *Penicillium* spp. (generalized subcutaneous abscesses), *Trichophyton* spp., for example, *Trichophyton mentagrophytes* and *Trichophyton rubrum, Stachybotrys* spp., for example, *S. chartarum, Drechslera, Bipolaris, Exserohilum* spp., *Paecilomyces lilacinum, Exophila jeanselmei* (cutaneous nodules), *Malassezia furfur* (folliculitis), *Alternaria* (cutaneous nodular lesions), *Aureobasidium pullulans* (splenic and disseminated infection), *Rhodotorula* spp. (disseminated infection), *Chaetomium* spp. (empyema), *Torulopsis candida* (fungemia), *Curvularia* spp. (nasopharnygeal infection), *Cunninghamella* spp. (pneumonia), *H. Capsulatum, B. dermatitidis, Coccidioides immitis, Sporothrix schenckii* and *Paracoccidioides brasiliensis, Geotrichum candidum* (disseminated infection). The polymers and oligomers of the present invention can also be used to kill or inhibit the growth of any of the fungi listed above. This list is purely illustrative and is in no way to be interpreted as restrictive.

The polymer or oligomer in any one of the above methods can be administered to a human subject. Thus, in some aspects of the invention, the polymer or oligomer is administered to a human.

The methods disclosed above also have veterinary applications and can be used to treat a wide variety of non-human vertebrates. Thus, in other aspects of the invention, the polymer or oligomer is administered in any one of the above methods to non-human vertebrates, such as wild, domestic, or farm animals, including, but not limited to, cattle, sheep, goats, pigs, dogs, cats, and poultry such as chicken, turkeys, quail, pigeons, ornamental birds and the like.

The following are examples of microbial infections in non-human vertebrates that can be treated by administering a polymer or oligomer of the invention: Pig: coli diarrhoea, enterotoxaemia, sepsis, dysentery, salmonellosis, metritis-mastitis-agalactiae syndrome, mastitis; ruminants (cattle, sheep, goat): diarrhoea, sepsis, bronchopneumonia, salmonellosis, pasteurellosis, mycoplasmosis, genital infections; horse: bronchopneumonias, joint ill, puerperal and post-puerperal infections, salmonellosis; dog and cat: bronchopneumonia, diarrhoea, dermatitis, otitis, urinary tract infections, prostatitis; poultry (chicken, turkey, quail, pigeon, ornamental birds and others): mycoplasmosis, *E. coli* infections, chronic respiratory tract illnesses, salmonellosis, pasteurellosis, psittacosis. This list is purely illustrative and is in no way to be interpreted as restrictive.

The polymers and oligomers of the present invention also inhibit the anticoagulation effects of heparin, in particular, low molecular weight heparin, and are useful as antidotes for hemorrhagic complications associated with low molecular weight heparin therapy.

Heparin has been commonly used as an anticoagulant and antithrombotic agent in the hospital setting. However, there are several pharmacokinetic parameters of standard heparin (SH) that complicate therapy. The high serum protein-binding activity of SH precludes subcutaneous administration and its rapid and unpredicatable plasma clearance necessitates constant monitoring of activated partial thromboplastin time to assess effectiveness (Turpie, A. G. G., *Am. Heart J.* 135: S329-S335 (1998)). The biological activity of SH is exerted by its binding to a specific coagulation factor (ATIII) at a unique pentasaccharide sequence distributed randomly along the heparin chain. Stable ternary complexes are then created with thrombin and factor Xa, which leads to their inactivation (Kandrotas, R. J., *Clin. Pharmacokinet.* 22:359-374 (1992)). The inactivation of ATIII/thrombin is caused by the binding of heparin to ATIII through its high affinity pentasaacharide sequence and to thrombin through an adjoining 13 saccharide sequence. The inactivation of the ATIII/Factor Xa complex is caused solely by ATIII binding at the high affinity pentasaccharide sequence. More recently, low molecular weight heparin derivatives (LMWH) have become the standard of care for the management of major vessel thrombotic conditions (Hirsh, J., and Levine, M. N., *Blood* 79:1-17 (1992)). LMWHs are formed by enzymatic or chemical cleavage of heparin and are effective factor Xa inhibitors because they contain the high affinity pentasaccharide sequence. However, they do not contain a sufficient number of additional saccharide units to be effective thrombin inhibitors (Hirsh, J., and Levine, M. N., *Blood* 79:1-17 (1992)). Nevertheless, LMWHs have gained popularity over standard heparin (SH) as antithrombotic agents because of their improved pharmacokinetics and more predictable anticoagulant responses to weight-adjusted doses Both SH and LMWH have a high net negative (anionic) charge. Hemorrhagic complications are associated with antithrombotic treatments with both agents and an overdose may result in serious bleeding. Protamine, by virtue of its positive charge, can neutralize the effects of the heparin but protamine therapy also has serious adverse side-effects including hypotension, pulmonary hypertension and impairment of certain blood cells, including platelets and lymphocytes (Wakefield, T. W., et al., *J. Surg. Res.* 63:280-286 (1996)). Importantly, protamine is not an effective antidote for the LMWHs (Diness, V. O. and Ostergaard, P. B., *Thromb. Haemost.* 56:318-322 (1986)), so patients experiencing hemorrhagic complications from LMWH can only be managed by supportive measures until the anticoagulant is cleared from the blood. Furthermore, the effects of LMWH typically last for 12-24 hours following subcutaneous administration so the lack of an effective antidote is a serious deficiency in its clinical use. The difference in the ability of protamine sulfate to neutralize the negative clinical effects of SH and LMWH is believed to be caused by differences in binding affinities of protamine sulfate to SH, LMWH and serum proteins (Diness, V. O. and Ostergaard, P. B., *Thromb. Haemost.* 56:318-322 (1986)). There is thus a strong need for the development of safe and effective antidotes for hemorrhagic complications associated with SH and LMWH antithrombotic therapies.

Thus, in some aspects, the present invention is directed to a method of providing an antidote to low molecular weight heparin overdose in an animal, the method comprising administering to the animal an effective amount of a pharmaceutical composition comprising a polymer or oligomer of Formula I, as defined above, or an acceptable salt or solvate thereof, and pharmaceutically acceptable carrier or diluent.

In some aspects, the present invention is also directed to a method of providing an antidote to low molecular weight heparin overdose in an animal, said method comprising administering to the animal an effective amount of a pharmaceutical composition comprising a polymer or oligomer of Formula Ia, as defined above, or an acceptable salt or solvate thereof, and a pharmaceutically acceptable carrier or diluent.

In some aspects of the invention, the polymers and oligomers of the present invention are useful as disinfectants. For example, coatings, paints, and adhesives are all exposed to microbial contamination and are used in locations where microbial growth is undesirable. Thus, the polymers and oligomers of the present invention can be incorporated into polishes, paints, sprays, or detergents formulated for application to surfaces to inhibit the growth of a bacterial species thereon. These surfaces include, but are not limited to surfaces, such as, countertops, desks, chairs, laboratory benches, tables, floors, bed stands, tools or equipment, doorknobs, and windows. The polymers and oligomers of the present invention can also be incorporated into soaps and hand lotions. The present cleansers, polishes, paints, sprays, soaps, hand lotions, or detergents contain a polymer or oligomer of the invention that provides a bacteriostatic property to them. They can optionally contain suitable solvent(s), carrier(s), thickeners, pigments, fragrances, deodorizers, emulsifiers, surfactants, wetting agents, waxes, or oils. For example, in some aspects of the invention, the polymers or oligomers are incoporated into a formulation for external use as a pharmaceutically acceptable skin cleanser, particularly for the surfaces of human hands. Cleansers, polishes, paints, sprays, soaps, hand lotions, and detergents and the like containing the antimicrobial polymers and oligomers of the present invention are useful in homes and institutions, particularly but not exclusively in hospital settings for the prevention of nosocomial infections.

In other aspects of the invention, the polymers and oligomers of the invention are useful as preservatives and are used in a method for killing or inhibiting the growth of a microbial species in a foodstuff. In some aspects of the invention, the polymers and oligomers are added to the foodstuff as a preservative. Foodstuffs that can be treated with a polymer or oligomer of the invention include, but are not limited to, non-acidic foods, such as mayonnaise or other egg products, potato products, and other vegetable or meat products. In some aspects, the polymer or oligomer for adding to the foodstuff is part of a comestible formulation that optionally includes a suitable medium or carrier for convenient mixing or dissolving into a particular foodstuff. The medium or carrier is preferably one that will not interfere with the familiar flavor of the food of interest, such as are known by the artisan skilled in food processing techniques.

In yet other aspects of the invention, the polymers and oligomers of the present invention provide a surface-mediated microbicide that only kills organisms in contact with the surface and are useful as surface-mediated disinfectants or preservatives.

Any object that is exposed to or susceptible to bacterial or microbial contamination can be treated with the polymers and oligomers of the present invention to provide a microbiocidal surface. To provide a microbiocidal surface, a polymer or oligomer of the invention can be attached to, applied on or incorporated into almost any substrate including but not limited to, woods, paper, synthetic polymers (plastics), natural and synthetic fibers, natural and synthetic rubbers, cloth, glasses and ceramics by appropriate methods, including by covalent bonding, ionic interaction, coulombic interaction, hydrogen bonding or cross-linking. Examples of synthetic polymers include elastically deformable polymers that are thermosetting or thermoplastic and include, but not limited to polypropylene, polyethylene, polyvinyl chloride, polyethylene terephthalate, polyurethane, polyesters such as polylactide, polyglycolide, rubbers such as polyisoprene, polybutadiene or latex, polytetrafluoroethylene, polysulfone and polyethylenesulfone polymers or copolymers. Examples of natural fibers include cotton, wool and linen.

The incidence of infection from food-borne pathogens is a continuing concern and antimicrobial packaging material, utensils and surfaces would be valuable. In the health care and medical device areas the utility of antimicrobial instruments, packaging and surfaces are obvious. Products used internally or externally in humans or animal health including, but not limited to, surgical gloves, implanted devices, sutures, catheters, dialysis membranes, water filters and implements, all can harbor and transmit pathogens.

Polymers and oligomers of the present invention can be incoporated into any of these devices or implements to provide surface-medicated antimicrobial surfaces that will kill or inhibit the growth of organisms in contact with the surface. For example, in some aspects of the present invention, the polymers and oligomers are incorporated into spinnable fibers for use in materials susceptible to bacterial contamination including, but not limited to, fabrics, surgical gowns, and carpets. Also, ophthalmic solutions and contact lenses easily become contaminated and cause ocular infections. Antimicrobial storage containers for contact lens and cleaning solutions incorporating polymers and oligomers of the present invention would thus be very valuable.

Thus, in some aspects, the present invention is directed to a method of killing or inhibiting the growth of a microorganism, said method comprising contacting the microorganism with an effective amount of a polymer or oligomer of Formula I as defined above, or an acceptable salt or solvate thereof.

In some aspects, the present invention is also directed to a method of killing or inhibiting the growth of a microorganism, said method comprising contacting the microorganism with an effective amount of a polymer or oligomer of Formula Ia as defined above, or an acceptable salt or solvate thereof.

The polymers and oligomers of the invention are designed to be capable of adopting amphiliphilic conformations that allow for the segregation of polar and nonpolar regions of the molecule into different spatial regions. Such conformations include, but are not limited to, repeating secondary structures such as α-helices and β-pleated sheet structures.

For example, in some aspects of the invention, the polymers and oligomers of Formulae I and Ia are homopolymers wherein, for example, one monomer is substituted with both a nonpolar and a polar substituent, or copolymers wherein, for example, one monomer is substituted with a polar substituent and the other monomer is substituted with a nonpolar substituent or is unsubstituted. Since the amphiphilic character of the polymer or oligomer is conferred by a periodic pattern of side chains rather than the precise spatial arrangement of side chains, other substitution patterns are also expected to produce facially amphiphilic polymers and oligomers and they are all encompassed by the present invention.

The polymers and oligomers of the present invention are designed using computer-aided computational techniques, such as de novo design techniques. The goal of the approach used to design the polymers and oligomers of the invention is to capture the structural and biological properties of antimicrobial peptides within the framework of traditional polymers that can be prepared by inexpensive condensation reactions. Thus, facial amphiphilicity is the key property to be introduced into the polymer or oligomer. Charge density, hydrophobicity, and degree of amphiphilicity, are also important parameters in maximizing lethal activity against microbes while minimizing activity against mammalian cells.

The general approach is as follows:

1) A polymer backbone that should fold into a given, well-defined three-dimensional structure is defined using molecular dynamics and quantum force field calculations. The polymer backbone is assembled from a repeating sequence of monomers. Extensive theoretical studies are then carried out to demonstrate that the polymers are able to adopt the desired secondary conformation.

2) Model compounds (short oligomers) are prepared for structural analysis of folding by X-ray crystallography.

3) Functional groups are then computationally grafted onto the backbone of the polymer as side groups to endow the oligomer or polymer with the desired facial amphiphilic character and to maximize diversity and maintain the drug-like properties of the polymer. The best combinations of functional groups are then computationally selected to produce cationic, amphiphilic structures.

4) Representative oligomers and polymers are synthesized to verify their structures, and their biological activities are measured.

5) Biophysical studies are carried out to confirm that the polymers are binding to membranes in the desired conformation, and that the mechanism of action is as expected from the design.

6) Based on the findings, structures are redesigned to optimize the potency and selectivity of the compounds and steps 2-4 are re-iterated.

The repeating sequence of monomers in the backbone must match the secondary structure adopted by the backbone. See, for example, Arnt, L., et al., *Polymer Reprints* 44:1266-1267 (2003). Also, monomer subunits in the backbone are not limited to monocyclic aryl compounds. They can be polycyclic aromatics that will modify the distances between groups and alter the periodicity of the subunits.

Molecular dynamic and coarse grain modeling programs can be used for the above design approach. See, for example, U.S. patent application Ser. No. 10/446,171, filed May 28, 2003, and published as Patent Application Publication No. US 2004/0107056 A1; and U.S. patent application Ser. No. 10/459,698, filed Jun. 12, 2003, and published as Patent Application Publication No. US 2004/0102941 A1. The contents of U.S. application Ser. No. 10/446,171 and U.S. application Ser. No. 10/459,698 are incorporated by reference herein in their entirety.

The computer-aided computational techniques used to design the polymers and oligomers identify potential low energy conformations that have a geometrical repeat that matches a convenient sequence repeat of less than 7 monomer units. Once these repeating scaffolds are identified and the frequency of the repeat is calculated, polar and nonpolar substituents can be incorporated into the monomers to confer amphiphilic properties into the molecule.

High level ab initio calculations are one technique which will identify accessible low energy conformations of various oligomers. Unfortunately, these techniques, while extremely powerful, have certain limitations known to those of skill in the art (MW limitations). Molecular Dynamics simulations provide an alternative that can be adapted efficiently to molecules envisioned in the present invention. Key elements in determining conformational energies are strong electrostatic interactions (i.e., intramolecular hydrogen bonding) between adjacent or more distant monomers and rigidification caused by the backbone torsions or by bulky functional groups. In order to simulate these interactions in molecular mechanics calculations the empirical parameters, i.e., a force field, must be determined for representative polymer backbones. Density functional theory (DFT) can be used to carry out ab initio calculations on small model compounds that share the basic structural connectivity of the polymer backbones and which will generate required torsional potentials. The procedure to carry out these computations is:

1. Select simple model compounds that share similar torsional patterns with the target polymer backbones.

2. For each compound, perform a full geometric optimization at the BLYP/6-3IG(d) level of theory (multiple initial configurations ensure the global minimum is obtained).

3. Calculate the single-point energy at the most stable geometry obtained in step 2 above, using B3LYP/6-311G++(dp) or plane wave CPMD.

4. Constrain a relevant torsion to a set angle and repeat steps 2 and 3.

5. Repeat step 4 for several angles; the torsional energy is obtained by subtracting the non-bonded interactions.

6. Fit energies versus torsion angle to a cosine series whose coefficients are the force field parameters.

After verifying the suitability of the force field by comparing computed predictions of the structure and thermodynamic properties to molecules that have similar torsional patterns and for which experimental data are available, the fitted torsions are then combined with bond stretching, bending, one-four, van der Waals, and electrostatic potentials borrowed from the CHARMM (Brooks, B. R., et al., *J. Comp. Chem.* 4:187-217 (1983) and TraPPE (Martin, M. G., and Siepmann, J. I., *J. Phys. Chem. B.* 103:4508-4517 (1999); Wick, C. D., et al., *J. Phys. Chem. B* 104:3093-3104 (1999)) molecular dynamics force fields. To identify conformations that can adopt periodic folding patterns with polar groups and apolar groups lined up on the opposite sides. Initial structures can be obtained with the Gaussian package (Frisch, M., et al., *Gaussian* 98 (revision A.7) Gaussian Inc., Pittsburgh, Pa. (1998)). Then, the parallelized plane-wave Car-Parrinello CP-MD (Car, R. and Parrinello, M., *Phys. Rev. Lett.* 55:2471-2474 (1985)) program, (cf. Röthlisberger, U., et al., *J. Chem. Phys.* 3692-3700 (1996)) is used to obtain energies at the minimum and constrained geometries. The conformations of the polymers without side-chains can be investigated in the gas phase. Both MD and MC methods will be used to sample the conformations. The former is useful for global motions of the polymer. With biasing techniques (Siepmann, J. I., and Frenkel, D., *Mol. Phys.* 75:59-70 (1992); Martin, M. G., and Siepmann, J. I., *J. Phys. Chem. B* 103:4508-4517 (1999); Vlugt, T. J. H., et al., *Mol. Phys.* 94:727-733 (1998)) the latter allows efficient sampling for polymers with multiple local minimum configurations that are separated by relatively large barriers.

The potential conformations are examined for positions to attach pendant groups that will impart amphiphilic character to the secondary structure. Polymers selected from the gas-phase studies with suitable backbone conformations and with side-chains at the optimal positions to introduce amphiphilicity will be further evaluated in a model interfacial system, n-hexane/water, chosen because it is simple and cheap for calculations while it mimics well the lipid/water bilayer environment. Polymer secondary structures that require inter-polymer interactions can be identified by repeating the above-mentioned calculations using a periodically repeated series of unit cells of various symmetries (so called variable cell molecular dynamics or Monte Carlo technique) with or without solvent. The results of these calculations will guide the selection of candidates for synthesis.

An embodiment of the present is a computation technique to identify polymer backbones which can produce facially amphiphilic polymers by:

(1) selecting a polymer backbones or scaffolds suitable for regiospecific introduction of polar (PL) and nonpolar (NPL) groups;

(2) determining parameters for a molecular mechanics force field utilizing ab initio quantum mechanical calculations;

(3) calculating energetically accessible conformations of said backbone using molecular dynamics or molecular mechanics calculations;

(4) identifying energetically accessible conformations of said backbone wherein the periodicity of a geometrical/conformational repeat matches a sequence repeat;

(5) synthesizing monomers with polar and nonpolar substituents; and (6) synthesizing an antimicrobial polymer or oligomer containing said monomers by solution or solid-phase synthesis.

The polyaryl and polyarylalkynyl polymers of the present invention are synthesized according to the procedures outlined in WIPO Publ. No. WO 02/072007, the entire contents of which are fully incorporated herein by reference.

Phenylalkynyl polymers can be synthesized by the general method outlined in Scheme 1. In this method, a dried flask is charged with equal ratios of diethynyl benzene and the appropriate diiodo monomer, 3 mol % Pd(PPh$_3$)$_4$, and 6 mole % CuI in toluene/diisopropylethylamine (4:1 ratio). The resulting solution is heated at about 70° C. for about 12 hours. The polymer product is precipitated using an appropriate solvent and dried under reduced pressure. Deprotection of the Boc group is accomplished with 4 M HCl/dioxane. See Arnt, L., and Tew, G. N., *J. Am. Chem. Soc.* 124:7664-7665 (2002), with supporting information (see pg. 7665) that includes experimental procedures and compound characterization (available over the interne at http://pubs.acs.org). The contents of this document are fully incorporated by reference herein. See also Breitenkamp, R. B., and Tew, G. N., *Polymer Reprints* 44:673-674 (2003) and Arnt, L., et al., *Polymer Reprints* 44:1266-1267 (2003). The contents of each of these documents are fully incorporated herein by reference.

Scheme 1

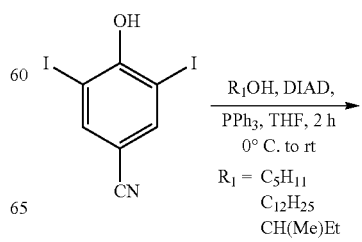

$R_1 = C_5H_{11}$
$C_{12}H_{25}$
$CH(Me)Et$

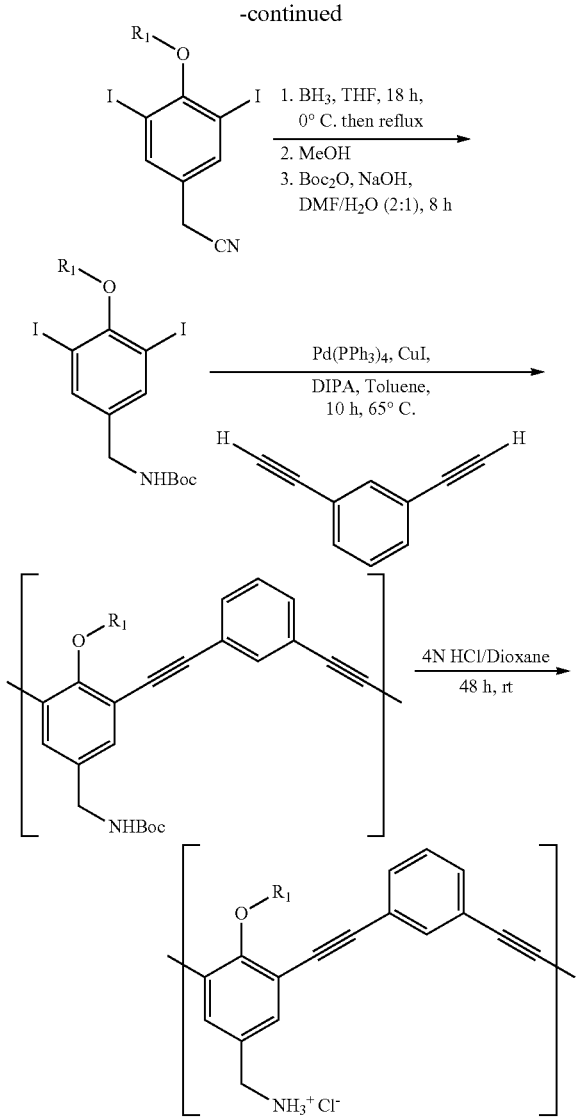

In some aspects of the invention, oligomers of the present invention are synthesized by solid-phase synthetic procedures well know to those of skill in the art. See, for example, Tew et al. (Tew, G. N., et al., *Proc. Natl. Acad. Sci.* (USA) 99:5110-5114 (2002)). For example, phenylalkynyl oligomers of Formula Ia can be synthesized by the method exemplified in Example 1 below using solid phase synthetic procedures. See, for example, Barany, G., et al., *Int. J. Pept. Prot. Res.* 30:705-739 (1987); *Solid-phase Synthesis: A Practical Guide*, Kates, S. A. and Albericio, F., eds., Marcel Dekker, New York (2000); and Dörwald, F. Z., *Organic Synthesis on Solid Phase: Supports, Linkers, Reactions*, 2$^{nd}$ ed., Wiley-VCH, Weinheim (2002).

One of skill in the art will recognize that the synthetic processes for producing polymers and oligomers of the invention can be modified to produce different ranges in molecular weight. The polymer chemist will readily appreciate that the chain length of polymers can be varied by techniques know in the polymer art. Advancements in solid-phase and solution phase synthesis of amino acid oligomers have made available techniques to prepare homogeneous oligomers with defined sequence and size and these techniques can be adapted to the present invention.

Thus, the polymers and oligomers of the invention can be synthesized in a range of molecular weights. Molecular weights for the polymers and oligomers range from about 300 Daltons to about 1,000,000 Daltons. Preferred polymers of the present invention have average molecular weights that range from about 400 Daltons to about 120,000 Daltons (about 2 to about 500 monomer units). Especially preferred polymers have average weights that range from about 1,000 Daltons to about 25,000 Daltons (about 5 to about 100 monomer units). Oligomers of the present invention have molecular weights that range from about 300 Daltons to about 6,000 Daltons (about 2 to about 25 monomer units), with preferred oligomers having molecular weights that range from about 300 Daltons to about 2,500 Daltons (about 2 to about 10 monomer units).

The syntheses of appropriately substituted monomers are straightforward. An example of the preparation of monomers for meta-phenylene derivatives is illustrated in Scheme 1 above. In addition, ortho- and para-dihalides or boronic acids are suitable precursors for a variety of coupling reactions and numerous pathways are available to incorporate polar and nonpolar side chains. Phenolic groups on the monomer can be alkylated to produce polar and nonpolar substituents. Alkylation of the commercially available phenol will be accomplished with standard Williamson ether synthesis for the nonpolar side chain with ethyl bromide as the alkylating agent. Polar sidechains can be introduced with bifunctional alkylating agents such as BOC—NH(CH$_2$)$_2$Br. Alternatively, the phenol group can be alkylated to introduce the desired polar side chain by employing the Mitsonobu reaction with BOC—NH(CH$_2$)$_2$—OH, triphenyl phosphine, and diethyl acetylenediacarboxylate. The processes required for the synthesis of appropriate monomers is well known in the art.

In some aspects of the invention, the facially amphiliphilic polymers and oligomers disclosed herein provide surface-mediated microbicides that kill microorganisms in contact with the surface. For these applications, the polymers and oligomers may be attached to, applied on or incorporated into almost any substrate including, but not limited to, woods, paper, synthetic polymers (plastics), natural and synthetic fibers, natural and synthetic rubbers, cloth, glasses and ceramics, by appropriate methods including, but not limited to, covalent bonding, ionic interaction, coulombic interaction, hydrogen bonding or cross-linking. Procedures for attaching, applying, and incorporating the polymers and oligomers of the invention into appropriate materials and substrates are disclosed in WIPO Publ. No. WO 02/072007. Appropriate substrates and materials are also disclosed in WO 02/072007.

The polymers and oligomers of the invention can be tested for antimicrobial activity by methods well known to those of skill in the art. See, for example, Tew, G. N., et al., *Proc. Natl. Acad*, Sci. (USA) 99:5110-5114 (2002).

Antimicrobial testing is performed according to procedures well known to those of skill in the art. For example, antibacterial assays are carried out using the micro-broth dilution technique with *E. coli*, or, if desired, another bacterial strain, such as, for example, *B. subtilis, P. aeruginosa, K. pneumoniae, S. typhimurium, N. gonorrhoeae, B. megaterium, S. aureus, E. feacalis, M. luteus*, or *S. pyogenes*. Other specific bacterial strains that can be screened include ampicillin and streptomycin-resistant *E. coli* D31, vancomycin-resistant *Enterococcus faecium* A436, and methicillin-resistant *S. aureus* 5332. Any polymer or oligomer found to be active can be purified to homogeneity and re-tested to obtain an accurate IC$_{50}$. Secondary screens include *Klebsiella pneumoniae* Kp1, and *Salmonella typhimurium* S5, and

*Pseudomonus aeruginosa* 10. Traditionally, the micro-broth dilution technique only evaluates a single data point between 18-24 hours; however, the measurements can be extended to 24 hr to monitor cell growth through the entire growth phase. These experiments are performed in LB medium (which is a rich medium typically used to grow cells for protein expression) and represent a critical initial screen for activity. Since salt concentration, proteins, and other solutes can affect the activities of antibiotics, materials that show no activity in rich medium can be re-tested in minimal medium (M9) to determine if rich medium is limiting activity. No relationship between the media and the activity has been observed which is consistent with the mode of action that is believed to be through general membrane disruption.

Standard assays can be performed to determine whether a polymer or oligomer of the present invention is bacteriostatic or bacteriocidal. Such assays are well known to those of skill in the art and are performed, for example, by incubating *E. coli* cells overnight with the polymer or oligomer being tested, and then plating the mixture on agar plates according to procedures well known to those of skill in the art. See, for example, Tew, G. N., et al., *Proc. Natl. Acad. Sci.* (USA) 99:5110-5114 (2002), and Liu, D., and DeGrado, W. F., *J. Amer. Chem. Soc.*, 123:7553-7559 (2001).

Assays for determining the antiviral and antifungal activity of polymers and oligomers of the invention are also well known to those of skill in the art. For examples of antiviral assays, see Belaid, A., et al., *J. Med. Virol.* 66:229-234 (2002); Egal, M., et al., *Int. J. Antimicrob. Agents* 13:57-60 (1999); Andersen, J. H., et al., *Antiviral Rs.* 51:141-149 (2001); and Bastian, A., and Schafer, H., *Regul. Pept.* 15:157-161 (2001). See also Cole, A. M., et al., *Proc. Natl. Acad. Sci* (USA) 99:1813-1818 (2002). For examples of antifungal assays, see Edwards, J. R. et al., *Antimicrobial Agents Chemotherapy* 33:215-222 (1989), and Broekaert, W. F., et al., *FEMS Microbiol. Lett.* 69:55-60 (1990). The entire contents of each of these documents are fully incorporated herein by reference.

Assays for measuring the cytotoxic selectivity for polymers and oligomers of the invention toward bacteria and eukaryotic cells are well known to those of skill in the art. For example, cytotoxic selectivity can be assessed by determining the hemolytic activity of the polymer or oligomer. Hemolytic activity assays are performed by measuring the degree of hemolysis of human erythrocytes following incubation in the presence of the polymer or oligomer and determining $HC_{50}$ values. $HC_{50}$ values represent the concentration of polymer or oligomer that results in 50% hemoglobin release. See, for example, Liu, D., and DeGrado, W. F., *J. Amer. Chem. Soc.*, 123:7553-7559 (2001), and references cited therein. See also Javadpour, M. M., et al., *J. Med. Chem.* 39:3107-3113 (1996).

Vesicle leakage assays can also be used to confirm that a polymer or oligomer of the invention interacts with and disrupt phospholipid bilayers, a model for cellular membranes. Vesicle leakage assays are well known to those of skill in the art. See, for example, Tew, G. N., et al., *Proc. Natl. Acad. Sci.* (USA) 99:5110-5114 (2002), and references cited therein.

Assays for determining the heparin-neutralizing activity of a polymer or oligomer of the invention are well known to those of skill in the art and are commonly performed using either an activated partial thromboplastin time assay (in which the delay in clotting time for activated plasma in the presence of a fixed concentration of heparin is measured in the absence and presence of a test compound) or a Factor X assay. See, for example, Kandrotas, R. J., *Clin. Pharmacokinet.* 22:359-374 (1992); Wakefield, T. W., et al., *J. Surg. Res.* 63:280-286 (1996); Diness, V. O. and Ostergaard, P. B., *Thromb. Haemost.* 56:318-322 (1986), and references cited therein. See also Wong, P. C. et al., *J. Pharm. Exp. Therap.* 292:351-357 (2000), and Ryn-McKenna, J. V., et al., *Thromb. Haemost.* 63:271-274 (1990).

For therapeutic applications, polymers or oligomers of the invention are provided by any number of routes of administration, including but not limited to peroral, buccal, ocular, aural, nasal, topical, parenteral (i.e., intramuscular, intraperitoneal, intra-abdominal, subcutaneous, intrathecal, intrapleural, intravenous and intraarterial) inhalation, transdermal, vaginal, transmucosal, transurethral, rectal, and pulmonary administration.

The polymers and oligomers of the present invention are administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the polymers and oligomers (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication (e.g., whether the polymer or oligomer is administered to treat a microbial infection, or to provide an antidote for hemorrhagic conditions associated with heparin therapy). The mode of administration can depend on the pathogen or microbe to be targeted. The selection of the specific route of administration and the dose regimen is to be adjusted or titrated by the clinician according to methods known to the clinician in order to obtain the optimal clinical response. The amount of polymer or oligomer to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical compositions comprising oligomers of Formula I and Formula Ia are provided in any number of forms, including but not limited to, capsules, tablets, lozenges, liquid solutions, liquid emulsions, liquid suspensions, liquid drops, liquid sprays, gels, creams, ointments, transdermal patches, powder formulations, and other formulations known in the art.

Thus, the pharmaceutical formulations containing the polymers and oligomers and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or oligomer as taught in this invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and Goodman & Gilman's *The Pharmaceutical Basis of Therapeutics*, 6th Edition, MacMillan Publishing Co., New York (1980) can be consulted.

The polymers and oligomers can be formulated for parenteral administration by injection, e.g., by bolus injection or continuous infusion. The polymers and oligomers can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the polymers and oligomers can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose (HPMC), sodium carboxymethylcellulose (NaCMC), and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the polymer and oligomer compositions can take the form of, e.g., tablets or lozenges formulated in a conventional manner.

For administration by inhalation, the polymers and oligomers for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The polymers and oligomers of the invention can also be formulated in rectal compositions such as suppositories or retention enemas, e.g., containing conventional suppository bases such as cocoa butter or other glycerides.

In addition to the formulations described previously, the polymers and oligomers can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the polymers and oligomers can be formulated with suitable polymeric or hydrophobic materials (for example as an emulsion in an acceptable oil) or ion exchange resins, or as sparingly soluble derivatives, for example, as a sparingly soluble salt.

In transdermal administration, the polymers and oligomers, for example, can be applied to a plaster, or can be applied by transdermal, therapeutic systems that are consequently supplied to the organism.

The pharmaceutical compositions of the polymers and oligomers of the invention can also comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The polymers and oligomers can also be administered in combination with other active ingredients, such as, for example, adjuvants, protease inhibitors, or other compatible drugs or compounds where such combination is seen to be desirable or advantageous in achieving the desired effects of the methods described herein (e.g., controlling infection caused by harmful microorganisms, or treating hemorrhagic complications associated with heparin therapy.). For example, the polymers and oligomers of the present invention can be administered with other antibiotics, including, but not limited to, vancomycin, ciprofloxacin, merapenem, oxicillin, and amikacin.

For those applications in which the polymers and oligomers of the present invention are used as disinfectants and/or preservatives, e.g., in cleansers, polishers, paints, sprays, soaps, hand lotions, or detergents, the polymers and oligomers are incorporated into the cleanser, polisher, paint, spray, soap, hand lotion, or detergent formulation, optionally in combination with suitable solvent(s), carrier(s), thickeners, pigments, fragrances, deodorizers, emulsifiers, surfactants, wetting agents, waxes, or oils. If the polymer or oligomer is to be used as a preservative in a foodstuff, the polymer or oligomer can be added to the foodstuff as part of any comestible formulation that can also include a suitable medium or carrier for convenient mixing or dissolving into the foodstuff. The amount of polymer or oligomer added to or incorporated into the cleanser, polisher, soap, etc. formulation or into the foodstuff will be an amount sufficient to kill or inhibit the growth of the desired microbial species and can easily be determined by one of skill in the art.

For those applications in which the polymers and oligomers of the invention are used as surface-mediated microbicides, e.g., in some applications as disinfectants and as preservatives (e.g., including, but not limited to, medical devices such as catheters, bandages, and implanted devices, or food containers and food handling implements), the polymers and oligomers may be attached to, applied on or incorporated into almost any substrate including, but not limited to, woods, paper, synthetic polymers (plastics), natural and synthetic fibers, natural and synthetic rubbers, cloth, glasses and ceramics by appropriate methods, including covalent bonding, ionic interaction, coulombic interaction, hydrogen bonding or cross-linking.

Procedures for attaching, applying, and incorporating the polymers and oligomers of the invention into appropriate materials and substrates are disclosed in WIPO Publ. No. WO 02/072007, the contents of which are fully incorporated herein by reference. Appropriate substrates and materials are also disclosed in WO 02/072007.

The following examples are illustrative, but not limiting, of the methods and compositions of the present invention. Other suitable modifications and adaptations of the variety of conditions and parameters normally encountered and obvious to those skilled in the art are within the spirit and scope of the invention.

EXAMPLE 1

Synthesis of Phenylalkynyl Oligomers

The following general method can be used to synthesize phenylalkynyl trimer oligomers.

Starting from dibromobenzoic acid, the appropriate dibromide carboxylate monomer is transformed to the corresponding cyanide and then reduced to amine. The dibromide reacts with diethynyl benzene via Sonogashira coupling to give the final trimer. The guanidinyl derivative is obtained by treating the amine with N,N'-bis(tert-butoxycarbonyl)-1H-pyrazole-1-carboxamidine followed by Boc deprotection. See, for example, Arnt, L, and Tew, G. N., J. Am. Chem. Soc. 124: 7664-7665 (2002), with supporting information (see pg. 7665) that includes experimental procedures and chompound characterization (available over the internet at http://pubs.acs.org).

Figure 2:
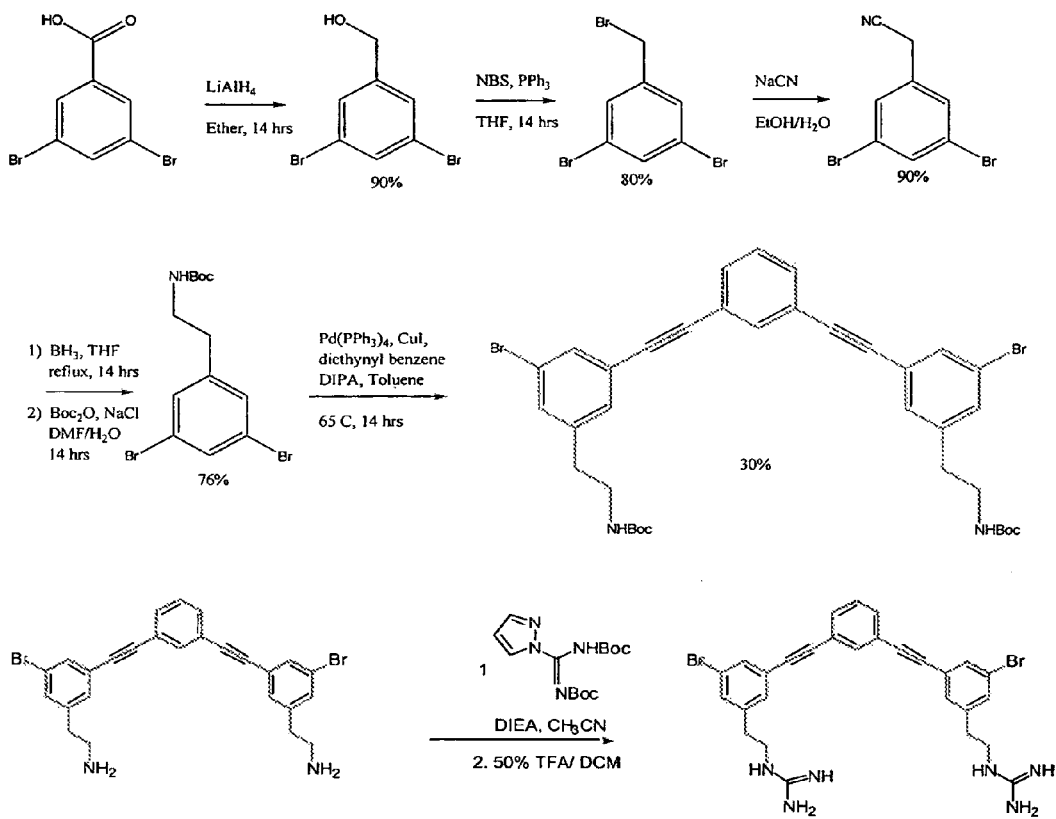
FIG. 2 illustrates a synthetic scheme for synthesis of the phenylalkynyl trimer Compound 3.

Phenylalkynyl trimer 3 was synthesized according to this procedure, as illustrated in FIG. 2. Starting from dibromobenzoic acid, dibromobenzoic acid monomer was transformed to the corresponding cyanide and then reduced to amine (total yield 50%). The dibromide was then reacted with diethynyl benzene via Sonogashira coupling to give the final trimer, with 30% yield. The guanidinyl derivative was obtained by treating the amine with N,N'-bis(tert-butoxycarbonyl)-1H-pyrazole-1-carboxamidine followed by Boc deprotection.

EXAMPLE 2

Antimicrobial Activities of Phenylalkynyl Oligomers

A series of phenylalkynyl trimer oligomers was tested for in vitro antibacterial activity and for selectivity for bacterial or mammalian cells.

Antibacterial assays were performed using a modification of the standard microbroth dilution assay recommended by the National Committee for Clinical Laboratory Standards (NCCLS) which has been developed for determining in vitro antimicrobial activities of cationic agents (Liu, D., and DeGrado, W. F., J. Amer. Chem. Soc., 123:7553-7559 (2001); Steinberg, D. A., et al., Antimicrob. Agents Chemother. 41:1738-1742 (1997); Yan, H., and Hancock, R. E. W., Antimicrob. Agents Chemother. 45:1558-1560 (2001); Amsterdam, D., "Susceptibility testing of antimicrobials in liquid media," in Antibiotics in Laboratory Medicine, 4$^{th}$ edition, Loman, V., ed., Williams and Wilkens, Baltimore, Md. (1996), pp. 52-111). Modifications were made to minimize loss of the antimicrobial agent due to adsorption onto glass or plastic surfaces and by precipitation at high concentrations. This procedure is a stringent test of antibacterial activity because of the high ionic strength of the growth medium which can inhibit the action of cationic agents but better reflects activity in the human host. Bacterial cell growth was assessed after 18 to 20 hours of incubation with each compound by measuring the optical density of the cultures at 600 nm on a microplate reader. MIC (minimum inhibitory concentration) values were determined for each compound.

Selectivity of cytotoxicity for bacteria versus mammalian cells was assayed by measuring hemolysis of human erythrocytes following one hour incubation in the presence of the oligomer being tested (Liu, D., and DeGrado, W. F., J. Amer. Chem. Soc., 123:7553-7559 (2001)) and determining an $HC_{50}$ value for the oligomer. $HC_{50}$ values represent the concentration of oligomer that results in 50% hemoglobin release.

The results are presented in Table 1 and Table 2.

TABLE 1

Antibacterial activity data for phenylalkynyl oligomers.

| Phenyl Alkynyl Trimer Compound No. | Structure | E. coli MIC (µg/ml) | B. subtilis MIC (µg/ml) | K. pneumonia MIC (µg/ml) | Hemolysis $HC_{50}$ (µg/ml) |
|---|---|---|---|---|---|
| 3 | 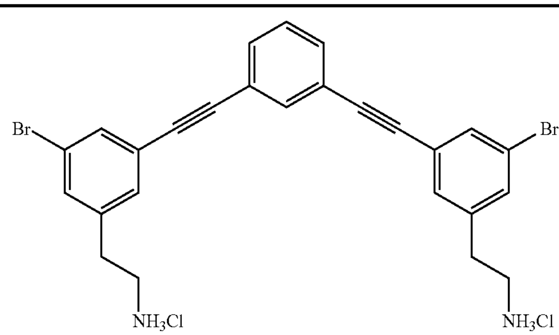 | 0.8 | 1.6 | 1.7 | 75 |

TABLE 1-continued
Antibacterial activity data for phenylalkynyl oligomers.
| Phenyl Alkynyl Trimer Compound No. | Structure | E. coli MIC (μg/ml) | B. subtilis MIC (μg/ml) | K. pneumonia MIC (μg/ml) | Hemolysis HC$_{50}$ (μg/ml) |
|---|---|---|---|---|---|
| 2 | 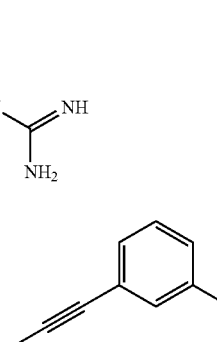 | 3.2 | 1.6 | | 8 |
| 4 | 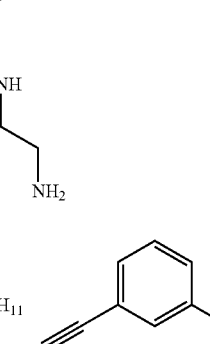 | 50 | 25 | | 12.5 |
| 5 | 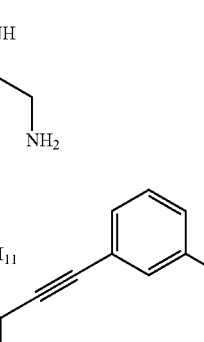 | 25 | 100 | | <12.5 |
| 6 | 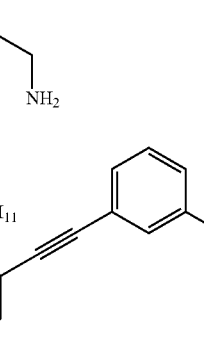 | 6.4 | 3.2 | | 5 |

TABLE 2

Phenylalkynyl structure-activity relationships

| Backbone | R1 | R2 | Compound | MIC$_{90}$ (µg/ml) E. Coli | MIC$_{90}$ (µg/ml) B. subtilis | HC$_{50}$ (µg/ml) | Selectivity HC$_{50}$/MIC$_{E.coli}$ |
|---|---|---|---|---|---|---|---|
| (Br-substituted bis-phenylalkynyl benzene with R1, R2 substituents) | OC$_5$H$_{11}$ | ethyl-guanidinium (NH, NH$_3$Cl) | 1 | 6.4 | 3.2 | 4.6 | 0.7 |
| | H | propyl-guanidinium (NH, NH$_3$Cl) | 2 | 1.6 | 1.6 | 8.5 | 5.3 |
| | H | propyl-NH$_3$Cl | 3 | 0.8 | 1.6 | 75 | 88.2 |

The data in Tables 1 and 2 indicate that Compound 1 inhibited the growth of gram negative *E. coli* and gram positive *B. subtilis* but was highly ytotoxic for human erythrocytes. A reduction in the hydrophobicity at R1 improved potency and, to a lesser extent, reduced erythrocyte cytotoxicity (Compound 2 and Compound 4). A further modification of the positive charge at R2 dramatically reduced erythrocyte toxicity while also improving potency, resulting in a highly potent and selective compound with a molecular weight of only 595 (Compound 3). The MBC for Compound 3 against *E. coli* D31 (defined as >3 log reduction in bacterial titre) and was found to be 0.8 ug/ml, confirming a bactericidal activity.

Compound 3 was next screened against a panel of gram positive and gram negative bacteria for growth inhibitory (MIC) activity. The gram positive organisms included in the screen were *Bacillus, Listeria* and *Staphylococcus* species. Tne results presented in Table 3 indicate that Compound 3 possesses a broad spectrum and potent activity against many, if not all, of the bacteria in the panel. Compound 3 potently inhibited the growth of several important human pathogens (including *Listeria monocytogenes, Pseudomonas aeruginosa* and *Staphylococcus aureus*) and also inhibited the growth of bacteria which are normally resistant to the action of the antimicrobial peptides (*Enterococcus faecalis* and *Salmonella typhymurium*). The potent activity against *B. subtilis* and *B. cereus* (ATCC 21929) suggests that Compound 3 may also inhibit the growth of *B. anthracis* based on the phylogenic relationships of these three bacterial strains.

TABLE 3

| Organism | MIC$_{100}$ | Organism | MIC$_{100}$ |
|---|---|---|---|
| Bacillus cereus | 1.7 | Neisseria sicca | 3.4 |
| Bacillus subtilis | 1.7 | Proteus mirabilis | >6.6 |
| Bacillus globigii | 3.4 | Pseudomonas stuarti | >6.6 |
| Escherichia coli 6C4468 | 1.7 | Proteus vulgaris | 3.4 |
| Escherichia coli CIS | 1.7 | Pseudomonas aeruginosa | 3.4 |
| Escherichia coli D31 | 0.84 | Salmonella typhimurium | 3.4 |
| Enterobacter cloacae | 1.7 | Serratia marcescens | 3.4 |
| Enterococcus faecalis | 0.84 | Staphylococcus aureus | 1.7 |
| Klebsiella aerogenes | 3.4 | Staphylococcus epidermidis | 0.8 |
| Klebsiella pneumoniae | 1.7 | Staphylococcus saprophyticus | 0.8 |
| Listeria monocytogenes | 1.7 | Streptococcus agalactiae | 0.4 |
| Moraxella catarrhalis | 0.84 | Streptococcus gordonii | 1.7 |

EXAMPLE 3

Antibacterial Activity of Phenylalkynyl Oligomers Against the Category A Biopathogens *Bacillus anthracis, Francisella tularensis*, and *Yersinia pestis*

To measure efficacy against potent biowarfare pathogens, MIC$_{100}$ values against *B. anthracis* and *Y. pestis* were determined for the phenyl alkynyl oligomer Compound 3 of Example 2 above.

The *B. anthracis* and *Y. pestis* cultures were established as follows: For *Y. pestis* cultures, a blood agar plate was streaked from a tube of frozen *Y. pestis* (YP.NM 4 stock) and incubated 48 hr at 37° C., 5% CO$_2$. At the end of the second day, a miniculture was set up by adding a colony from the previously prepared blood agar plate into 10 ml of Mueller Hinton II Broth (BBL, Becton Dickinson, Lot #3338743) and incubated overnight at 37° C., 5% CO$_2$. A maxiculture was set up by diluting the mini-culture at a 1:10 dilution and incubated for 3 hrs at 37° C., 5% CO$_2$ until the OD$_{600}$ reached 0.115 (approx. 4×10$^7$ cfu/ml). An aliquot of the culture was then diluted to approximately 5×10$^5$ cfu/ml for use in assay. For *B. anthracis* cultures, a blood agar plate was streaked from a tube of frozen *Bacillus anthracis* (BA-NS-2 spore stock), and incubated overnight at 37° C., 5% CO$_2$. On the morning of the following day, a miniculture was set up with an isolated colony from the previously prepared blood agar plate in 5 ml of Mueller Hinton II Broth (BBL, Becton Dickinson, Lot #0327000) and incubated at 37° C., 5% CO$_2$. At the end of the day, a new mini-culture was set up by diluting the previous culture 1:1000 in broth, and incubated overnight at 37° C., 5% CO$_2$. A maxiculture was set up a by diluting the mini-culture at a 1:1000 dilution, and incubated for 6 hrs at 37° C., 5% CO$_2$, until the OD$_{600}$ reached 0.3 (approx. 2×10$^6$ cfu/ml).

MIC (minimum inhibitory concentration) determinations were performed in 96-well plates using serial two-fold dilutions (performed in duplicate) of Compound 3 and the positive control agent (ciprofloxacin). The inoculum in the assay wells was 4.1×10$^5$ cfu/ml for *Y. pestis* and 8×10$^4$ cfu/ml for *B. anthracis* (200 ul total volume). The assay plates were inserted in the Bioscreen Reader (Thermo Labsystems, Franklin, Mass., USA), and incubated at 37° C., 5% CO$_2$. The final MIC values were recorded at 30 hrs and 24 hrs for *Y. pestis* and *B. anthracis*, respectively (Table 4). The MIC values represent the lowest concentration for each compound which showed ≤10% of the $OD_{600}$ observed in control wells containing organism alone.

TABLE 4

24 Hour and 30 Hour $MIC_{100}$ Values for *Y. pestis* and *B. anthracis*

| | $MIC_{100}$ (µg/ml) | |
|---|---|---|
| Compound | *B. anthracis* (24 hr) | *Y. pestis* (30 hr) |
| Ciprofloxacin | 0.125-0.25 | 0.0312 |
| Compound 3 | 1 | 4 |

In a second screen, Compound 3 was screened against multiple clinical/field isolates of *B. anthracis* and *Y. pestis*. MIC determinations were performed according to NCCLS guidelines under similar conditions to those described above. *F. tularensis* was tested in $Ca^{2+}$-adjusted Mueller Hinton broth supplemented with 2% IsoVitalex and absorbance values were read at 24 and 48 hours. Ciprofloxacin was used as the positive control antibiotic agent and *Staphylococcus aureus* was used as the control microbial agent. $MIC_{100}$ values represent the lowest concentration of compound which resulted in no visible growth judged by turbidity.

TABLE 5

$MIC_{100}$ Values for Clinical/Field Isolates of *B. anthracis* and *F. tularenesis*

| | $MIC_{100}$ (µg/ml) | |
|---|---|---|
| Strain | Ciprofloxacin | Compound 3 |
| *B. anthracis* 1099 | 0.03 | 1 |
| *B. anthracis* A3 | 0.06 | 1 |
| *B. anthracis* A58 | 0.03 | 1 |
| *B. anthracis* A74 | 0.06 | 2 |
| *B. anthracis* A60 | 0.015 | 1 |
| *B. anthracis* A19 | 0.06 | 1 |
| *B. anthracis* A73 | 0.03 | 1 |
| *B. anthracis* AC1 | 0.03 | 1 |
| *B. anthracis* RA3R | 0.03 | 1 |
| *B. anthracis* 7611R | 0.03 | 2 |
| *B. anthracis* Vollum | 0.06 | 2 |
| *B. anthracis* 127 | 0.03 | 1 |
| *F. tularensis* 17137 | 0.03 | 1 |
| *F. tularensis* 17135 | 0.03 | 1 |
| *S. aureus* ATCC29213 | 0.25 | 2 |

In both sets of screens (Tables 4 and 5), potent and comparable growth inhibitory activity by Compound 3 was found for all tested strains of the biowarfare pathogens. The integrity of the assays is supported by the expected $MIC_{100}$ values for Compound 3 versus *S. aureus* and Ciprofloxacin (Cipro) versus the biopathogens strains which were measured in parallel assays.

The MIC studies for *Bacillus anthracis* summarized in Table 4 were performed by robotic screening, with growth of the organism recorded at 2 hour intervals over a total of 24 hours. Compound 3 showed complete inhibition of growth at early and late time points, consistent with a rapid bactericidal activity (FIG. 3A). A very different time-course of growth inhibition was observed for the positive control antibiotic, Cipro, where transient cell growth was observed at early time points at MIC and 2×MIC concentrations (FIG. 3B). Cipro is a bactericidal antibiotic that targets intracellular enzymes involved in DNA synthesis, and is the standard of care for anthrax infections. These results indicate that Compound 3 shows a very significant advantage over Cipro. For *B. anthracis* and other biopathogen infections, one critical requirement for effective therapy is treatment soon after exposure before the infection reaches a stage (often presymptomatic) when antibiotic therapy becomes ineffective. Therefore, rapidly bactericidal compounds are highly preferred.

EXAMPLE 4

Antibacterial Activity of Phenyl Alkynyl Oligomers Against Human Pathogens Associated with Hospital-Acquired Infections Compound 3 was screened for antibacterial activity against *E. coli*, *S. aureus* and methicillin-resistant *S. aureus* (MRSA). The results are presented in Table 6.

TABLE 6

MIC studies with gram-negative and gram-positive bacteria including MRSA

| | $MIC_{100}$ (µg/ml) | | | |
|---|---|---|---|---|
| Compound | *E. coli* OC2530 | *E. coli* ATCC25922 | *S. aureus* ATCC29213 | MRSA OC2878 |
| Compound 3 | 0.5 | 2 | 0.5 | 0.5 |
| Amikacin | 2 | 1 | 2 | 64 |

Growth inhibition assays were performed according to a modification of the standard microbroth dilution assay recommended by the National Committee for Clinical Laboratory Standards (NCCLS), which has been developed for determining in vitro antimicrobial activities of cationic agents (Steinberg et al., *Antimicrob. Agents Chemother.* 41:1738 (1997); Yan and Hancock, *Antimicrob. Agents Chemother.* 45:1558 (2001)). The modifications were made to minimize loss of the antimicrobial agent due to adsorption onto glass or plastic surfaces and by precipitation at high concentrations. Bacterial colonies from an agar plate were inoculated into 5 ml DIFCO Mueller-Hinton medium and incubated at 37° C. on a shaker platform (180 rpm) for 2 to 3 hours. The suspension was diluted to app. $4 \times 10^5$ cfu/ml and inoculated into a flat-bottom polypropylene (Costar) 96 well plate (90 µl volumes). Compound stock solutions were prepared in DMSO and serial two-fold dilutions of compound were made in 0.01% acetic acid, 0.2% bovine serum albumin in polypropylene eppendorf tubes and added to the plates (10 µl volumes) resulting in final concentrations ranging from 200 to 3.125 µg/ml. DMSO concentrations did not exceed 1% in the assay. All samples were done in triplicate. One set of control wells included broth-only samples with dilution buffer for testing sterility and providing blank values for the absorbance readings. Vehicle-control wells containing the bacterial suspension with DMSO (no compound) were also included. Following the overnight incubation (20 hours), the cell growth was assessed by measuring the optical density of the cultures at 600 nm ($OD_{600}$) on a microplate reader. $MIC_{100}$ values represent the lowest concentration of compound which resulted in no visible growth.

The results presented in Table 6 indicate that potent activity comparable to amikacin, a broad-spectrum aminoglycoside, was observed for Compound 3 against the drug-sensitive *E. coli* and *S. aureus* strains while superior activity to amikacin was observed against drug-resistant *S. aureus*. MRSA is currently the primary human pathogen responsible for a major portion of hospital-acquired infections.

In a second screen (Table 7), the growth inhibitory activity of Compound 3 was tested against a clinical isolates of gram-positive and gram-negative pathogens, including drug-resistant bacterial strains, which are commonly associated with hospital-acquired infections. In addition, clinical isolates of the nonfilamentous fungus (yeast), *C. albicans*, were also tested. Three positive control antibiotics, levofloxacin, linezolid and vancomycin, and one anti-fungal agent, amphotericin B, were included in the screen to verify the integrity of the assay. Growth conditions were done under modified NCCLS conditions as described above with the following changes in growth media: 1) *S. pneumonaie* and *S. pyogenes*: Mueller Hinton+2-5% lysed horse blood; 2) *Haemophilus*: Mueller Hinton+NAD+yeast extract+hematin; and 3) *C. albicans*: RPMI synthetic medium (GIBCO).

TABLE 7

Activity of Compound 3 against pathogens associated with hospital-acquired infections

| Organism | Phenotype | LEVOFLOX mic | LINEZOLID mic | VANCO mic | Compound 3 mic | AMP B mic |
|---|---|---|---|---|---|---|
| *Candida albicans* | | >8 | >8 | >32 | 1 | 2 |
| *Candida albicans* | | >8 | >8 | >32 | 0.5 | 2 |
| *Candida albicans* | | >8 | >8 | >32 | 1 | 2 |
| *Candida albicans* | | >8 | >8 | >32 | 0.5 | 2 |
| *Candida albicans* | | >8 | >8 | >32 | 0.5 | 2 |
| *Staphylococcus aureus* | OX-R | >8 | 2 | 1 | 0.5 | |
| *Staphylococcus aureus* | OX-R | 4 | 2 | 1 | 0.5 | |
| *Staphylococcus aureus* | OX-R | 0.25 | 2 | 1 | 0.5 | |
| *Enterococcus faecium* | | 2 | 2 | 0.5 | 8 | |
| *Enterococcus faecium* | | 4 | 2 | 1 | 8 | |
| *Enterococcus faecium* | | 0.5 | 2 | 1 | 0.5 | |
| *Enterococcus faecium* | VAN-R | >8 | 4 | 32 | 0.5 | |
| *Enterococcus faecium* | VAN-R | >8 | 8 | >32 | 0.5 | |
| *Enterococcus faecium* | VAN-R | >8 | 2 | >32 | 0.5 | |
| *Enterococcus faecalis* | | 1 | 2 | 1 | 1 | |
| *Enterococcus faecalis* | | 1 | 2 | 1 | 1 | |
| *Enterococcus faecalis* | VAN-R | >8 | 1 | >32 | 1 | |
| *Enterococcus faecalis* | VAN-R | >8 | 2 | >32 | 1 | |
| *Enterococcus faecalis* | VAN-R | >8 | 1 | >32 | 1 | |
| *Pseudomonas aeruginosa* | MDR | 8 | >8 | >32 | 32 | |
| *Pseudomonas aeruginosa* | MDR | 8 | >8 | >32 | 4 | |
| *Pseudomonas aeruginosa* | MDR | >8 | >8 | >32 | 16 | |
| *Stenotrophomonas (Xanthomonas) maltophilia* | | 0.12 | >8 | >32 | 1 | |
| *Stenotrophomonas (Xanthomonas) maltophilia* | | 0.25 | >8 | >32 | 1 | |
| *Stenotrophomonas (Xanthomonas) maltophilia* | | 0.12 | >8 | >32 | 1 | |
| *Staphylococcus epidermidis* | | 0.12 | 1 | 2 | 0.5 | |
| *Staphylococcus epidermidis* | | >8 | 1 | 2 | 0.5 | |
| *Staphylococcus epidermidis* | | 8 | 1 | 2 | 0.5 | |
| *Staphylococcus haemolyticus* | | 2 | 1 | 1 | 0.5 | |
| *Staphylococcus haemolyticus* | | >8 | 0.5 | 4 | 1 | |
| *Staphylococcus haemolyticus* | | 0.12 | 1 | 2 | 0.5 | |
| *Staphylococcus hominis* | | 0.12 | 1 | 1 | 0.5 | |
| *Staphylococcus hominis* | | >8 | 1 | 2 | 1 | |
| *Staphylococcus hominis* | | 0.12 | 1 | 1 | 0.5 | |
| *Staphylococcus saprophyticus* | | 0.5 | 2 | 1 | 0.5 | |
| *Staphylococcus saprophyticus* | | 0.12 | 1 | 2 | 0.5 | |
| *Staphylococcus saprophyticus* | | 0.12 | 1 | 1 | 0.25 | |
| *Haemophilus influenzae* | | ≤0.03 | >8 | >32 | 4 | |
| *Haemophilus influenzae* | | ≤0.03 | >8 | >32 | 4 | |
| *Haemophilus influenzae* | | ≤0.03 | 8 | >32 | 4 | |
| *Streptococcus pyogenes* | | 0.25 | 1 | 0.5 | 2 | |
| *Streptococcus pyogenes* | | 0.5 | 1 | 0.5 | 4 | |
| *Streptococcus pyogenes* | | 0.5 | 1 | 0.5 | 4 | |
| *Streptococcus pneumoniae* | | 1 | 1 | 0.5 | 2 | |
| *Streptococcus pneumoniae* | | 0.5 | 1 | 0.5 | 2 | |
| *Streptococcus pneumoniae* | PEN-R | 0.5 | 0.5 | 0.5 | 2 | |
| *Streptococcus pneumoniae* | PEN-R | 0.5 | 0.5 | 1 | 2 | |
| *Streptococcus pneumoniae* | PEN-R | 0.5 | 1 | 1 | 1 | |
| *Enterococcus faecalis* ATCC 29212 | | 0.5 | 2 | 4 | 1 | |
| *Streptococcus pneumoniae* ATCC 49619 | | 0.5 | 1 | 0.5 | 2 | |

(mic = $MIC_{100}$)

The results presented in Table 7 indicate that Compound 3 demonstrated potent and broad spectrum antimicrobial activity against nearly all strains tested including all strains of the Coagulase-negative Staphylococci, oxicillin-resistant (OX-R)*S. aureus*, vancomycin-resistant (VAN-R) *E. faecalis*, penicillin-resistant (PEN-R)*S. pneumoniae*, and the nonfilamentous yeast *C. albicans*. Potent and intermediate antimicrobial activities were observed against various isolates of multi-drug resistant (MDR) *P. aeruginosa*. The integrity of the assay was supported by the findings that all control antibiotics gave the expected susceptibility results according to NCCLS guidelines. Furthermore, compound 3 gave the expected $MIC_{100}$ values for two control ATCC strains of bacteria, *Enterococcus faecalis* ATCC 29212 and *Streptococcus pneumoniae* ATCC 49619, which have been tested frequently in previous assays. The broad spectrum activities of Compound 3 against gram-positive and gram-negative bacteria, drug-resistant strains and yeast indicate that phenyl alkynyl compounds of the invention can be preferred antimicrobial agents for therapeutic use, both for systemic and topical applications.

Bacterial Resistance. To measure experimentally the development of resistance (or the lack thereof) by bacteria to the antimicrobial activity of phenyl alkynyl oligomers, *S. aureus* was passaged serially in the presence of sub-MIC (0.5×) concentrations of Compound 3. The $MIC_{100}$ was measured at every 24 hour time point for 17 consecutive passages and, at each passage, the concentration of compound was set at 0.5× of the $MIC_{100}$ measured for the previous passage. As positive controls, two fluoroquinolones (ciprofloxacin and norfloxacin) were included in the assay, also at 0.5× concentrations. Bacteria, including *S. aureus*, readily develop resistance to both these antibiotics in this experimental paradigm.

Resistance was readily observed for both ciprofloxacin and norfloxacin, as early as passage 3 or 4, and the increases in MIC reached 125 fold and 160 fold, respectively, by passage 16. No consistent increase in the MIC was found with Compound 3 during the entire time course of the experiment, indicating that bacteria cannot effectively evade the antimicrobial action of the phenylalkynes.

EXAMPLE 5

Antibacterial Activity of Phenyl Alkynyl Oligomers Embedded in Polyurethane Films The retention of antimicrobial activity of phenyl alkynyl oligomers following incorporation into a polyurethane film was investigated. To control manufacturing costs, the preferred form of the antibacterial polymers and oligomers for material applications is a polymer. However, oligomers were used in this initial study to generate the most reliable data for determining structure/activity relationships for phenyl alkynyl polymers.

Figure 4:
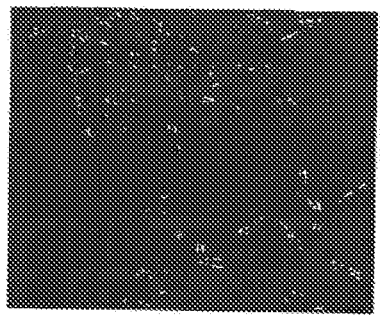
Figure 4:
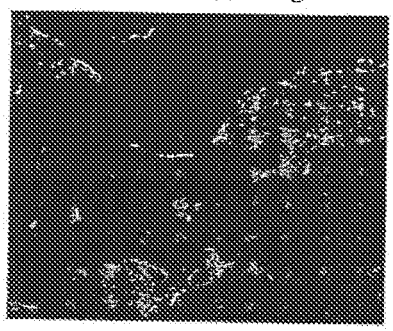
Figure 4:
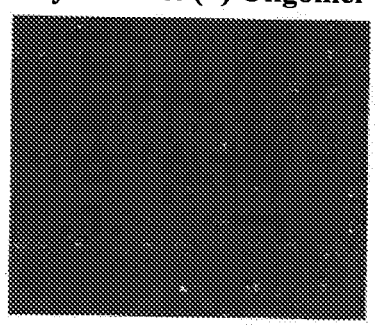

The retention of antimicrobial activity for the phenyl alkynyl trimer Compound 3 was tested after the oligomer was incorporated into a sheet of polyurethane film. The results are illustrated in FIG. 4.

An untreated glass slide, untreated polyurethane film, and polyurethane film containing an antimicrobial oligomer were immersed in a culture of bacteria (*E. coli* D31) growing at 37° C. for 72 hours. The Compound 3-derivatized polyurethane was produced by swelling the film with solvent containing the antimicrobial compound and allowing it to dry. During this process the film was infiltrated with Compound 3. At the conclusion of the 62 hour incubation period, significant bacterial growth was readily observed on the untreated glass and polyurethane surfaces. However, little apparent growth was observed on the Compound 3-polyurethane film, indicating that the oligomer had retained its antibacterial activity when incorporated into the surface of the plastic film.

The experiment was performed using *L. monocytogenes* in place of *E. coli* and identical results were observed.

EXAMPLE 6

Antiviral Activity of Oligomers

One or more oligomers of the invention (e.g., the phenyl alkynyl oligomer Compound 3) are synthesized as described above and tested for their ability to inhibit HIV replication in cell culture. Two viruses are used in the infection assays: NLHX or YU2 that use CXCR4 or CCR5 as co-receptors, respectively. U87/CD4/CCR5 or U87/CD4/CXCR4 cells are seeded in 48-well plates at $3 \times 10^4$ cells/well on the day prior to infection. Culture supernatants are removed from cells and replaced with pseudotyped luciferase reporter virus alone or pseudotyped luciferase reporter virus and oligomer at indicated final concentrations. Virus and compound are removed from cells approximately 16 hours post-infection, the cells are washed and then culture media was replenished. Cells are lysed and assayed for luciferase activity 3 days post infection. Results are presented as a percent of luciferase activity observed in the absence of compound.

EXAMPLE 7

Antifungal Activity of Oligomers

Several different genera of fungi are tested for their sensitivity to a set of oligomers of the present invention (e.g., one or more oligomers of the invention, such as the phenyl alkynyl trimer Compound 3). Both non-filamentous (yeast) and filamentous fungi are tested and specific fungi that are associated with various types of human infections are chosen for the screen (Table 8). One or more oligomers are tested for their antifungal activities. The antifungal assays are performed to determine the minimal inhibitory concentrations that result in complete inhibition of growth ($MIC_{100}$). All growth assays are done in a total of 1 ml volumes and growth is assessed by turbidity measurements. Additional antifungal assay conditions are described in Table 9.

TABLE 8

Clinical features of specific fungi.

| Organism | Clinical Features |
| --- | --- |
| Yeast | |
| *Candida albicans* ATCC 10231 | Mucosal infections (skin, GI, urinary tract, reproductive organs) |
| Filamentous fungi | |
| *Aspergillus fumigatus* ATCC 1028 | Allergic disease, sinusitis bronchopulmonary infections and systemic infections in immune-compromised individuals |
| *Cryptococcus neoformans* ATCC 24067 | Opportunistic pathogen causing systemic infections in immune-compromised individuals |
| *Trichophyton mentagrophytes* ATCC 9533 | Skin infections (dermatophytosis) |
| *Trichophyton rubrum* ATCC 10218 | Chronic infections of the skin and nails, most widely distributed dermatophyte |

TABLE 8-continued

Clinical features of specific fungi.

| Organism | Clinical Features |
|---|---|
| Control | |
| E. coli ATCC 25922 | Verify compound integrity and activity, verify assay conditions |

TABLE 9

Additional anti-fungal assay conditions

| | Method Conditions | | | | | |
|---|---|---|---|---|---|---|
| | Candida albicans | Aspergillus fumigatus | Cryptococcus neoformans | Trichophyton mentagrophytes | Trichophyton rubrum | E. coli (ATCC2 5922) |
| Culture Medium | Fluid Sabouraud Medium | Potatoe Dextrose Broth | Fluid Sabouraud Medium | Potatoe Dextrose Broth | Fluid Sabouraud Medium | Nutrient Broth |
| Incubation Time | 20 hours | 2 days | 2 days | 3 days | 3 days | 20 hours |
| Incubation Temp. | 37° C. | 28° C. | 37° C. | 28° C. | 28° C. | 37° C. |

EXAMPLE 8

Antifungal Activity of Phenylalkynyl Oligomers

MIC (minimum inhibitory concentration) and MFC (minimal fungicidal concentration) values were determined for Compound 3 in Example 2 above for each of the four fungi *A. fumigatus, P. funiculosum, C. globosum* and *T. virens*. MIC values for Compound 3 were also determined for the yeast *C. albicans*. The results are presented in Tables 10 and 11 below.

MIC endpoints were determined for *A. fumigatus, P. funiculosum, C. globosum* and *T. virens* according to current NCCLS guidelines defined for testing *A. fumigatus* (NCCLS M38-A, 2002). For yeast species (*C. albicans*), MIC endpoints were determined according to current NCCLS guidelines defined for testing *C. albicans* (NCCLS M27-A2, 2002). Amphotericin B was included in the screen with *C. albicans* as a positive control.

All MIC testing was done in 96 well microtiter panels using RPMI 1640 (with glutamine and without bicarbonate) broth as a growth media. Incubation was at 35° C., and growth was read at 48, 72, (and for some slow growing fungal species, 96 hours). Each investigational compound was tested over a range of 11 (eleven) doubling dilutions (e.g. 128-0.12 µg/ml).

MFC (minimal fungicidal concentrations) endpoints were calculated using a modified methodology based on the NCCLS defined methodology for measuring minimal bactericidal concentrations (MBC). Experimentation to calculate MFCs was undertaken only for those organisms for which an MIC endpoint was satisfactorily calculated. MFCs are defined as the concentration required to reduce the number of viable organisms by at least 90%.

TABLE 10

| | MIC/MFC | | | |
|---|---|---|---|---|
| Drug | Aspergillus fumigatus | Chaetomium globosum | Trichoderma virens | Penicillium funiculosum |
| Compound 3 | 32/32 | 0.5/8 | 32/32 | 1/2 |
| Fluconazole | >32/>32 | 0.25/0.25 | >128/>128 | 4/>32 |

TABLE 11

| Organism | Compound 3 mic | AMP B mic |
|---|---|---|
| Candida albicans | 1 | 2 |
| Candida albicans | 0.5 | 2 |
| Candida albicans | 1 | 2 |
| Candida albicans | 0.5 | 2 |
| Candida albicans | 0.5 | 2 |

EXAMPLE 9

Ability of Polymers and Oligomers to Inhibit the Anticoagulation Effects of Low Molecular Weight Heparin Several of the amphiphilic polymers and oligomers of the invention are synthesized and tested for their ability to inhibit the anticoagulation effects of heparin. It is assumed that heparin-neutralizing activity is largely dependent on the charge and charge distribution characteristics of the polymers and oligomers rather than on their hydrophobic qualities.

The delay in clotting times of activated plasma caused by a fixed concentration of heparin is tested in the presence of increasing concentrations of each polymer or oligomer. The clotting time of activated plasma in the presence of 1 unit (0.2 µg/ml) heparin is measured in the presence and absence of four concentrations of polymer or oligomer (44.4 µg/ml, 4.4 µg/ml, 1.5 µg/ml, and 0.4 µg/ml). The assay is performed four times for each concentration of polymer or oligomer and the average clotting time determined. Dose response data are collected.

An activated partial thromboplastin time assay (clotting assay) is used to determine clotting time. The assay is performed as follows: A plasma sample (0.1 mL) containing heparin or heparin and the polymer or oligomer to be tested is pipetted into a test cuvette and incubated at 37° C. for about 2 minutes. Reconstituted Cephalinex (a phospholipids platelet substitute which can be obtained from Bio/Data Corporation) (0.1 mL) is added to the plasma sample. The mixture is incubated at 37° C. for about 5 minutes. A 25 mM calcium chloride solution, prewarmed to 37° C., is added (0.1 mL) to the mixture, and clotting time is recorded using a fibrometer.

Antagonism of the delay in clotting time caused by low molecular weight heparin (LMWH) is also investigated. The clotting time of activated plasma in the presence of 4.6 µg/ml LMWH is measured in the absence and presence of three concentrations of polymer or oligomer (14.8 µg/ml, 1.5 µg/ml, and 0.4 µg/ml). Dose response data are collected.

The LMWH-antagonizing activity of the polymers and oligomers are also investigated by measuring the delay in clotting time in whole blood induced by three different concentrations of LMWH (LeoPharm, 1 μg/ml) in the presence or absence of one or more concentrations of polymer or oligomer. The performance of assays in whole blood are carried out in consideration of pharmaceutical applications, because such assays indicate whether potential serum protein binding by the polymer or oligomer that could impact biological activity in vivo is an issue. The assays are performed similarly to assays employing activated plasma and dose response data are collected.

EXAMPLE 10

Ability of Phenylalkynyl Oligomers to Inhibit the Anticoagulation Effects of Low Molecular Weight Heparin To assess the potential of the phenylalkynyl oligomers to act as antagonists of the low molecular weight heparins (LMWH), Compound 3 was assayed for its ability to antagonize the inhibition of Factor Xa (FXa) activity by the LMWH Lovenox was determined for Compound 3. Briefly, FXa activity in the presence of Lovenox and inhibitor was measured in a chromogenic assay using reagents purchased from DiaPharma. The reagents were reconstituted in a 0.02M Tris buffer at pH=8.4, and the final assay conditions were: 0.004 IU/mL AT, 0.14 nkat/well FXa, 0.01M Tris, 0.15M NaCl with a final volume of 112 μL. In the assay setup for Schild-plot analysis ($K_B$ determination), varying concentrations of Lovenox were incubated with AT for 5 minutes. Different concentrations of inhibitor were added to each row of wells, to construct curves of fixed inhibitor concentration, and lightly shaken and incubated for 20 minutes. FXa was then added and reaction was shaken and incubated for 10 minutes. The substrate (S-2765) was then added to initiate the clotting cascade and the 96-well plate was then shaken and read every 30 seconds for 7 minutes at 405 nm on a ThermoLabsystems Multiskan Spectrum. The single curve Lovenox titration experiments ($IC_{50}$ determination) consisted of the same procedure, but with a fixed concentration of Lovenox (determined by a titration curve in the absence of inhibitor). The analysis of each curve was performed using GraphPad Prism version 4.00 for Windows.

Potent antagonism by Compound 3 ($IC_{50}$=5.07 μM) on Lovenox inhibition of Factor Xa activity supports the therapeutic use of the phenylalkynes of the invention as LMWH antagonists.

Having now fully described this invention, it will be understood to those of ordinary skill in the art that the same can be performed within a wide and equivalent range of conditions, formulations, and other parameters without affecting the scope of the invention or any embodiment thereof.

All documents, e.g., scientific publications, patents, patent applications and patent publications, recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

We claim:
1. A method of treating a microbial infection in an animal in need thereof, said method comprising administering to the animal an effective amount of a pharmaceutical composition comprising an oligomer of Formula I:

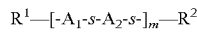

or an acceptable salt or solvate thereof, wherein:
(i) $A_1$ and $A_2$ are independently optionally substituted m-arylene or optionally substituted m-heteroarylene, wherein one of $A_1$ or $A_2$ is substituted with one or more polar (PL) group(s), one or more non-polar (NPL) group(s), or a combination of one or more polar (PL) group(s) and one or more non-polar (NPL) group(s), and the other of $A_1$ or $A_2$ is unsubstituted; or
(ii) one of $A_1$ or $A_2$ is as defined above and is optionally substituted with one or more polar (PL) group(s), one or more non-polar (NPL) group(s), or a combination of one or more polar (PL) group(s) and one or more non-polar (NPL) group(s); and the other of $A_1$ or $A_2$ is the group —C≡C(CH$_2$)$_p$C≡C—, wherein p is 0 to 8, and the —(CH$_2$)$_p$— alkylene chain is optionally substituted with one or more amino or hydroxyl groups;
s is —C≡C—;
$R^1$ is
(i) hydrogen, a polar group (PL), or a non-polar group (NPL), and $R^2$ is -$A_1$-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or
(ii) hydrogen, a polar group (PL), or a non-polar group (NPL), and $R^2$ is -$A_1$-s-$A_2$-$R^1$, wherein each of $A_1$ and $A_2$ is as defined above and is optionally substituted with one or more polar (PL) group(s), one or more non-polar (NPL) group(s), or a combination of one or more polar (PL) group(s) and one or more non-polar (NPL) group(s); or
(iii) A'-s- and $R^2$ is -$A_1$-s-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s); or
(iv) A'-s- and $R^2$ is -A', wherein A' is aryl or heteroaryl, either of which is optionally substituted with one or more polar (PL) group(s), one or more non-polar (NPL) groups(s), or a combination of one or more polar (PL) group(s) and one or more non-polar (NPL) group(s); or
(v) $R^1$ and $R^2$ together form a single bond;
NPL is a non-polar group independently selected from —B(OR$^4$)$_2$ or —(NR$^{3'}$)$_{q1NPL}$—U$^{NPL}$—(CH$_2$)$_{pNPL}$—(NR$^{3''}$)$_{q2NPL}$—R$^4$, wherein:
$R^3$, $R^{3'}$, and $R^{3''}$ are independently selected from the group consisting of hydrogen, alkyl, and alkoxy;
$R^4$ is selected from the group consisting of hydrogen, alkyl, alkenyl, alkynyl, cycloalkyl, aryl, and heteroaryl, any of which is optionally substituted with one or more alkyl or halo groups;
$U^{NPL}$ is absent or selected from the group consisting of O, S, —S(=O)—, —S(=O)$_2$—, —NR$^3$—, —(C=O)—, —(C=O)—N=N—NR$^3$—, —(C=O)—NR$^3$—N=N—, —N=N—NR$^3$—, —C(=N—N(R$^3$)$_2$)—, —C(=NR$^3$)—, —C(=O) O—, —C(=O)S—, —C(=S)—, —O—R(=O)$_2$ O—, —R$^3$O—, —R$^3$S—, —S—C=N— and —(C=O)—NR$^3$—O—, wherein groups with two chemically nonequivalent termini can adopt both possible orientations;
the —(CH$_2$)$_{pNPL}$— alkylene chain is optionally substituted with one or more amino or hydroxyl groups, or the alkylene chain is unsaturated;

pNPL is 0 to 8;

q1NPL and q2NPL are independently 0 to 2;

PL is a polar group selected from the group consisting of halo, hydroxyethoxymethyl, methoxyethoxymethyl, polyoxyethylene, and $-(NR^{5'})_{q1PL}-U^{PL}-(CH_2)_{pPL}-(NR^{5''})_{q2PL}-V$, wherein:

$R^5$, $R^{5'}$, and $R^{5''}$ are independently selected hydrogen, alkyl, and alkoxy;

$U^{PL}$ is absent or selected from the group consisting of O, S, $-S(=O)-$, $-S(=O)_2-$, $-NR^5-$, $-(C=O)-$, $-(C=O)-N=N-NR^5-$, $-(C=O)-NR^5-N=N-$, $-N=N-NR^5-$, $-C(=N-N(R^5)_2)-$, $-C(=NR^5)-$, $-C(=O)O-$, $-C(=O)S-$, $-C(=S)-$, $-O-P(=O)_2O-$, $-R^5O-$, $-R^5S-$, $-S-C=N-$ and $-(C=O)-NR^5-O-$, wherein groups with two chemically nonequivalent termini can adopt both possible orientations;

V is selected from the group consisting of nitro, cyano, amino, hydroxyl, alkoxy, alkylthio, alkylamino, dialkylamino, $-NH(CH_2)_pNH_2$, $-N(CH_2CH_2NH_2)_2$, diazamino, amidino, guanidino, guanyl, semicarbazone, aryl, heterocycle and heteroaryl, any of which is optionally substituted with one or more of amino, halo, cyano, nitro, hydroxyl, $-NH(CH_2)_pNH_2$, $-N(CH_2CH_2NH_2)_2$, amidino, guanidino, guanyl, aminosulfonyl, aminoalkoxy, aminoalkythio, lower acylamino, or benzyloxycarbonyl;

the $-(CH_2)_{pPL}-$ alkylene chain is optionally substituted with one or more amino or hydroxyl groups, or the alkylene chain is unsaturated;

wherein p is 0 to 8;

pPL is 0 to 8;

q1PL and q2PL are independently 0 to 2; and m is 1 to about 25;

with the proviso that if $A_1$ and $A_2$ are thiophene, the polar (PL) group(s) cannot be 3-(propionic acid) or methoxy(diethoxy)ethyl and the non-polar (NPL) group(s) cannot be n-dodecyl;

and a pharmaceutically acceptable carrier or diluent;

wherein the microbial infection is a bacterial infection.

2. The method of claim 1, wherein $A_1$ and $A_2$ are optionally substituted m-phenylene.

3. The method of claim 1, wherein one of $A_1$ or $A_2$ is substituted with one or more polar (PL) group(s) and one or more non-polar (NPL) group(s) and the other of $A_1$ or $A_2$ is unsubstituted.

4. The method of claim 1, wherein one of $A_1$ or $A_2$ is substituted with one or more polar (PL) group(s) and the other of $A_1$ or $A_2$ is unsubstituted.

5. The method of claim 1, wherein $R^1$ is (i) hydrogen, a polar group (PL), or a non-polar group (NPL), and $R^2$ is -$A_1$-$R^1$, wherein $A_1$ is as defined above and is optionally substituted with one or more polar (PL) group(s), one or more non-polar (NPL) group(s), or a combination of one or more polar (FL) group(s) and one or more non-polar (NPL) group(s); or (ii) A'-s- and $R^2$ is -$A_1$-s-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s).

6. The method of claim 5, wherein $R^1$ is hydrogen or a polar group (PL), and $R^2$ is -$A_1$-$R^1$, where $A_1$ is optionally substituted with one or more polar (PL) group(s).

7. The method of claim 1, wherein q1NPL, q2NPL, q1PL, and q2PL are independently 0 or 1.

8. The method of claim 7, wherein each of q1NPL, q2NPL, q1PL, and q2PL is 0.

9. The method of claim 1, wherein NPL is $-(NR^{3'})_{q1NPL}-U^{NPL}-(CH_2)_{pNPL}-(NR^{3''})_{q2NPL}-R^4$, and $R^3$, $R^{3'}$, $R^{3''}$, $R^4$, $U^{NPL}$, pNPL, q1NPL and q2NPL are as defined in claim 1.

10. The method of claim 1, wherein $R^3$, $R^{3'}$, and $R^{3''}$ are independently selected from the group consisting of hydrogen, $C_1$-$C_6$ alkyl, and $C_1$-$C_6$ alkoxy.

11. The method of claim 1, wherein $R^4$ is selected from the group consisting of hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups.

12. The method of claim 1, wherein $U^{NPL}$ is O, S, $-S(=O)-$, $-S(=O)_2-$, $-NH-$, $-(C=O)-$, $-(C=O)-N=N-NH-$, $-(C=O)-NH-N=N-$, $-N=N-NH-$, $-C(=N-N(R^3)_2)-$, $-C(=NR^3)-$, $-C(=O)O-$, $-C(=O)S-$, $-C(=S)-$, $-O-P(=O)_2O-$, $-R^3O-$, $-R^3S-$, $-S-C=N-$ or $-(C=O)-NR^3-O-$, wherein groups with two chemically nonequivalent termini can adopt both possible orientations.

13. The method of claim 12, wherein $U^{NPL}$ is O, $-NH-$, $-(C=O)-$, $-(C=O)-N=N-NH-$, $-(C=O)-NH-N=N-$, $-C(=N-N(R^3)_2)-$, $-C(=NR^3)-$, $-C(=O)O-$, or $-R^3O-$.

14. The method of claim 1, wherein PL is $-(NR^{5'})_{q1PL}-U^{PL}-(CH_2)_{pPL}-(NR^{5''})_{q2PL}-V$, and $R^5$, $R^{5'}$, $R^{5''}$, V, $U^{PL}$, pPL, q1PL and q2PL are as defined above in claim 1.

15. The method of claim 1, wherein $R^5$, $R^{5'}$, and $R^{5''}$ are independently hydrogen, $C_1$-$C_6$ alkyl, or $C_1$-$C_6$ alkoxy.

16. The method of claim 15, wherein each of $R^5$, $R^{5'}$, and $R^{5''}$ is hydrogen.

17. The method of claim 1, wherein, wherein $U^{PL}$ is O, S, $-S(=O)-$, $-S(=O)_2-$, $-NH-$, $-(C=O)-$, $-(C=O)-N=N-NH-$, $-(C=O)-NH-N=N-$, $-N=N-NH-$, $-C(=N-N(R^5)_2)-$, $-C(=NR^5)-$, $-C(=O)O-$, $-C(=O)S-$, $-C(=S)-$, $-O-P(=O)_2O-$, $-R^5O-$, $-R^5S-$, $-S-C=N-$ or $-(C=O)-NR^5-O-$, wherein groups with two chemically nonequivalent termini can adopt both possible orientations.

18. The method of claim 17, wherein $U^{PL}$ is O, $-NH-$, $-(C=O)-$, $-(C=O)-N=N-NH-$, $-(C=O)-NH-N=N-$, $-C(=N-N(R^5)_2)-$, $-C(=NR^5)-$, $-C(=O)O-$, or $-R^5O-$.

19. The method of claim 1, wherein V is selected from the group consisting of amino, $C_1$-$C_6$ alkylamino, $C_1$-$C_6$ dialkylamino, $-NH(CH_2)_pNH_2$, $-N(CH_2CH_2NH_2)_2$, diazamino, amidino, guanidino, guanyl, and semicarbazone, any of which is optionally substituted with one or more of amino, halo, cyano, nitro, hydroxyl, $-NH(CH_2)_pNH_2$, $-N(CH_2CH_2NH_2)_2$, amidino, guanidino, guanyl, aminosulfonyl, aminoalkoxy, lower acylamino, or benzyloxycarbonyl.

20. The method of claim 19, wherein heteroaryl is selected from the group consisting of 1,2,3-triazole, 1,2,4-triazole, 5-amino-1,2,4-triazole, imidazole, oxazole, isoxazole, 1,2,3-oxadiazole, 1,2,4-oxadizaole, 3-amino-1,2,4-oxadiazole, 1,2,5-oxadiazole, 1,3,4-oxadiazole, pyridine, and 2-aminopyridine.

21. The method of claim 1, wherein pPL and pNPL are independently 0 to 4.

22. The method of claim 1, wherein m is 1 to about 10.

23. The method of claim 1, wherein m is 1 to about 5.

24. The method of claim 23, wherein m is 1, 2 or 3.

25. The method of claim 1, wherein:

$A_1$ and $A_2$ are independently optionally substituted m-phenylene, wherein (i) one of $A_1$ or $A_2$ is substituted with one or more polar (PL) group(s) and one or more nonpolar (NPL) group(s), and the other of $A_1$ or $A_2$ is unsubstituted; or (ii) one of $A_1$ or $A_2$ is substituted with one or more polar (PL) group(s) and the other of $A_1$ or $A_2$ is unsubstituted;

$R^1$ is
(i) hydrogen, a polar group (PL), or a non-polar group (NPL), and $R^2$ is $-A_1-R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or (ii) A'-s- and $R^2$ is $-A_1$-s-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s);

NPL is $-(NR^3)_{q1NPL}-U^{NPL}-(CH_2)_{pNPL}-(NR^{3''})_{q2NPL}-R^4$, wherein $R^3$, $R^{3'}$, and $R^{3''}$ are independently selected from the group consisting of hydrogen, $C_1-C_6$ alkyl, and $C_1-C_6$ alkoxy;

$R^4$ is selected from the group consisting of hydrogen, $C_1-C_{10}$ alkyl, $C_3-C_{18}$ branched alkyl, $C_2-C_{10}$ alkenyl, $C_2-C_{10}$ alkynyl, $C_3-C_8$ cycloalkyl, $C_6-C_{10}$ aryl, and heteroaryl, any of which is optionally substituted with one or more $C_1-C_6$ alkyl or halo groups;

$U^{NPL}$ is absent or selected from the group consisting of O, S, $-S(=O)-$, $-S(=O)_2-$, $-NH-$, $-(C=O)-$, $-(C=O)-N=N-NH-$, $-(C=O)-NH-N=N-$, $-N=N-NH-$, $-C(=N-N(R^3)_2)-$, $-C(=NR^3)-$, $-C(=O)O-$, $-C(=O)S-$, $-C(=S)-$, $-O-P(=O)_2O-$, $-R^3-O-$, $-R^3-S-$, $-S-C=N-$ and $-(C=O)-NR^3-O-$, wherein groups with two chemically nonequivalent termini can adopt both possible orientations;

the alkylene chain $-(CH_2)_{pNPL}-$ is optionally substituted with one or more amino or hydroxyl groups;

pNPL is 0 to 6;

q1NPL and q2NPL are independently 0 or 1;

PL is halo or $-(NR^5)_{q1PL}-U^{PL}-(CH_2)_{pPL}-(NR^{5''})_{q2PL}-V$, wherein $R^5$, $R^{5'}$, and $R^{5''}$ are independently selected from the group consisting of hydrogen, $C_1-C_6$ alkyl, and $C_1-C_6$ alkoxy;

$U^{PL}$ is absent or selected from the group consisting of O, S, $-S(=O)-$, $-S(=O)_2-$, $-NH-$, $-(C=O)-$, $-(C=O)-N=N-NH-$, $-(C=O)-NH-N=N-$, $-N=N-NH-$, $-C(=N-N(R^5)_2)-$, $-C(=NR^5)-$, $-C(=O)O-$, $-C(=O)S-$, $-C(=S)-$, $-O-P(=O)_2O-$, $-R^5O-$, $-R^5S-$, $-S-C=N-$ and $-(C=O)-NR^5-O-$, wherein groups with two chemically nonequivalent termini can adopt both possible orientations;

V is selected from the group consisting of nitro, cyano, amino, hydroxyl, $C_1-C_6$ alkoxy, $C_1-C_6$ alkylthio, $C_1-C_6$ alkylamino, $C_1-C_6$ dialkylamino, $-NH(CH_2)_pNH_2$, $-N(CH_2CH_2NH_2)_2$, diazamino, amidino, guanidino, guanyl, semicarbazone, $C_6-C_{10}$ aryl, heterocycle, and heteroaryl, any of which is optionally substituted with one or more of amino, halo, cyano, nitro, hydroxyl, $-NH(CH_2)_pNH_2$, $-N(CH_2CH_2NH_2)_2$, amidino, guanidino, guanyl, aminosulfonyl, aminoalkoxy, lower acylamino, or benzyloxycarbonyl;

the alkylene chain $-(CH_2)_{pPL}-$ is optionally substituted with one or more amino or hydroxyl groups;

wherein p is 0 to 8;

pPL is 0 to 6;

q1PL and q2PL are independently 0 or 1; and m is 1 to about 5.

26. A method of killing or inhibiting the growth of a microorganism, said method comprising contacting the microorganism with an effective amount of an oligomer of Formula I:

$$R^1-[-A_1-s-A_2-s-]_m-R^2 \qquad (I)$$

or an acceptable salt or solvate thereof, wherein:

(i) $A_1$ and $A_2$ are independently optionally substituted arylene or optionally substituted m-heteroarylene, wherein $A_1$ and $A_2$ is substituted with one or more polar (PL) group(s), one or more non-polar (NPL) group(s), or a combination of one or more polar (PL) group(s) and one or more non-polar (NPL) group(s), and the other of $A_1$ or $A_2$ is substituted; or (ii) one of $A_1$ or $A_2$ is as defined above and is optionally substituted with one or more polar (PL) group(s), one or more non-polar (NPL) group(s), or a combination of one or more polar (PL) group(s) and one or more non-polar (NPL) group(s); and the other of $A_1$ or $A_2$ is the group $-C\equiv C(CH_2)_pC\equiv C-$, wherein p is 0 to 8, and the $-(CH_2)_p-$ alkylene chain is optionally substituted with one or more amino or hydroxyl groups;

s is $-C\equiv C-$;

$R^1$ is (i) hydrogen, a polar group (PL), or a non-polar group (NPL), and $R^2$ is $-A_1-R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and $R^2$ is $-A_1$-s-$A_2-R^1$, wherein each of $A_1$ and $A_2$ is as defined above and is optionally substituted with one or more polar (PL) group(s), one or more non-polar (NPL) group(s), or a combination of one or more polar (PL) group(s) and one or more non-polar (NPL) group(s); or (iii) A'-s- and $R^2$ is $-A_1$-s-A', wherein A' is aryl or heteroaryl, either of which is optionally substituted with one or more polar (PL) group(s), one or more non-polar (NPL) group(s), or a combination of one or more polar (PL) group(s) and one or more non-polar (NPL) group(s); or (iv) A'-s- and $R^2$ is -A', wherein A' is aryl or heteroaryl, either of which is optionally substituted with one or more polar (PL) group(s), one or more non-polar (NPL) groups(s), or a combination of one or more polar (PL) group(s) and one or more non-polar (NPL) group(s); or (v) $R^1$ and $R^2$ together form a single bond;

NPL is a non-polar group independently selected from $-B(OR^4)_2$ or $-(NR^3)_{q1NPL}-U^{NPL}-(CH_2)_{pNPL}-(NR^{3''})_{q2NPL}-R^4$, wherein:

$R^3$, $R^{3'}$, and $R^{3''}$ are independently selected from the group consisting of hydrogen, alkyl, and alkoxy;

R$^4$ is selected from the group consisting of hydrogen, alkyl, alkenyl, alkynyl, cycloalkyl, aryl, and heteroaryl, any of which is optionally substituted with one or more alkyl or halo groups;

U$^{NPL}$ is absent or selected from the group consisting of O, S, —S(=O)—, —S(=O)$_2$—, —NR$^3$—, —(C=O)—, —(C=O)—N=N—NR$^3$—, —(C=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N— and —(C=O)—NR$^3$—O—, wherein groups with two chemically nonequivalent termini can adopt both possible orientations;

the —(CH$_2$)$_{pNPL}$— alkylene chain is optionally substituted with one or more amino or hydroxyl groups, or the alkylene chain is unsaturated;

pNPL is 0 to 8;

q1NPL and q2NPL are independently 0 to 2;

PL is a polar group selected from the group consisting of halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5''}$)$_{q2PL}$—V, wherein:

R$^5$, R$^{5'}$, and R$^{5''}$ are independently selected from the group consisting of hydrogen, alkyl, and alkoxy;

U$^{PL}$ is absent or selected from the group consisting of O, S, —S(=O)—, —S(=O)$_2$—, —NR$^5$—, —(C=O)—, —(C=O)—N=N—NR$^5$—, —(C=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —(C=O)—NR$^5$—O—, wherein groups with two chemically nonequivalent termini can adopt both possible orientations;

V is selected from the group consisting of nitro, cyano, amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone, aryl, heterocycle and heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, amidino, guanidino, guanyl, aminosulfonyl, aminoalkoxy, aminoalkythio, lower acylamino, or benzyloxycarbonyl;

the —(CH$_2$)$_{pPL}$— alkylene chain is optionally substituted with one or more amino or hydroxyl groups, or the alkylene chain is unsaturated;

wherein p is 0 to 8;

p1PL is 0 to 8;

q1PL and q2PL are independently 0 to 2; and m is 1 to about 500;

with the proviso that if A$_1$ and A$_2$ are thiophene, the polar (PL) group(s) cannot be 3-(propionic acid) or methoxy(diethoxy)ethyl and the non-polar (NPL) group(s) cannot be n-dodecyl.

wherein the microorganism is a bacterial cell.

* * * * *